(12) United States Patent
Kaplan et al.

(10) Patent No.: US 11,154,559 B2
(45) Date of Patent: Oct. 26, 2021

(54) METHODS AND COMPOSITIONS OF BILE ACIDS

(71) Applicants: The General Hospital Corporation, Boston, MA (US); Ethicon Endo-Surgery, Inc., Cincinnati, OH (US)

(72) Inventors: Lee M. Kaplan, Wellesley, MA (US); Nadia N. Ahmad, Medford, MA (US); Jason L. Harris, Mason, OH (US); Kevin D. Felder, Cincinnati, OH (US); Alessandro Pastorelli, Rome (IT)

(73) Assignees: Ethicon Endo-Surgery, Inc., Cincinnati, OH (US); The General Hospital Corporation, Boston, MA (US)

(*) Notice: Subject to any disclaimer, the term of this patent is extended or adjusted under 35 U.S.C. 154(b) by 1393 days.

(21) Appl. No.: 13/631,095

(22) Filed: Sep. 28, 2012

(65) Prior Publication Data

US 2013/0116218 A1   May 9, 2013

Related U.S. Application Data

(60) Provisional application No. 61/540,952, filed on Sep. 29, 2011.

(51) Int. Cl.
*A61K 31/56* (2006.01)
*A61K 35/413* (2015.01)

(52) U.S. Cl.
CPC ............ *A61K 31/56* (2013.01); *A61K 35/413* (2013.01)

(58) Field of Classification Search
CPC combination set(s) only.
See application file for complete search history.

(56) References Cited

U.S. PATENT DOCUMENTS

| | | | |
|---|---|---|---|
| 5,631,138 A | 5/1997 | Kano et al. | |
| 2001/0024658 A1 | 9/2001 | Chen et al. | |
| 2002/0035089 A1 | 3/2002 | Barbier et al. | |
| 2006/0073213 A1* | 4/2006 | Hotamisligil | A61K 31/13 424/600 |
| 2006/0240013 A1 | 10/2006 | Golz et al. | |
| 2008/0182832 A1 | 7/2008 | Pellicciari et al. | |
| 2009/0074895 A1 | 3/2009 | Mikov et al. | |
| 2010/0093861 A1 | 4/2010 | Hermansen et al. | |
| 2010/0130426 A1* | 5/2010 | Young | A61K 9/0031 514/10.8 |
| 2011/0086829 A1* | 4/2011 | Zadini | A61K 31/575 514/182 |
| 2011/0183899 A1* | 7/2011 | Ozcan | A61K 38/2264 514/5.3 |
| 2012/0165792 A1 | 6/2012 | Ortiz et al. | |

FOREIGN PATENT DOCUMENTS

| | | | |
|---|---|---|---|
| EP | 2208497 | * | 7/2010 |
| WO | 00/037077 A1 | | 6/2000 |
| WO | 02/028411 A1 | | 4/2002 |
| WO | 02/067895 A2 | | 9/2002 |
| WO | 2009/105897 A1 | | 9/2009 |

OTHER PUBLICATIONS

Lindor, K.L. Ursodeoxycholic acid for the treatment of primary biliary cirrhosis. New Eng. J. Med. 357:15, pp. 1524-1529 (2007).*
Lim et al. Ursodeoxycholic acid and primary biliary cirrhosis. Brit. Med. J. 309, pp. 491-492 (1994).*
Bray et al. Suppression of appetite by bile acids. The Lancet 1066-1067 (May 18, 1968).*
Watanabe et al. Bile acids induce energy expenditure by promoting intracellular thyroid hormone activation. Nature 439(26): pp. 484-489 (2006). (Year: 2006).*
Baxter et al. Bile acids heat things up. Nature 439(26), pp. 402-403 (2006). (Year: 2006).*
Biolab Medical Unit, Nutritional and Environmental Medicine. Serum Total Bile Acids (Oct. 2010). (Year: 2010).*
Marschall et al., "Ursodeoxycholic Acid for Treatment of Fatty Liver Disease and Dyslipidemia in Morbidly Obese Patients", Digestive Diseases, Jun. 2011, vol. 29, No. 1, pp. 117-118 (Year: 2011).*
Ahmad et al., 494 Roux-en-Y Gastric Bypass Selectively Accelerates the Post-Prandial Rise in Circulating Taurine- and Glycine-Conjugated Bile Acids. Gastroenterology. 2010;138(5)(S1):S-70. Abstract.
Boatright et al.,Tool from ancient pharmacopoeia prevents vision loss. Mol Vis. Dec. 29, 2006;12:1706-14.
Bobeldijk et al., Quantitative profiling of bile acids in biofluids and tissues based on accurate mass high resolution LC-FT-MS: compound class targeting in a metabolomics workflow. J Chromatogr B Analyt Technol Biomed Life Sci. Aug. 15, 2008;871(2):306-13.
Brufau et al., Plasma bile acids are not associated with energy metabolism in humans. Nutr Metab (Lond). Sep. 3, 2010;7:73.

(Continued)

*Primary Examiner* — Heidi Reese
(74) *Attorney, Agent, or Firm* — Mintz Levin Cohn Ferris Glovsky and Popeo, P.C.

(57) ABSTRACT

Methods and compositions are provided for treating metabolic disorders by modulating bile acid levels. Generally, the methods and compositions can modulate bile acid levels, such as serum bile acid levels, to treat a metabolic disorder. In one embodiment, a method of modulating a bile acid level includes measuring a bile acid level and delivering a composition effective to modulate the bile acid level. A method for modulating a bile acid profile includes comparing a bile acid profile to a target profile and delivering a bile acid cocktail to increase bile acid levels. In another embodiment, a pharmaceutical composition for increasing bile acid levels includes a bile acid cocktail effective to increase bile acid levels. The composition is further useful as part of an implantable system.

19 Claims, 50 Drawing Sheets

(56) References Cited

OTHER PUBLICATIONS

Cypess et al., Identification and importance of brown adipose tissue in adult humans. N Engl J Med. Apr. 9, 2009;360(15)1509-17.

Glicksman et al., Postprandial plasma bile acid responses in normal weight and obese subjects. Ann Clin Biochem Sep. 2010 47:482-484.

Greenfield et al., Evaluation of postprandial serum bile acid response as a test of hepatic function. Dig Dis Sci 1986; 31(8):785-91.

International Search Report and Written Opinion for Application No. PCT/US2012/57958, dated Dec. 4, 2012. (11 pages).

Katsuma et al., Bile acids promote glucagon-like peptide-1 secretion through TGR5 in a murine enteroendocrine cell line STC-1. Biochem Biophys Res Commun. Apr. 1, 2005;329(1):386-90.

Kawamata et al., A G Protein-coupled Receptor Responsive to Bile Acids ; J. Biol. Chem. 2003 278: 9435-9440.

Stylopoulos et al., W1854 Roux-en-Y Gastric Bypass Activates Brown Adipose Tissue and Increases Energy Expenditure in Obese Mice. Gastrology. 2010;138(5)(S1):S-754. Abstract.

Stylopoulos et al., W1855 Sleeve Gastrectomy and Roux-en-Y Gastric Bypass Exhibit Differential Effects on Energy Expenditure and Pancreatic Islet Function. Gastrology. 2010;138(5)(S1):S-754. Abstract.

Watanabe et al., Bile acids induce energy expenditure by promoting intracellular thyroid hormone activation. Nature. Jan. 26, 2006;439(7075):484-9. Epub Jan. 8, 2006.

\* cited by examiner

Systemic Circulation

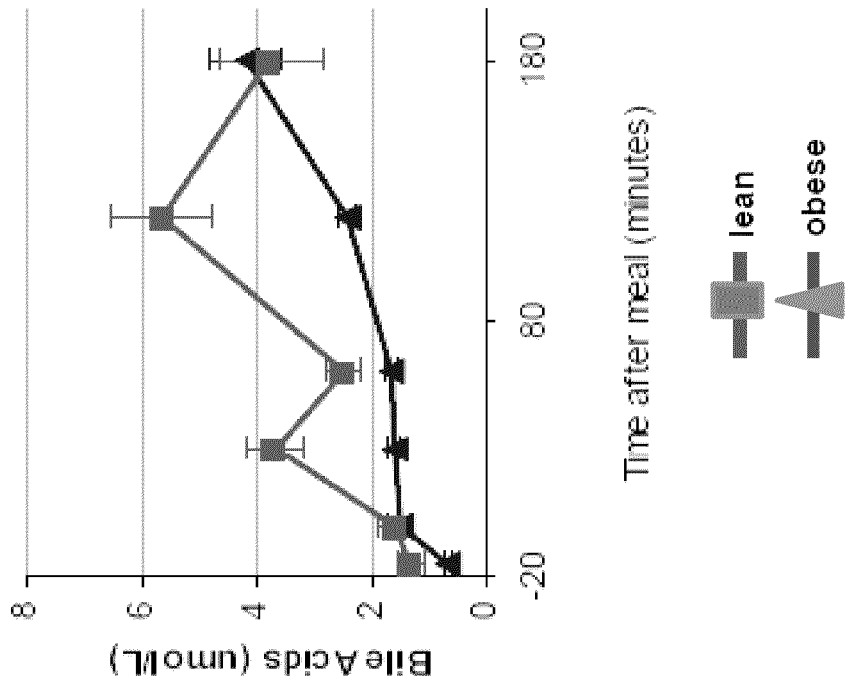
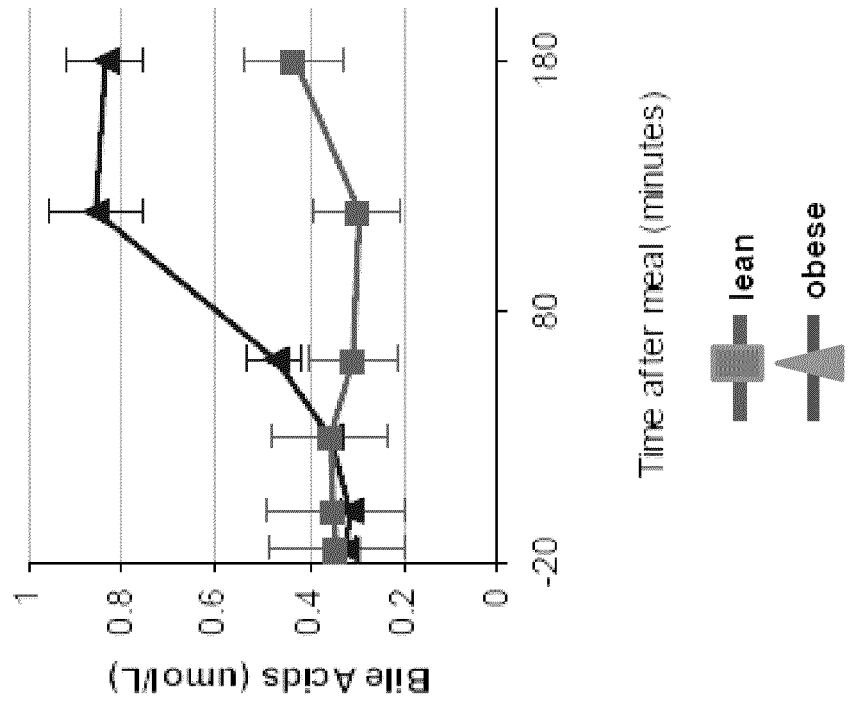

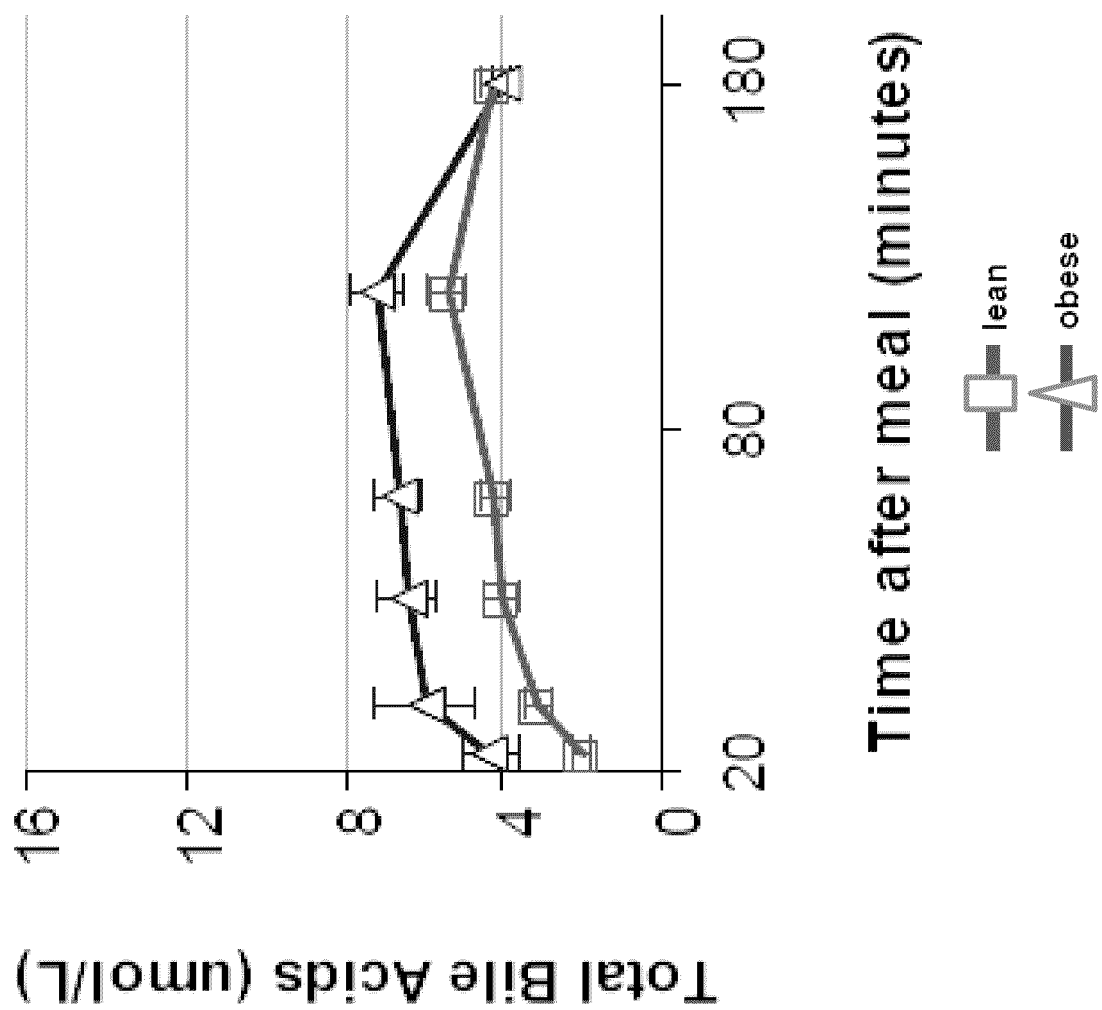

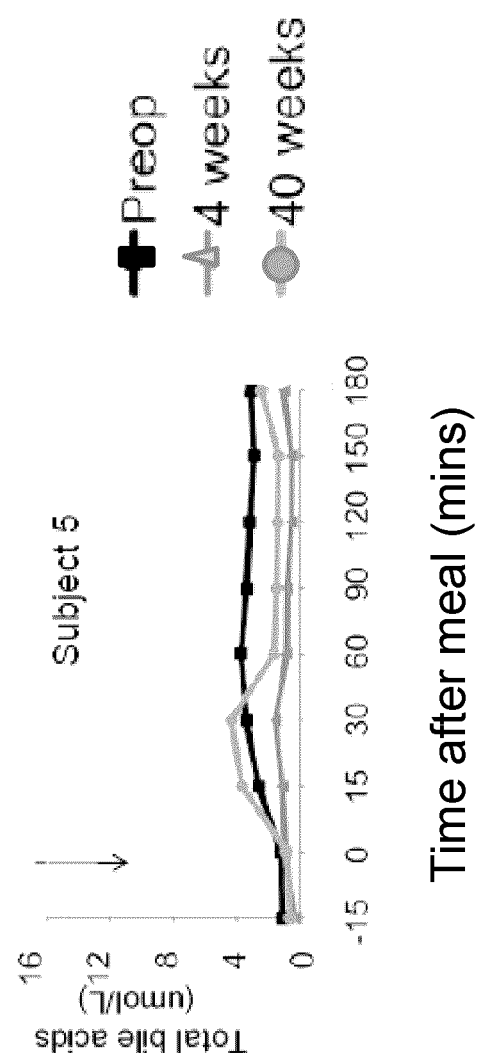

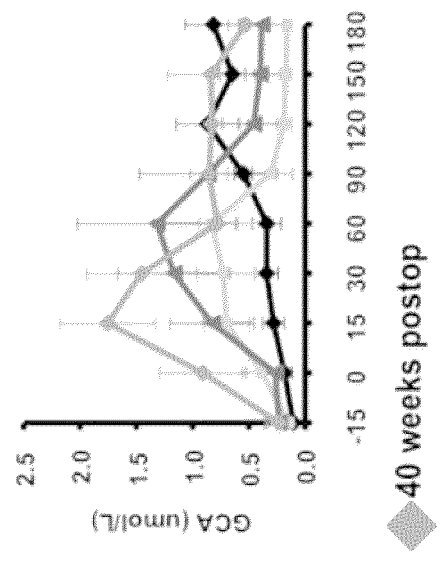
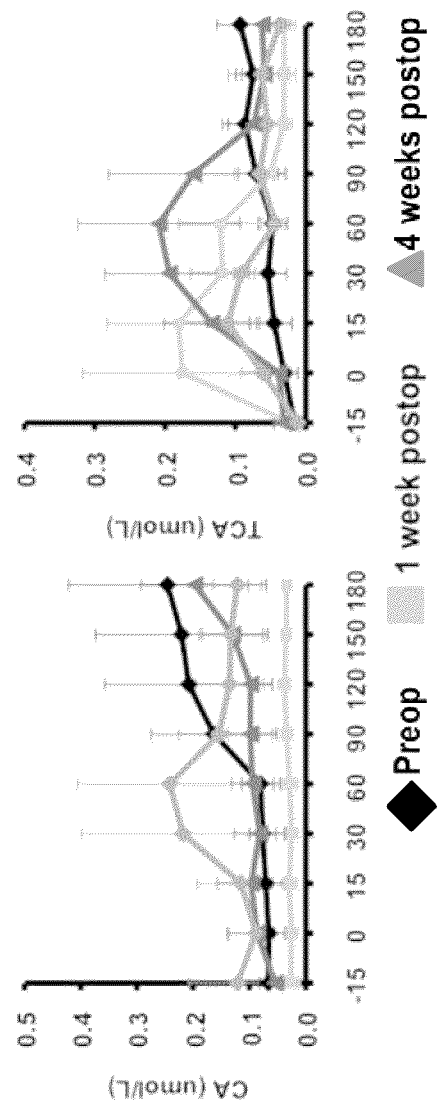
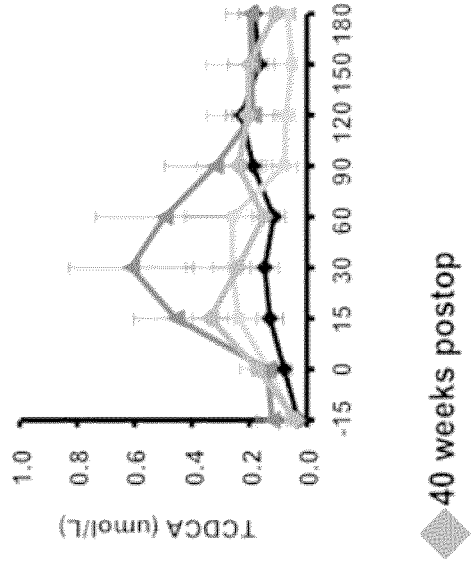
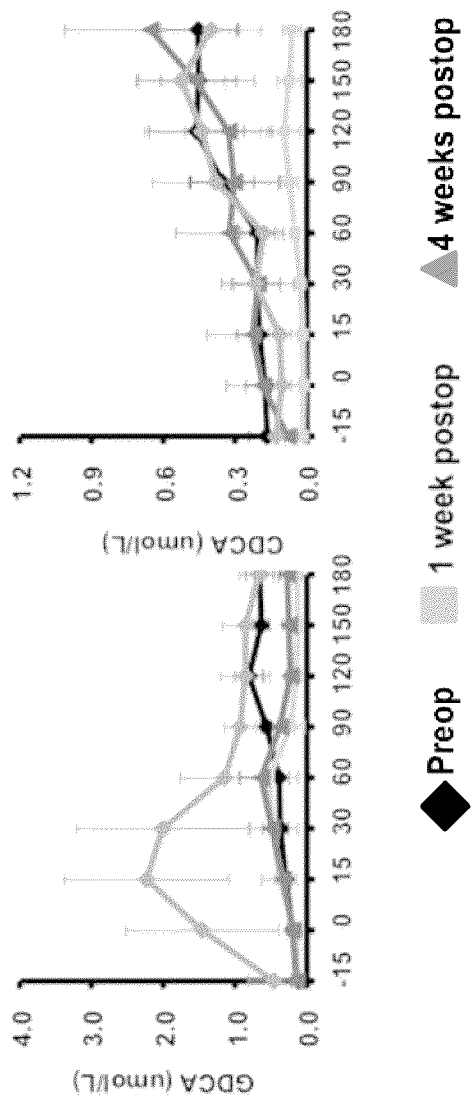

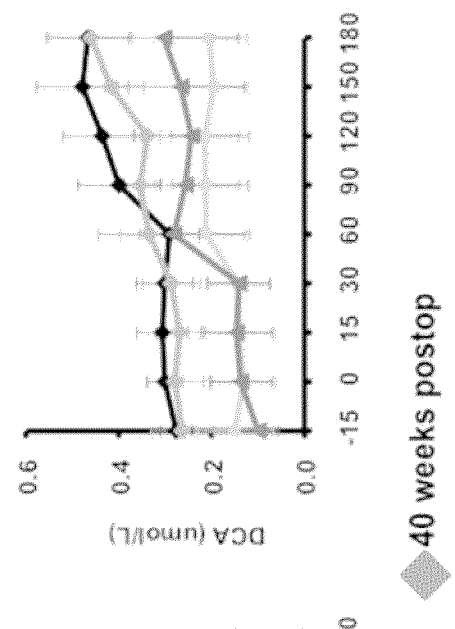
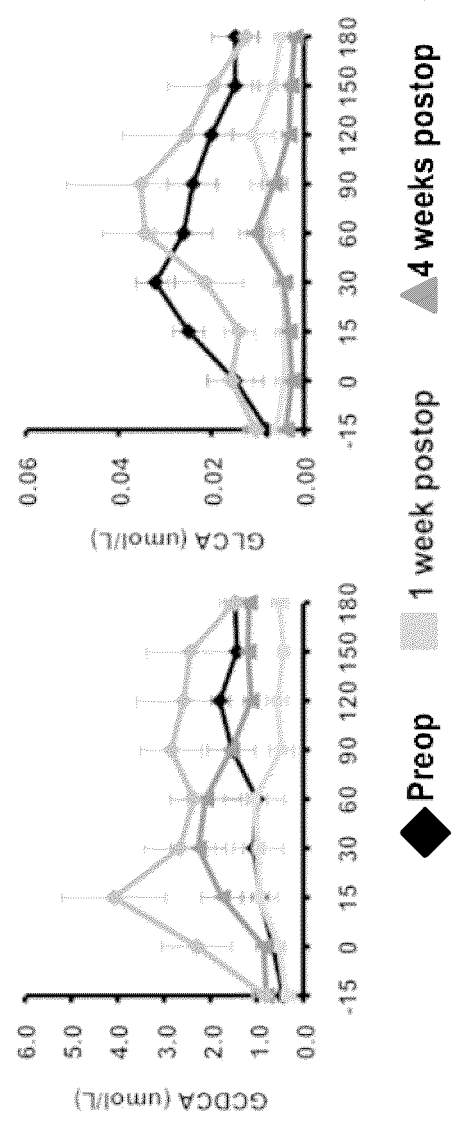
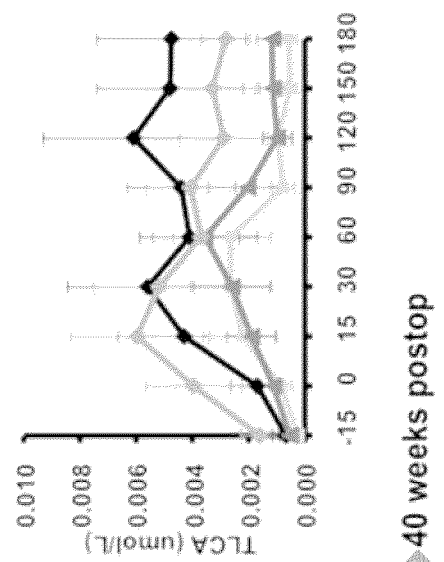
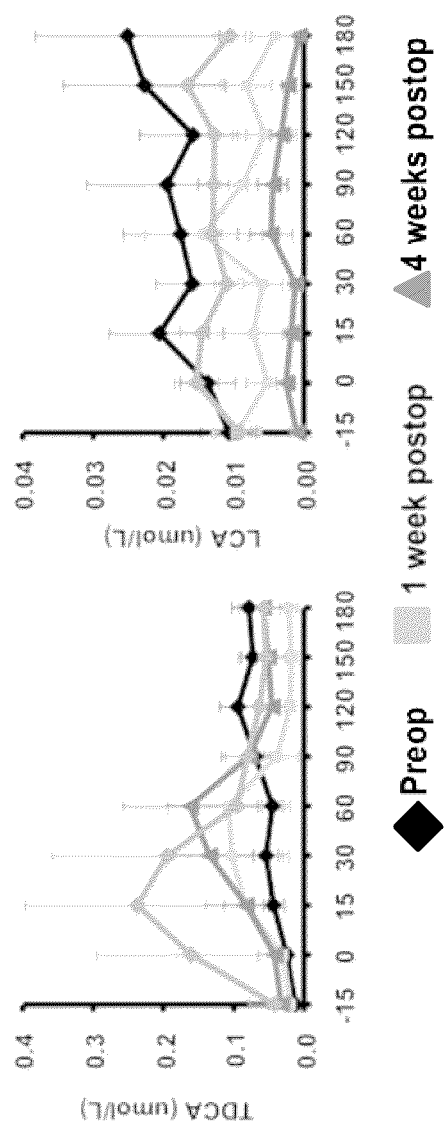

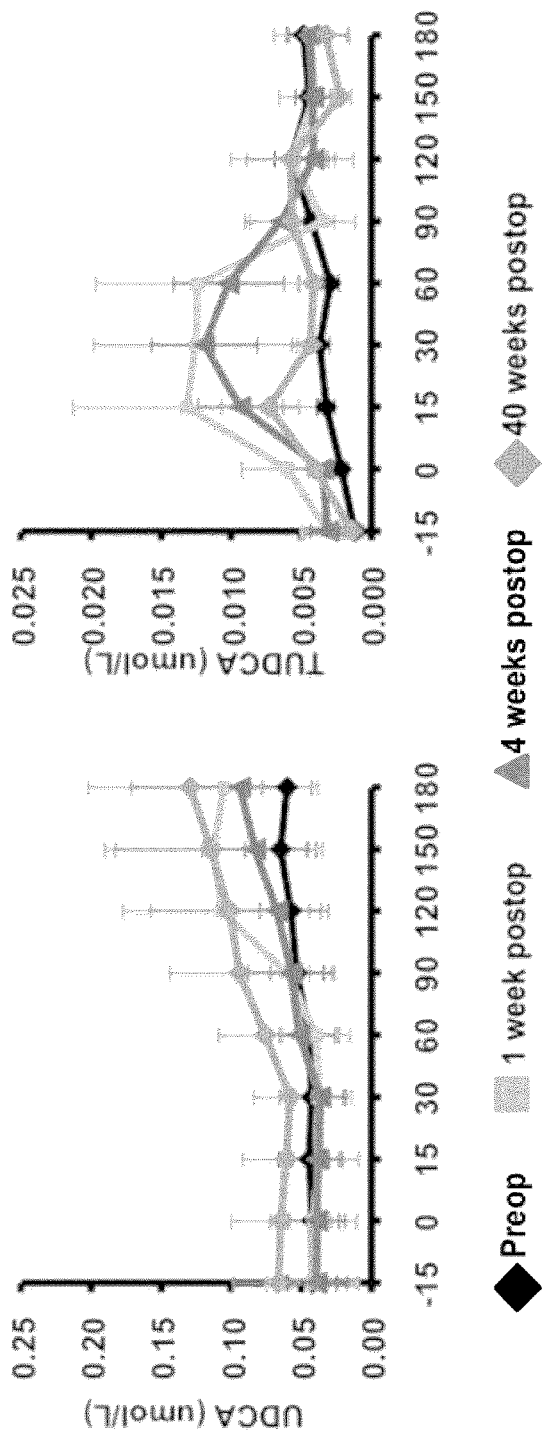
FIGURE 31M
FIGURE 31N
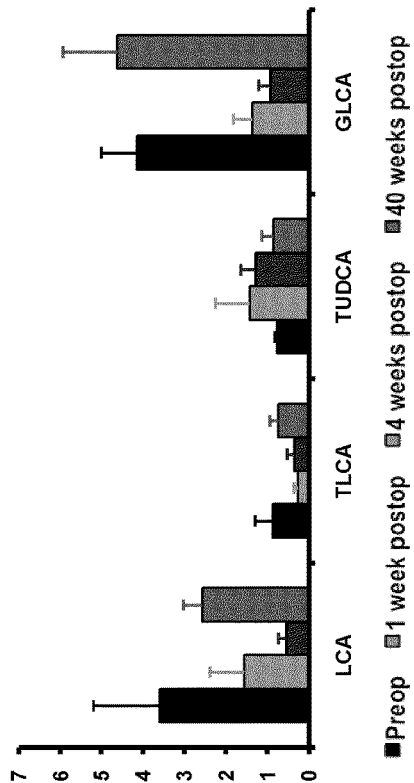
FIGURE 31O

METHODS AND COMPOSITIONS OF BILE ACIDS

FIELD OF THE INVENTION

The present invention relates to methods and compositions for the treatment of metabolic disease.

BACKGROUND OF THE INVENTION

Obesity represents the most prevalent of body weight disorders, and it is the most important nutritional disorder in the Western world, with estimates of its prevalence ranging from 30% to 50% of the middle-aged population. The number of overweight and obese Americans has continued to increase since 1960, a trend that is not slowing down. Today, 64.5% of adult Americans (about 199 million) are categorized as being overweight or obese. Severe, or Class III, obesity is becoming a growing concern as the number of people with obesity continues to increase and more is learned about the negative health effects of obesity. Each year, obesity causes at least 300,000 deaths in the U.S., and healthcare costs of American adults with obesity amount to more than $147 billion (Centers for Disease Control and Prevention). Obesity, in which a person has a body mass index equal to or greater than 40, in particular poses significant risks for severe health problems. Accordingly, a great deal of attention is being focused on treating patients with obesity.

Even mild obesity increases the risk for premature death, diabetes, hypertension, atherosclerosis, gallbladder disease and certain types of cancer. Because of its high prevalence and significant health consequences, its treatment should be a high public health priority.

Surgical procedures to treat severe obesity have included various forms of gastric and intestinal bypasses (stomach stapling), biliopancreatic diversion, adjustable gastric banding, vertical banded gastroplasty, gastric plications, and sleeve gastrectomies (removal of all or a portion of the stomach). Such surgical procedures have increasingly been performed laparoscopically. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall. Despite advances in laparoscopic techniques, such surgical procedures still risk a variety of complications during surgery, pose undesirable post-operative consequences such as pain and cosmetic scarring, and often require lengthy periods of patient recovery. Patients with obesity thus rarely seek or accept surgical intervention, with less than about 1% of patients with obesity being surgically treated for this disorder. Furthermore, even if successfully performed and initial weight loss occurs, surgical intervention to treat obesity may not result in sufficient and/or lasting weight loss, thereby indicating a patient's need for additional, different obesity treatment.

Nonsurgical procedures for treating obesity have also been developed. However, effective therapies for increasing energy expenditure leading to improvements in metabolic outcomes, e.g., decreasing food intake, weight loss, glucose metabolism etc., have focused on pharmaceutical approaches, which have various technical and physiological limitations.

Accordingly, there is a need for improved methods and devices for treating obesity and metabolic disorders.

SUMMARY OF THE INVENTION

The present invention generally provides methods and compositions for treating metabolic disorders by modulating bile acid levels. One aspect discloses methods and compositions to modulate bile acid levels to treat a metabolic disorder, including excess weight and/or a comorbid condition. The method of modulating bile acid level includes measuring a bile acid level and delivering a composition effective to modulate bile acid levels. Another aspect discloses methods and compositions to modulate serum bile acid levels, such as increasing or decreasing serum bile acid levels, in a subject to treat a metabolic disorder. The method includes modulating a bile acid profile by comparing a bile acid profile to a target profile and delivering a bile acid cocktail to increase bile acid levels. The formulations and pharmaceutical composition are also included as part of a system that is on the skin or at least partially implantable.

One aspect includes a method of modulating a serum bile acid level in a subject by measuring at least one bile acid level, determining a dosage based on the bile acid level that is effective to modulate the bile acid level, and delivering to the subject a composition comprising an effective amount of at least one bile acid where the composition is effective to modulate the serum bile acid level thereby treating a metabolic disorder.

In one embodiment, the method includes delivering the compositions to a select region or by a different mode. Regions for targeted delivery can include a circulatory system, an enterohepatic circulation, a portal circulation, a gastrointestinal tract, a gall bladder, an intestine, a liver, and a brain. The modes of delivery can include parenterally, intramuscularly, subcutaneously, perorally, or orally.

In another embodiment, the method includes delivering a bile acid composition. The composition can include one or more bile acid compounds. The composition can include bile acids, bile acid alcohols, sterols, salts thereof, and bile acid sequestrants. The composition can include primary and/or secondary bile acids. The composition can include a cocktail with a mixture of at least one primary and at least one secondary bile acid. The composition can include conjugated and/or unconjugated bile acids. The composition can include sulfated or glucuronidated bile acids. Some exemplary examples of bile acids can include, but are not limited to, cholic acid, cholate, deoxycholic acid, deoxycholate, hyodeoxycholic acid, hyodeoxycholate, glycocholic acid, glycocholate, taurocholic acid, taurocholate and the like. In one embodiment, the composition can include at least one cholic acid, taurine conjugated bile acid, primary taurine conjugated bile acid, secondary taurine conjugated bile acid, sulfated bile acid, and a bile acid sequestrant.

In yet another embodiment, the method includes delivering the composition pre-prandial and/or post-prandial or around a physical activity. The delivery of the composition can be before, with, and/or after a meal. The delivery of the composition can be before, during, and/or after a fasting or non-meal period. The delivery of the composition can be after a last meal of a day and before breaking a fast of a second or next day. The delivery of the composition can be before, with, and/or after the first meal of the day. The delivery of the composition can be before, with, and/or after the last meal of the day. The delivery can further be within about 3 hrs of a meal.

In one embodiment, the method includes delivering the bile acid composition by increasing the serum bile acid level to a first level, decreasing the serum bile acid level to a second level, and increasing the serum bile acid level to a third level. The first, second and third levels can be associated with the movement of bile acids in enterohepatic circulation and repeated cycles of enterohepatic circulation.

In another embodiment, the method includes delivering an additional dosage of the composition. Delivering an additional dosage of the composition can include one or more additional doses of the composition. Delivering an additional dosage of the composition can be pre-prandial and/or post-prandial or around a physical activity. Delivering an additional dosage of the composition can be before, during, and/or after a meal. Delivering an additional dosage of the composition can be before, during, and/or after a fasting or non-meal period. Delivering an additional dosage of the composition can be after a last meal of a day and before breaking a fast of a second or next day. Delivering an additional dosage of the composition can be before, with, and/or after the first meal of the day. Delivering an additional dosage of the composition can be before, with, and/or after the last meal of the day. Delivering an additional dosage of the composition can be before, during, and/or after a period of physical activity. In an exemplary embodiment, delivering an additional dosage of the composition can be during a non-meal period.

In another embodiment, the delivery of the composition can be before, during, and/or after a period of physical activity. In an exemplary embodiment, the composition can be delivered during a period of physical activity.

In yet another embodiment, the compositions can be delivered with at least one agent to modulate activation of at least one bile acid receptor. The bile acid receptor can be a cell surface receptor or a nuclear receptor. The bile acid receptor can include TGR5, M3 muscarinic receptor, FXR, LXR, RXR, ROR, VDR, and PXR.

Another aspect includes a pharmaceutical composition for increasing serum bile acid levels with an amount of a bile acid cocktail effective to increase bile acid levels, where the bile acid cocktail includes a mixture of at least one primary bile acid and at least one secondary bile acid. The pharmaceutical composition can also include a pharmaceutically acceptable carrier. The pharmaceutical composition can include one or more primary and secondary bile acid compounds. The composition can include bile acids, bile acid alcohols, sterols, and salts thereof. The composition can include conjugated and/or unconjugated bile acids. The composition can include sulfated bile acids. Some exemplary examples of bile acids can include, but are not limited to cholic acid, cholate, deoxycholic acid, deoxycholate, hyodeoxycholic acid, hyodeoxycholate, glycocholic acid, glycocholate, taurocholic acid, taurocholate, and the like. In one embodiment, the bile acid cocktail can include at least a cholic acid, a taurine conjugated bile acid, a taurine conjugated primary bile acid, a taurine conjugated secondary bile acid, and a sulfated bile acid.

The compositions can also be individualized for the subject dependent on measured bile acid levels. In particular, the bile acid cocktail is formulated for an individual based on a measured bile acid level in the individual. The cocktail is tailored to the individual to include one or more bile acids at concentrations specific for that individual based on their measured bile acid levels.

The compositions can be formulated for a targeted delivery to a select region or for different routes of delivery. Regions for targeted delivery can include a circulatory system, an enterohepatic circulation, a portal circulation, a gastrointestinal tract, a gall bladder, an intestine, a liver, a brown adipocyte, a beige (or brown-like) adipocyte, a muscle, and a brain. Some examples for different routes of delivery can include an oral delivery, an injectable delivery, and a catheter delivery. The compositions can also be formulated as an oral delivery formulation. The oral delivery formulation can be a delayed release formulation, such as a pro-drug that can be converted to an active form by gastrointestinal bacteria or endogenous enzymes.

The compositions can also include at least one agent to modulate activation of at least one bile acid receptor. The bile acid receptor can be a cell surface receptor or a nuclear receptor. The bile acid receptor can include TGR5, M3 muscarinic receptor, FXR, LXR, RXR, ROR, VDR, and PXR.

The compositions can be included in a catheter delivery formulation that is disposed in a system that is on the skin or at least partially implantable.

An additional aspect includes a system that is at least partially implantable for delivering the pharmaceutical composition. The system can include an implantable system with a reservoir and a port. The system can include a programmable pump and may resemble pumps configured to deliver insulin to diabetic patients. One or more of these components may be modular, located outside of the patient, and connected to a transcutaneous delivery means which may include a port, needle, patch, or the like. The system can be configured to deliver the composition at a prescribed dosage and interval. The reservoir may include a refillable or reloadable container for holding the bile acid composition. The system can include a transluminal catheter.

Another aspect includes a method of modulating a bile acid profile in a subject by measuring a bile acid profile of the subject, comparing the subject's bile acid profile to a target profile, delivering to the subject an amount of a composition comprising a bile acid cocktail that is effective to increase bile acid levels and obtaining an additional bile acid profile measurement in the subject after delivery of the composition to modulate a bile acid profile of the subject.

In one embodiment, the method includes delivering a bile acid cocktail. The cocktail can include one or more bile acid compounds. The cocktail can include bile acids, bile acid alcohols, sterols, and salts thereof. The cocktail can include primary and/or secondary bile acids. The cocktail can include a mixture of at least one primary and at least one secondary bile acid. The cocktail can include conjugated and/or unconjugated bile acids. The cocktail can include sulfated bile acids. Some exemplary examples of bile acids can include, but are not limited to cholic acid, cholate, deoxycholic acid, deoxycholate, hyodeoxycholic acid, hyodeoxycholate, glycocholic acid, glycocholate, taurocholic acid, taurocholate and the like. In one embodiment, the cocktail can include at least one cholic acid, taurine conjugated bile acid, primary taurine conjugated bile acid, secondary taurine conjugated bile acid, and sulfated bile acid.

In another embodiment, the method includes measuring the bile acid profile by measuring molecules that may contribute, are associated with or are markers of variations in bile acid levels. The bile acid profile can include measuring glucose concentrations, leptin levels, and/or insulin levels.

In yet another embodiment, the method includes measuring a bile acid profile in a subject pre-prandial and/or post-prandial. The bile acid profile can be measured before, during, and/or after a meal. The bile acid profile can be measured before, during, and/or after a fasting or non-meal period. The bile acid profile can be measured after a last meal of a day and before breaking a fast of a second or next day. The bile acid profile can be measured before, with, and/or after the first meal of the day. The bile acid profile can be measured before, with, and/or after the last meal of the day.

In one embodiment, the method includes measuring bile acid profile in a subject before, during, and/or after a period of physical activity. In an exemplary embodiment, the bile acid profile can be measured during a period of physical activity.

In another embodiment, the method includes obtaining an additional bile acid profile measurement in a subject after delivery of the composition. Measuring an additional bile acid profile can be pre-prandial and/or post-prandial or around a physical activity. Measuring additional bile acid levels or a bile acid profile can be before, during, and/or after a meal; before, during, and/or after a fasting or non-meal period; after a last meal of a day and before breaking a fast of a second or next day; before, with, and/or after the first meal of the day; before, with, and/or after the last meal of the day; or before, during, and/or after a period of physical activity.

BRIEF DESCRIPTION OF THE DRAWINGS

The invention will be more fully understood from the following detailed description taken in conjunction with the accompanying drawings, in which:

FIG. 4A shows a graph of unconjugated bile acids present in serum for lean and obese men in relation to a meal;

FIG. 4B shows a graph of conjugated bile acids present in serum for lean and obese men in relation to a meal;

FIG. 5 shows a graph of total bile acids present in serum for lean and obese women in relation to a meal;

FIG. 7E shows a graph of total bile acids present in serum of Subject 5 preoperative 4 weeks postoperative and 40 weeks postoperative in relation to a meal;

FIG. 29A is a line graph of cholic acid (CA);
FIG. 29E is a line graph of taurochenodeoxycholic acid (TCDCA) is shown in;
FIG. 29O is a line graph of glycoursodeoxycholic acid (GUDCA);

FIG. 30A shows the AUC for all the taurine- and glycine-conjugated, primary and secondary BAs analyzed (left bar=lean, right bar=obesity);

FIG. 30B shows an enlarged bar graph of the AUC analyses for LCA, TCA, TLCA, TUDCA and GLCA (left bar=lean, right bar=obesity);

FIG. 30C is a graph of the AUC analyses for total BAs and primary, secondary, total conjugated, taurine-conjugated and glycine-conjugated BA subsets (left bar=lean, right bar=obesity);

FIGS. 31A-31Q are graphs illustrating that RYGB selectively accelerates the post-prandial rise in taurine- and glycine-conjugated BAs;

FIGS. 31A-31N show the post-prandial time course of individual plasma BAs at baseline and at 1, 4 and 40 weeks after RYGB. Each subject's preoperative baseline was calculated by averaging the BA response to a standard liquid meal at 4 weeks and 1 week before RYGB;

FIGS. 31O-31Q show the AUC analyses of the 3-hour post-prandial BA excursions. *P<0.05 compared to baseline;

DETAILED DESCRIPTION OF THE INVENTION

Figure 1:
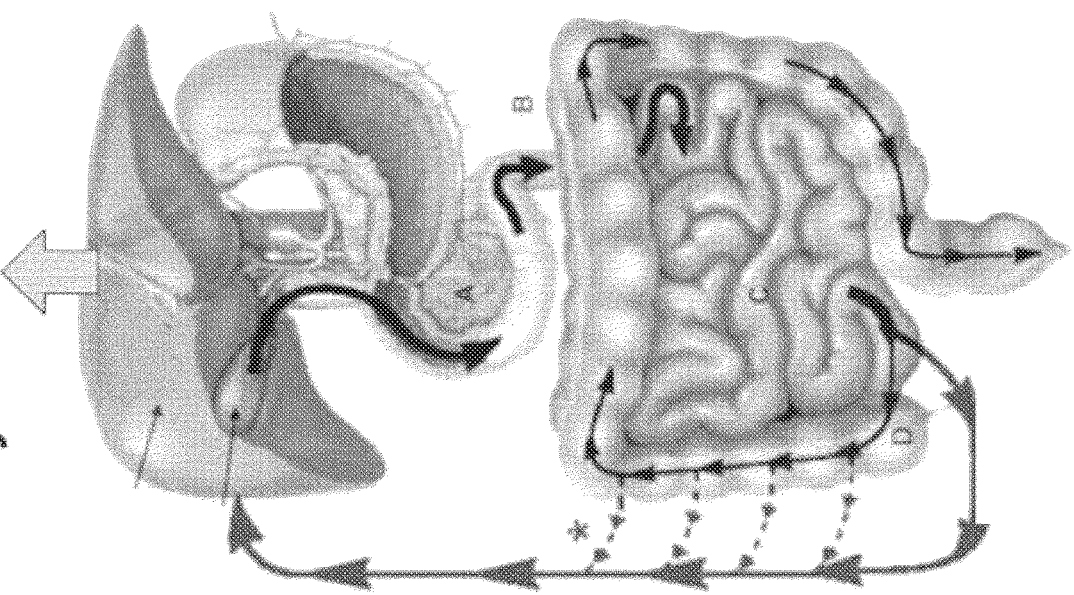
FIG. 1 is a diagram of the enterohepatic circulation.

Certain exemplary embodiments will now be described to provide an overall understanding of the principles of the structure, function, manufacture, and use of the therapeutics and methods disclosed herein. One or more examples of these embodiments are illustrated in the accompanying drawings. Those skilled in the art will understand that the therapeutics and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

All publications, patents and patent applications cited herein are hereby incorporated by reference in their entirety. As used in this specification and the appended claims, the singular forms "a," "an," and "the" include plural references unless the content clearly dictates otherwise. The terms used in this invention adhere to standard definitions generally accepted by those having ordinary skill in the art. In case any further explanation might be needed, some terms have been further elucidated below.

The invention is generally directed to therapeutic methods and compositions, separately or in combination, for treating metabolic disorders in a subject by utilizing bile acid pathways, to determine which therapeutic intervention(s), e.g.

bile acid compositions and/or dosing regimens, is appropriate. Bile acid pathway modulation can be performed either indirectly, for example, through pathway activation or directly, for example, by administration of bile acids, bile acid conjugates, or bile acid sequestrants. Additionally, the level of serum bile acids and the level of serum bile acid conjugates can be measured to determine efficacy of a therapeutic intervention to treat the metabolic disorder. The therapeutic intervention can be, for example, a composition effective for modulating bile acid levels in a subject. The therapeutic intervention can also be a pharmaceutical composition effective for modulating bile acid levels in a subject.

Bile Acid Synthesis

Bile acids promote fat absorption by acting as potent "digestive surfactants" to lipids (including fat-soluble vitamins) by acting as emulsifiers. As bile acids have been implicated as key regulators of energy balance and metabolic function through their actions on nuclear and cell surface receptors, modulating bile acid synthesis or bioavailability of bile acids provides multiple interfaces for altering energy regulation and metabolic functions in a subject.

The regulation of bile acid synthesis can occur in a feed-forward mechanism by modulating intracellular cholesterol availability. Bile acids are natural end products of cholesterol and represent the primary pathway for cholesterol catabolism, accounting for ~50% of the daily turnover of cholesterol. They are synthesized in the liver in a process that is regulated by many factors including nutrients, hormones, and bile acids. The production of bile acids is localized primarily in the perivenous hepatocytes, the cells surrounding the central hepatic vein. The synthesis of bile acids occurs in a series of enzymatic reactions in the hepatocyte that convert hydrophobic cholesterol, shown below, into more water-soluble amphipathic compounds.

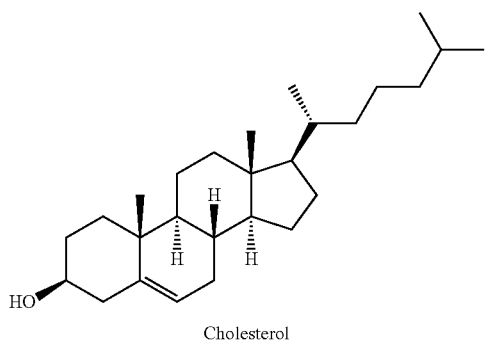
Cholesterol

Bile acids constitute a large family of molecules, composed of a steroid structure with four rings, a five or eight carbon side-chain terminating in a carboxylic acid, and the presence and orientation of different numbers of hydroxyl groups. The four rings are labeled from left to right on Bile Acid Formula, shown below as A, B, C, and D, with the D-ring being smaller by one carbon than the other three. The hydroxyl groups have a choice of being in 2 positions, beta (solid pie-shaped line), or alpha (dashed line). All bile acids have a hydroxyl group on position 3, which was derived from the parent molecule, cholesterol. In cholesterol, the 4 steroid rings are flat and the position of the 3-hydroxyl is beta.

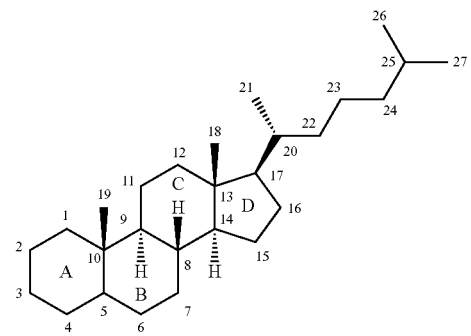
Bile Acid Formula

The immediate products of the bile acid synthetic pathways are referred to as primary bile acids. Cholic acid and chenodeoxycholic acid (shown below) are two forms of primary bile acids formed in humans. The action of intestinal bacterial flora on primary bile acids results in the formation of secondary bile acid species: deoxycholic, lithocholic, and ursodeoxycholic acid. Deoxycholic acid is derived from cholic acid and lithocholic acid and ursodeoxycholic acid are derived from chenodeoxycholic acid.

Primary Bile Acids

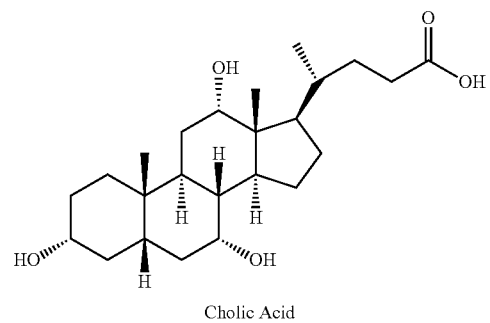
Cholic Acid

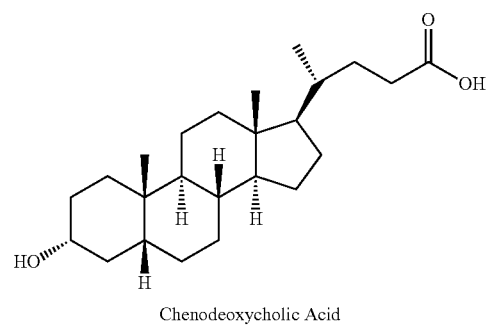
Chenodeoxycholic Acid

Secondary Bile Acids

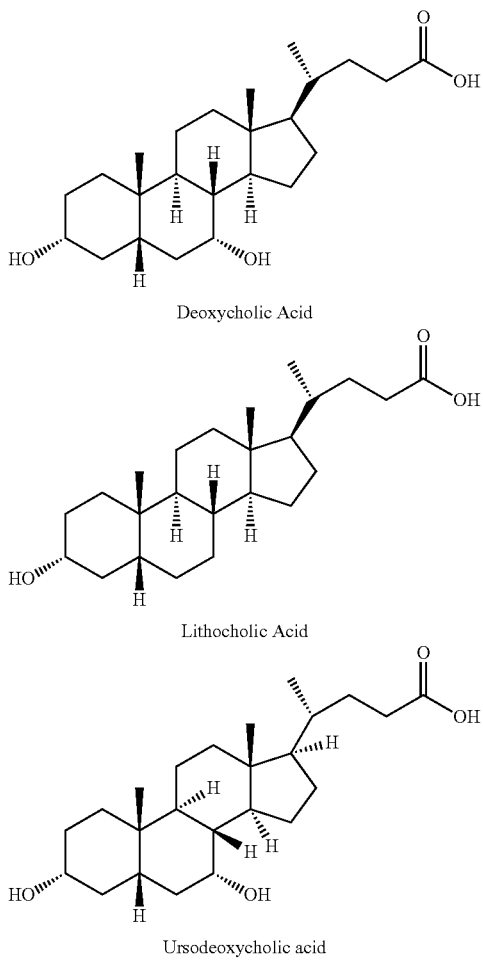

Deoxycholic Acid

Lithocholic Acid

Ursodeoxycholic acid

Much of the secreted bile acids are in the form of conjugates with the amino acids taurine or glycine and/or conjugates with sulfate. The terms "conjugating," "conjugation" and "conjugated" refer to the formation of a covalent bond. Conjugation of bile acids are catalyzed by enzymatic reactions that convert the bile acid to an acyl-CoA thioester then transfer the bile acid moiety from the acyl-CoA thioester to either glycine or taurine to form the respective bile acid conjugate. These additions substantially increase the acidity of the molecules and their solubility in water. At the physiological pH values in the intestines, the bile acid conjugates ionize and exist in salt form. In the conjugated state, the molecules cannot passively enter the epithelial cells of the biliary tract and small intestines.

The phrase "bile acid," as used herein, includes bile acid alcohols, sterols, and salts thereof, found in the bile of an animal (e.g., a human), including, by way of non-limiting example, cholic acid, cholate, deoxycholic acid, deoxycholate, hyodeoxycholic acid, hyodeoxycholate, glycocholic acid, glycocholate, taurocholic acid, taurocholate and the like. Taurocholic acid and/or taurocholate are referred to herein as TCA. Any reference to a bile acid used herein includes reference to a bile acid, one and only one bile acid, one or more bile acids, or to at least one bile acid. Therefore, the phrases "bile acid," "bile salt," "bile acid/salt," "bile acids," "bile salts," and "bile acids/salts" are, unless otherwise indicated, utilized interchangeably herein. Any reference to a bile acid used herein includes reference to a bile acid or a salt thereof. Furthermore, it is to be understood that as used herein, "bile acids" include bile acids conjugated to an amino acid (e.g., glycine or taurine). For example, the phrase "bile acid" includes cholic acid conjugated with either glycine or taurine: glycocholate and taurocholate, respectively (and salts thereof). Any reference to a bile acid used herein includes reference to an identical compound naturally or synthetically prepared. Furthermore, it is to be understood that any singular reference to a component (bile acid or otherwise) used herein includes reference to one and only one, one or more, or at least one of such components. Similarly, any plural reference to a component used herein includes reference to one and only one, one or more, or at least one of such components, unless otherwise noted.

Bile Acid Profiles

Gall bladder and/or biliary ductal contraction with feeding releases bile acids into the intestine. In the lumen of the intestine, the microbiota metabolize bile acids, where conjugated bile acids are deconjugated and primary bile acids are converted to secondary bile acids. Bile acids then undergo enterohepatic circulation, i.e. absorbed in the intestine and taken up by hepatocytes for re-excretion into bile. See FIG. 1. After their absorption from the intestine, bile acids return to the liver and inhibit their own synthesis in a feedback regulatory loop. The controlled synthesis and export of bile acids from the liver to the biliary system involves several synthetic/metabolic (conjugation as well as different bile acids) enzymes.

Figure 2:
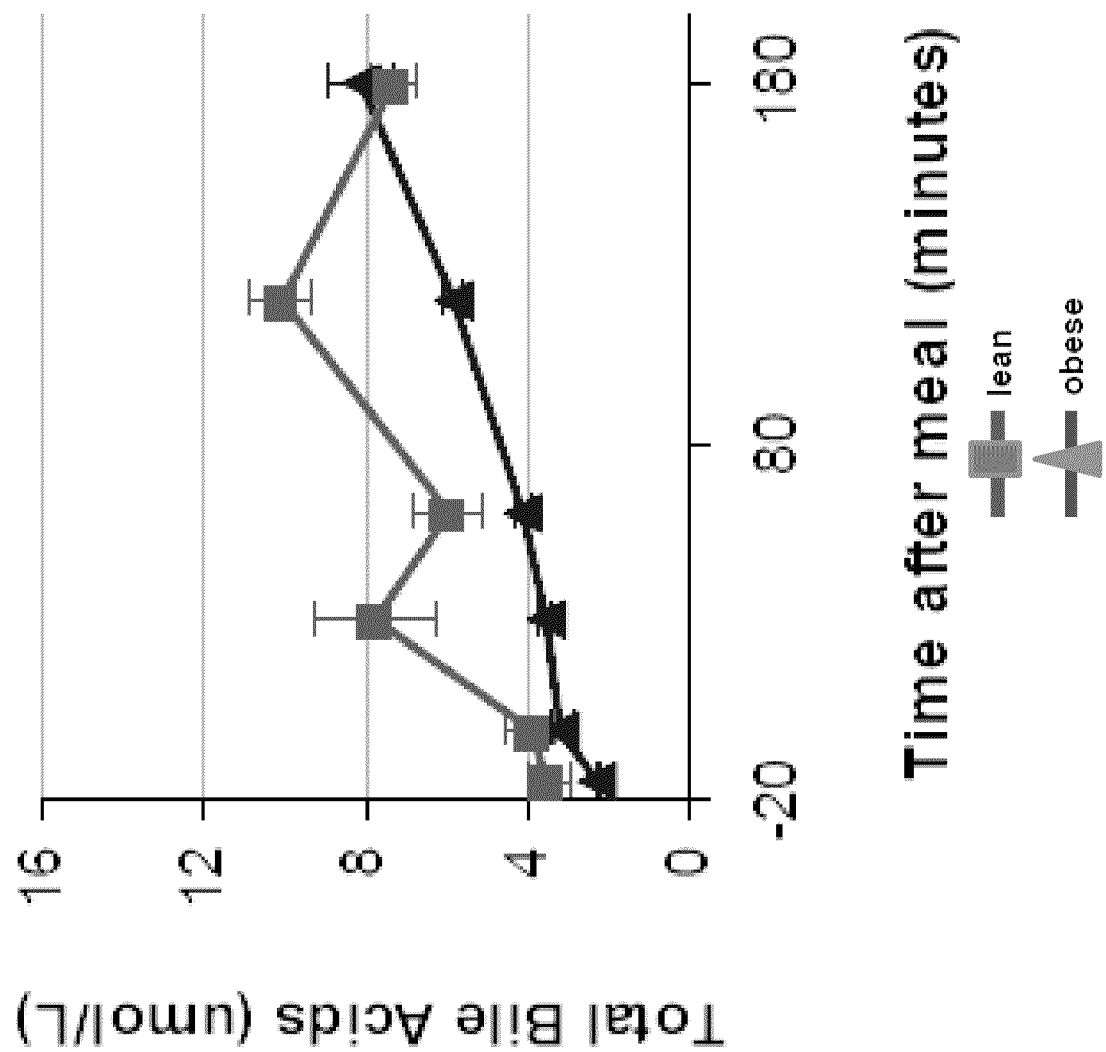
FIG. 2 is a graph of total bile acids present in serum for lean and obese men in relation to a meal.

The efficiency of the hepatic clearance of bile acids from portal blood maintains serum concentrations at low levels in the fasting state in normal persons. An elevated fasting level, due to impaired hepatic clearance, is a sensitive indicator of liver disease. Following meals, serum bile acid levels triple and demonstrate cycling in normal persons (FIG. 2), but in obesity there is a blunted post-prandial rise in serum bile acid levels and no cycling is apparent. Whereas, marked increases in serum bile acid levels are seen in patients with various liver diseases, including cirrhosis, hepatitis, cholestasis, portal-vein thrombosis, Budd-Chiari syndrome, cholangitis, Wilson's disease, and hemochromatosis, individuals with intestinal malabsorption do not show increases in serum bile acid levels.

Circulating bile acid levels can also correlate with measures of metabolic function. These measurements can be used to generate a bile acid profile. The phrase "bile acid profile," as used herein, refers to the measurement of bile acid levels, total bile acids, individual bile acids or any combination of individual bile acids, taken at a specific time before, during, or after an activity, such as ingesting food or physical activity, or over an extended time period.

Individuals that lack changes between periods of fasting and after meals, or display changes in their bile acid profile that are inconsistent with a healthy subject's bile acid profile, may be more likely to have a metabolic disorder. The term "metabolic disorder" as used herein, refers to disorders, diseases, and comorbid conditions that are caused or characterized by abnormal energy use or consumption, altered responses to ingested or endogenous nutrients, energy sources, hormones or other signaling molecules within the body or altered metabolism of carbohydrates, lipids, proteins, nucleic acids or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain) or the like. Some non-limiting examples can be obesity, diabetes, including type II diabetes, insulin-resistance syndrome, syndrome X, inflammatory and immune disorders, dyslipidemia metabolic syndrome, cancer, neurodegenerative disorders, hypertension, high cholesterol, atherogenic dyslipidemia, hyperlipidemic conditions such as atherosclerosis, hypercholesterolemia, and other coronary artery diseases in mammals, and other disorders of metabolism.

As used herein, the term "obesity" or "obese" typically refers to a non-Asian individual having a body mass index (BMI) of ≥25 kg/m$^2$ or an Asian individual having a BMI of ≥23 kg/m$^2$. BMI is a measure expressing the relationship (or ratio) of weight-to-height based on a mathematical formula in which a person's body weight in kilograms is divided by the square of his or her height in meters (i.e., wt/(ht)$^2$). Individuals having a BMI of ≥25 kg/m$^2$ in non-Asians or ≥23 kg/m$^2$ in Asians have an increased risk of at least one weight-related co-morbid condition or having a metabolic disorder or syndrome.

As used herein, the terms "co-morbidity" or co-morbid condition" typically refers to, but is not limited to, hypertension, dyslipidemia, high triglyceride levels, diabetes, acid reflux, fatty liver disease, steato-hepatitis, heart disease, heart failure, cardiovascular risk, depression, sleep apnea, Barrett's esophagus, asthma, arthritis, compression fractures, gallstones, lymphoedema, urinary incontinence, stroke, cognitive dysfunction, inflammatory diseases, autoimmune diseases, gout, polycystic ovarian syndrome, infertility, anxiety and/or panic disorders, cancer risk and mortality (cancers including adenocarcinoma of pancreas, esophagus, gallbladder, pancreas, colon, rectum, breast, prostate; cervical carcinoma, endometrial carcinoma, ovarian carcinoma, renal cell carcinoma, non-Hodgkins lymphoma), weight regain, excess weight loss, nutritional deficiency, constipation, diarrhea, marginal ulceration, dumping syndrome, reactive hypoglycemia, beta cell hyperfunction, gastrointestinal stenosis, liver disorders, nausea/vomiting and/or other metabolic syndromes.

The phrase "metabolic syndrome" refers to a cluster of conditions or disorders that occur together, and increase the risk for heart disease, stroke, diabetes, and obesity. Having just one of these conditions such as increased blood pressure, elevated insulin levels, excess body fat around the waist or abnormal cholesterol levels can increase the risk of the above mentioned diseases. In combination, the risk for coronary heart disease, stroke, insulin-resistance syndrome, and diabetes is even greater.

Measuring Bile Acids

The increasing prevalence of obesity in the population has led to a parallel rise in surgical procedures, like bariatric surgery, as a treatment for obesity and related comorbid conditions. Surgical procedures can achieve a sustained weight reduction of up to 50% of excess body weight in the majority of patients, and are more effective than nonsurgical approaches. It has been discovered that gastric bypass can not only lead to early satiety, increased energy expenditure and durable weight loss, but can also alter, i.e. normalize, the post-prandial bile acid response to bile acid cycling. Therefore, in an exemplary embodiment, a method of modulating bile acid levels in a subject can be used to treat a metabolic disorder.

The terms "modulating," "modulate," or "modulation" refer to altering, adjusting, increasing, decreasing or the process of altering, adjusting, increasing, or decreasing bile acid levels in a subject.

The terms "treating," "treatment" or "intervention" refer to the administration or delivery of one or more therapeutic agents, compositions or procedures to a subject who has a condition or disorder or a predisposition toward a condition or disorder, with the purpose to prevent, alleviate, relieve, alter, remedy, ameliorate, improve, affect, slow or stop the progression, slow or stop the worsening of the disease, at least one symptom of condition or disorder, or the predisposition toward the condition or disorder. In one embodiment, treating a metabolic disorder can include preventing, alleviating, ameliorating, and/or improving the metabolic disorder; inducing weight loss and/or preventing weight gain; and preventing, alleviating, ameliorating, and/or improving comorbid conditions.

The term "subject" as used herein refers to any living organism, including, but not limited to, humans, nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. The term does not denote a particular age or sex. In a specific embodiment, the subject is human.

The method of modulating bile acid levels can include measuring one or more bile acid levels. The bile acid levels can be measured by obtaining a sample from a subject. The sample can be a whole blood, plasma, serum, urine, saliva, cerebral spinal fluid, tissue such as liver, intestine, gall bladder, stomach, brain, tissue fluid such as bile from the gall bladder, intestinal fluid, liver fluid, ascites, and any other sample that is used by those familiar with measuring bile acids. In an exemplary embodiment, a serum bile acid level is measured.

The bile acid measurement can include measuring total bile acids, individual bile acid compounds or measuring a combination of more than one bile acid, taken at a specific time before, during, and/or after an activity, such as ingesting food or physical activity, or over an extended time period. The bile acid measurements can include one or more of any of the bile acid compounds, bile acid alcohol, sterols, and salts thereof, found in the bile of an animal (e.g., a human), including, by way of non-limiting example, cholic acid, cholate, deoxycholic acid, deoxycholate, hyodeoxycholic acid, hyodeoxycholate, glycocholic acid, glycocholate, taurocholic acid, taurocholate and the like. In one embodiment, the bile acid measurements can include total bile acids. In another embodiment, the bile acid measurements can include serum bile acids. In yet another embodiment, the bile acid measurements can include a cholic acid, a taurine conjugated bile acid, a primary taurine conjugated bile acid, a secondary taurine conjugated bile acid and a sulfated bile acid.

The bile acid levels can also be assessed before the ingestion of food, pre-prandial, and/or after the ingestion of food, post-prandial. The term "pre-prandial," as used herein, refers to the fasting response or the response before the ingestion of food. The term "post-prandial," as used herein, refers to a response after the ingestion of food. Measurements of both pre-prandial and post-prandial bile acids can be useful to generate a bile acid profile. In an exemplary embodiment, measurements of bile acid levels can be obtained before, during, and/or after the ingestion of food or a meal. These measurements can be used to generate a bile acid profile.

In one embodiment, one or more measurements of bile acid levels or a bile acid profile can be obtained before, during, and/or after a fasting or non-meal period. The non-meal period can be after a last meal of a day and before breaking a fast of a second or next day. In another embodiment, the measurement or profile can be obtained before, during, and/or after the first meal of the day. In yet another embodiment, the measurement or profile can be obtained before, during, and/or after the last meal of the day. In another embodiment, the measurement or profile can be obtained at least about 0 mins, 5 mins, 10 mins, 15 mins, 20 mins, 25 mins, 30 mins, 35 mins, 40 mins, 45 mins, 50 mins, 55 mins, 1 hr, 1.5 hrs, 2 hrs, 2.5 hrs, 3 hrs, 3.5 hrs, 4 hrs, 4.5 hrs, 5 hrs, 5.5 hrs, 6 hrs, 6.5 hrs, 7 hrs, 7.5 hrs, 8 hrs, 8.5 hrs, 9 hrs, 9.5 hrs, 10 hrs, 11 hrs, 12 hrs, before, and/or after a meal.

In one embodiment, the measurement or profile can be obtained before, during, and/or after a period of physical activity. In another embodiment, the measurement or profile can be performed at least about 0 mins, 5 mins, 10 mins, 15 mins, 20 mins, 25 mins, 30 mins, 35 mins, 40 mins, 45 mins, 50 mins, 55 mins, 1 hr, 1.5 hrs, 2 hrs, 2.5 hrs, 3 hrs, 3.5 hrs, 4 hrs, 4.5 hrs, 5 hrs, 5.5 hrs, 6 hrs, 6.5 hrs, 7 hrs, 7.5 hrs, 8 hrs, 8.5 hrs, 9 hrs, 9.5 hrs, 10 hrs, 11 hrs, 12 hrs, before, and/or after a period of physical activity.

One or more bile acid measurements can be compared to a target profile. The target profile can be a normalized bile acid profile from a healthy subject of similar weight, age, gender, race, etc. The target profile can be a standardized bile acid profile obtained from a population of subjects of similar weight, age, gender, race, etc. The term "target profile" is intended to encompass any standard or normal bile acid profile that is useful as a benchmark against which "altered bile acid profiles" can be measured. One skilled in the art can select a reference target profile in a myriad of ways so long as statistically relevant measurements can be obtained. For example, a target profile, or target profile for bile acids can be selected as the average level exhibited by healthy young adults (e.g., aged 25 to 30 years old). Other standards or normal target profiles can be chosen depending upon the particular applications.

One or more bile acid measurements can be repeated before, during, and/or after a therapeutic intervention, such as delivery of a composition to modulate bile acid levels. The repeated bile acid measurements can also be used to generate an additional bile acid profile. By comparing bile acid measurements or profiles before and after a therapeutic intervention, comparisons can be made about the efficacy of the therapeutic intervention. Obtaining a bile acid measurement or profile after a therapeutic intervention and comparing with pre-therapeutic measurements or profiles can also be used to determine or assess modifications that may be useful in subsequent therapeutic interventions. The repeated bile acid measurement or profile can be performed similar to the initial bile acid measurement or profile. The repeated bile acid measurement or profile can be performed before, during, and/or after the first meal of the day. In yet another embodiment, repeated bile acid measurement or profile can be performed before, during, and/or after the last meal of the day. In another embodiment, repeated bile acid measurement or profile can be performed at least about 0 mins, 5 mins, 10 mins, 15 mins, 20 mins, 25 mins, 30 mins, 35 mins, 40 mins, 45 mins, 50 mins, 55 mins, 1 hr, 1.5 hrs, 2 hrs, 2.5 hrs, 3 hrs, 3.5 hrs, 4 hrs, 4.5 hrs, 5 hrs, 5.5 hrs, 6 hrs, 6.5 hrs, 7 hrs, 7.5 hrs, 8 hrs, 8.5 hrs, 9 hrs, 9.5 hrs, 10 hrs, 11 hrs, 12 hrs, before, and/or after a meal.

In one embodiment, repeated bile acid measurement or profile can be performed before, during, and/or after a period of physical activity. In another embodiment, repeated bile acid measurement or profile can be performed at least about 0 mins, 5 mins, 10 mins, 15 mins, 20 mins, 25 mins, 30 mins, 35 mins, 40 mins, 45 mins, 50 mins, 55 mins, 1 hr, 1.5 hrs, 2 hrs, 2.5 hrs, 3 hrs, 3.5 hrs, 4 hrs, 4.5 hrs, 5 hrs, 5.5 hrs, 6 hrs, 6.5 hrs, 7 hrs, 7.5 hrs, 8 hrs, 8.5 hrs, 9 hrs, 9.5 hrs, 10 hrs, 11 hrs, 12 hrs, before, and/or after a period of physical activity.

Not only can a bile acid measurement or profile be obtained, but a measurement or profile can be obtained for other molecules that may contribute to variations in bile acid levels, such as, but not limited to, glucose concentrations, leptin levels, or insulin levels. The method of measuring other molecules that may contribute to variations in bile acid levels can include measuring the molecules in a sample from a subject. The sample can be the same sample used to obtain bile acid levels, or it can be a different sample. The sample can be, for example, whole blood, plasma, serum, urine, saliva, cerebral spinal fluid, tissue such as liver, intestine, gall bladder, stomach, brain, tissue fluid such as bile from the gall bladder, intestinal fluid, liver fluid, ascites, and any other sample that is used by those familiar with measuring bile acids.

Bile Acid Compositions

After measuring the bile acid levels, a composition in an amount effective to modulate bile acid levels can be delivered to the subject. The bile acid composition can include one or more bile acid compounds. The bile acid composition can include bile acids, bile acid alcohol, sterols, and salts thereof. The bile acid composition can include primary and/or secondary bile acids. The bile acid composition can include conjugated and/or unconjugated bile acids. The bile acid composition can include sulfated bile acids. Some exemplary examples of bile acids can include, but are not limited to cholic acid, cholate, deoxycholic acid, deoxycholate, hyodeoxycholic acid, hyodeoxycholate, glycocholic acid, glycocholate, taurocholic acid, taurocholate and the like. In one embodiment, the bile acid composition can include a cholic acid, a taurine conjugated bile acid, a primary taurine conjugated bile acid, a secondary taurine conjugated bile acid, and/or a sulfated bile acid.

The bile acid composition can include one or more bile acids. The bile acids can be present in the composition at a total concentration of about 0.001 mg/kg, 0.005 mg/kg, 0.01 mg/kg, 0.05 mg/kg, 0.1 mg/kg, 0.5 mg/kg, 1.0 mg/kg, 1.25 mg/kg, 1.5 mg/kg, 1.75 mg/kg, 2.0 mg/kg, 2.25 mg/kg, 2.5 mg/kg, 2.75 mg/kg, 3.0 mg/kg, 3.25 mg/kg, 3.5 mg/kg, 3.75 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.25 mg/kg, 9.5 mg/kg, 9.75 mg/kg, 10.0 mg/kg, 10.25 mg/kg, 10.5 mg/kg, 10.75 mg/kg, 11 mg/kg, 11.25 mg/kg, 11.5 mg/kg, 11.75 mg/kg, 12 mg/kg, 13 mg/kg, 14 mg/kg, 15 mg/kg, 16 mg/kg, 17 mg/kg, 18 mg/kg, 19 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, and any concentration in between. In one embodiment, the bile acids can be present in the composition at a total concentration in the range of about 0.001 mg/kg to about 100 mg/kg. In another embodiment, the bile acids can be present in the composition at a total concentration in the range of about 0.1 mg/kg to about 50 mg/kg. In yet another embodiment, the bile acids can be present in the composition at a total concentration in the range of about 1 mg/kg to about 10 mg/kg.

One or more bile acids can be present in the composition at an individual concentration of about 0.001 mg/kg, 0.005 mg/kg, 0.01 mg/kg, 0.05 mg/kg, 0.1 mg/kg, 0.5 mg/kg, 1.0 mg/kg, 1.25 mg/kg, 1.5 mg/kg, 1.75 mg/kg, 2.0 mg/kg, 2.25 mg/kg, 2.5 mg/kg, 2.75 mg/kg, 3.0 mg/kg, 3.25 mg/kg, 3.5 mg/kg, 3.75 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.25 mg/kg, 9.5 mg/kg, 9.75 mg/kg, 10.0 mg/kg, 10.25 mg/kg, 10.5 mg/kg, 10.75 mg/kg, 11 mg/kg, 11.25 mg/kg, 11.5 mg/kg, 11.75 mg/kg, 12 mg/kg, 13 mg/kg, 14 mg/kg, 15 mg/kg, 16 mg/kg, 17 mg/kg, 18 mg/kg, 19 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, and any concentration in between. In one embodiment, the bile acid can be present in the composition at an individual concentration in the range of about 0.001 mg/kg to about 100 mg/kg. In another embodiment, the bile acid can be present in the composition at an individual concentration in the range of about 0.1 mg/kg to about 50 mg/kg. In yet another embodiment, the bile acid can be present in the composition at an individual concentration in the range of about 1 mg/kg to about 10 mg/kg. The proportions of the individual bile acids can further be dependent on measurements of individual bile acids, primary bile acids, secondary bile acids, conjugated bile acids, or any combination thereof, obtained from the subject. The proportions bile acids can be in amounts consistent with normalizing bile acid levels. The proportions of bile acids can also be in amounts consistent with target values obtained from normal, healthy subjects, or the target profile from a standardized bile acid profile obtained from one or more subjects of similar weight, age, gender, race, etc.

In another embodiment, the bile acid composition can include one or more bile acid sequestrants to modulate bile acid levels in a subject. The phrase "bile acid sequestrants," as used herein, includes compounds that bind bile acids, bile acid conjugates, and salts thereof, to decrease reabsorption of bile acids or decrease the bioavailability of bile acids found in the gastroinstestinal tract of an animal (e.g., a human). Some non-limiting examples can include hypolipidemic agents, cholestyramine, colestipol, and colesevelam. Bile acid sequestrants, in general, can form complexes with bile acids and bile acid conjugates in the intestine and block resorbtion of bile acids from the intestine. In one embodiment, the bioavailability of one or more bile acids can be decreased. The decrease in bioavailability can be due to bile acid sequestrants in the bile acid composition.

One or more bile acid sequestrants can be present in the composition at a total concentration of about 0.001 mg/kg, 0.005 mg/kg, 0.01 mg/kg, 0.05 mg/kg, 0.1 mg/kg, 0.5 mg/kg, 1.0 mg/kg, 1.25 mg/kg, 1.5 mg/kg, 1.75 mg/kg, 2.0 mg/kg, 2.25 mg/kg, 2.5 mg/kg, 2.75 mg/kg, 3.0 mg/kg, 3.25 mg/kg, 3.5 mg/kg, 3.75 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.25 mg/kg, 9.5 mg/kg, 9.75 mg/kg, 10.0 mg/kg, 10.25 mg/kg, 10.5 mg/kg, 10.75 mg/kg, 11 mg/kg, 11.25 mg/kg, 11.5 mg/kg, 11.75 mg/kg, 12 mg/kg, 13 mg/kg, 14 mg/kg, 15 mg/kg, 16 mg/kg, 17 mg/kg, 18 mg/kg, 19 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, and any concentration in between. In one embodiment, the bile acid sequestrants can be present in the composition at a total concentration in the range of about 0.001 mg/kg to about 100 mg/kg. In another embodiment, the bile acid sequestrants can be present in the composition at a total concentration in the range of about 0.1 mg/kg to about 50 mg/kg. In yet another embodiment, the bile acid sequestrants can be present in the composition at a total concentration in the range of about 1 mg/kg to about 10 mg/kg.

One or more bile acid sequestrants can be present in the composition at an individual concentration of about 0.001 mg/kg, 0.005 mg/kg, 0.01 mg/kg, 0.05 mg/kg, 0.1 mg/kg, 0.5 mg/kg, 1.0 mg/kg, 1.25 mg/kg, 1.5 mg/kg, 1.75 mg/kg, 2.0 mg/kg, 2.25 mg/kg, 2.5 mg/kg, 2.75 mg/kg, 3.0 mg/kg, 3.25 mg/kg, 3.5 mg/kg, 3.75 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.25 mg/kg, 9.5 mg/kg, 9.75 mg/kg, 10.0 mg/kg, 10.25 mg/kg, 10.5 mg/kg, 10.75 mg/kg, 11 mg/kg, 11.25 mg/kg, 11.5 mg/kg, 11.75 mg/kg, 12 mg/kg, 13 mg/kg, 14 mg/kg, 15 mg/kg, 16 mg/kg, 17 mg/kg, 18 mg/kg, 19 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, and any concentration in between. In one embodiment, the bile acid sequestrant can be present in the composition at an individual concentration in the range of about 0.001 mg/kg to about 100 mg/kg. In another embodiment, the bile acid sequestrant can be present in the composition at an individual concentration in the range of about 0.1 mg/kg to about 50 mg/kg. In yet another embodiment, the bile acid sequestrant can be present in the composition at an individual concentration in the range of about 1 mg/kg to about 10 mg/kg. The proportions of the individual bile acid sequestrants can further be dependent on measurements of individual bile acids, primary bile acids, secondary bile acids, conjugated bile acids, or any combination thereof, obtained from the subject and binding capabilities of the sequestrant. The proportions bile acid sequestrants can be in amounts consistent to normalize bile acid levels. The proportions of bile acid sequestrants can also be in amounts consistent to obtain bile acid target values obtained from normal, healthy subjects, or a bile acid target profile from a standardized bile acid profile obtained from one or more subjects of similar weight, age, gender, race, etc.

In yet another embodiment, the bile acid composition can include one or more bile acids and one or more bile acid sequestrants to modulate bile acid levels in a subject. The combination of bile acids and bile acid sequestrants can be used to modulate specific bile acids in the subject. For example, bile acids and bile acid sequestrants can be present in the composition at individual concentrations in the range of about 0.001 mg/kg to about 100 mg/kg, in the range of about 0.1 mg/kg to about 50 mg/kg, in the range of about 0.1 mg/kg to about 50 mg/kg, or in the range of about 1 mg/kg to about 10 mg/kg. The individual bile acid or bile acid sequestrants can be present in the composition at an individual concentration of about 0.001 mg/kg, 0.005 mg/kg, 0.01 mg/kg, 0.05 mg/kg, 0.1 mg/kg, 0.5 mg/kg, 1.0 mg/kg, 1.25 mg/kg, 1.5 mg/kg, 1.75 mg/kg, 2.0 mg/kg, 2.25 mg/kg, 2.5 mg/kg, 2.75 mg/kg, 3.0 mg/kg, 3.25 mg/kg, 3.5 mg/kg, 3.75 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.25 mg/kg, 9.5 mg/kg, 9.75 mg/kg, 10.0 mg/kg, 10.25 mg/kg, 10.5 mg/kg, 10.75 mg/kg, 11 mg/kg, 11.25 mg/kg, 11.5 mg/kg, 11.75 mg/kg, 12 mg/kg, 13 mg/kg, 14 mg/kg, 15 mg/kg, 16 mg/kg, 17 mg/kg, 18 mg/kg, 19 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, and any concentration in between. The proportions of the individual bile acids and bile acid sequestrants can further be dependent on measurements of individual bile acids, primary bile acids, secondary bile acids, conjugated bile acids, or any combination thereof, obtained from the subject and the binding capabilities of the sequestrant. The proportions of bile acids and bile acid sequestrants can be in amounts consistent to normalize individual and total bile acid levels in the subject. The proportions of bile acids and bile acid sequestrants can also be in amounts consistent to obtain bile acid target values obtained from normal, healthy subjects, or a bile acid target profile from a standardized bile acid profile obtained from one or more subjects of similar weight, age, gender, race, etc.

The bile acid profile of a subject can be used to formulate an individualized therapeutic intervention. In one embodiment, the bile acid composition can be formulated to modulate bile acid levels in a subject based on the bile acid profile of the subject. In another embodiment, the bile acid composition can include a cocktail of bile acids formulated for a subject based on the bile acid profile of the subject. In yet another embodiment, the bile acid composition can be formulated to include a cocktail of bile acids to increase bile acid levels in a subject based on the measured bile acid levels. In a further embodiment, the bile acid composition can be formulated to include a cocktail of bile acids to increase serum bile acid levels. In another embodiment, the bile acid composition can be formulated to decrease the bioavailability of one or more bile acids.

In an additional embodiment, the bile acid profile of a subject can be used to formulate an individualized therapeutic intervention of a bile acid composition including one or more bile acid sequestrants. The bile acid composition can include a cocktail of bile acid sequestrants to decrease bile acid levels in a subject based on the measured bile acid levels. The bile acid composition can be formulated to include one or more bile acid sequestrants, such as cholestryamine, colestipol, and colesevelam. In one embodiment, bile acid composition can be formulated to include one or more bile acid sequestrants to decrease the bioavailability of one or more bile acids.

The bile acid composition can be formulated to modulate serum bile acid levels. In one embodiment, the bile acid composition can be formulated to increase a serum bile acid level. In another embodiment, the bile acid composition can be formulated to decrease a serum bile acid level. In an exemplary embodiment, the bile acid composition can be formulated to increase a serum bile acid level to a first level, decrease a serum bile acid level to a second level and increase a serum bile acid level to a third level. The first, second and third levels can be associated with the movement of bile acids in enterohepatic circulation and repeated cycles of enterohepatic circulation.

In another aspect, a pharmaceutical composition effective to modulate bile acid levels can be delivered. In one embodiment, the pharmaceutical composition can increase bile acid levels. In another embodiment, the pharmaceutical composition can decrease bile acid levels. The pharmaceutical composition can include one or more bile acids in a bile acid cocktail and a pharmaceutically acceptable carrier. The pharmaceutical composition can include a cocktail of bile acids, bile acid alcohols, sterols, and salts thereof in a mixture with a pharmaceutically acceptable carrier. The bile acid cocktail can include primary and/or secondary bile acids in a mixture. The bile acid cocktail can include conjugated and/or unconjugated bile acids in a mixture. The bile acid cocktail can include sulfated bile acids in a mixture. Some exemplary examples of bile acids that can be included in the mixture can include, but are not limited to cholic acid, cholate, deoxycholic acid, deoxycholate, hyodeoxycholic acid, hyodeoxycholate, glycocholic acid, glycocholate, taurocholic acid, taurocholate and the like. In one embodiment, the bile acid cocktail can include a cholic acid, a taurine conjugated bile acid, a primary taurine conjugated bile acid, a secondary taurine conjugated bile acid, and/or a sulfated bile acid in a mixture. In another embodiment, the pharmaceutical composition can be formulated in an amount effective to increase a bile acid level. In a further embodiment, the pharmaceutical composition can be formulated in an amount effective to increase a serum bile acid level.

In one embodiment, the pharmaceutical composition can decrease bile acid levels. The pharmaceutical composition can include one or more bile acid sequestrants in a cocktail and a pharmaceutically acceptable carrier. The pharmaceutical composition can include a cocktail of bile acid sequestrants to decrease bile acid levels in a subject based on the measured bile acid levels. The pharmaceutical composition can be formulated to include one or more bile acid sequestrants, such as cholestryamine, colestipol, and colesevelam. In yet another embodiment, the pharmaceutical composition can be formulated in an amount effective to decrease a bile acid level. In a further embodiment, the pharmaceutical composition can include a bile acid antagonist or other effective agent to decrease one or more serum bile acid levels.

As used herein, "pharmaceutically acceptable carrier" includes any and all solvents, dispersion media, coatings, antibacterial and antifungal agents, isotonic and absorption delaying agents, and the like that are physiologically compatible. In one embodiment, formulations and compositions of the present invention can be incorporated into pharmaceutical compositions suitable for delivery to a subject. A pharmaceutical composition may also comprise a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition.

The bile acid compositions can also include a "therapeutically effective amount," an "effective amount" or a "prophylactically effective amount." A "therapeutically effective amount" refers to an amount effective, at dosages and for periods of time necessary, to achieve the desired therapeutic result. A therapeutically effective amount of a composition may vary according to factors such as the disease state, age, sex, and weight of the individual, and the ability of the composition to elicit a desired response in the individual. A therapeutically effective amount is also one in which any toxic or detrimental effects of the composition are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Figure 3:
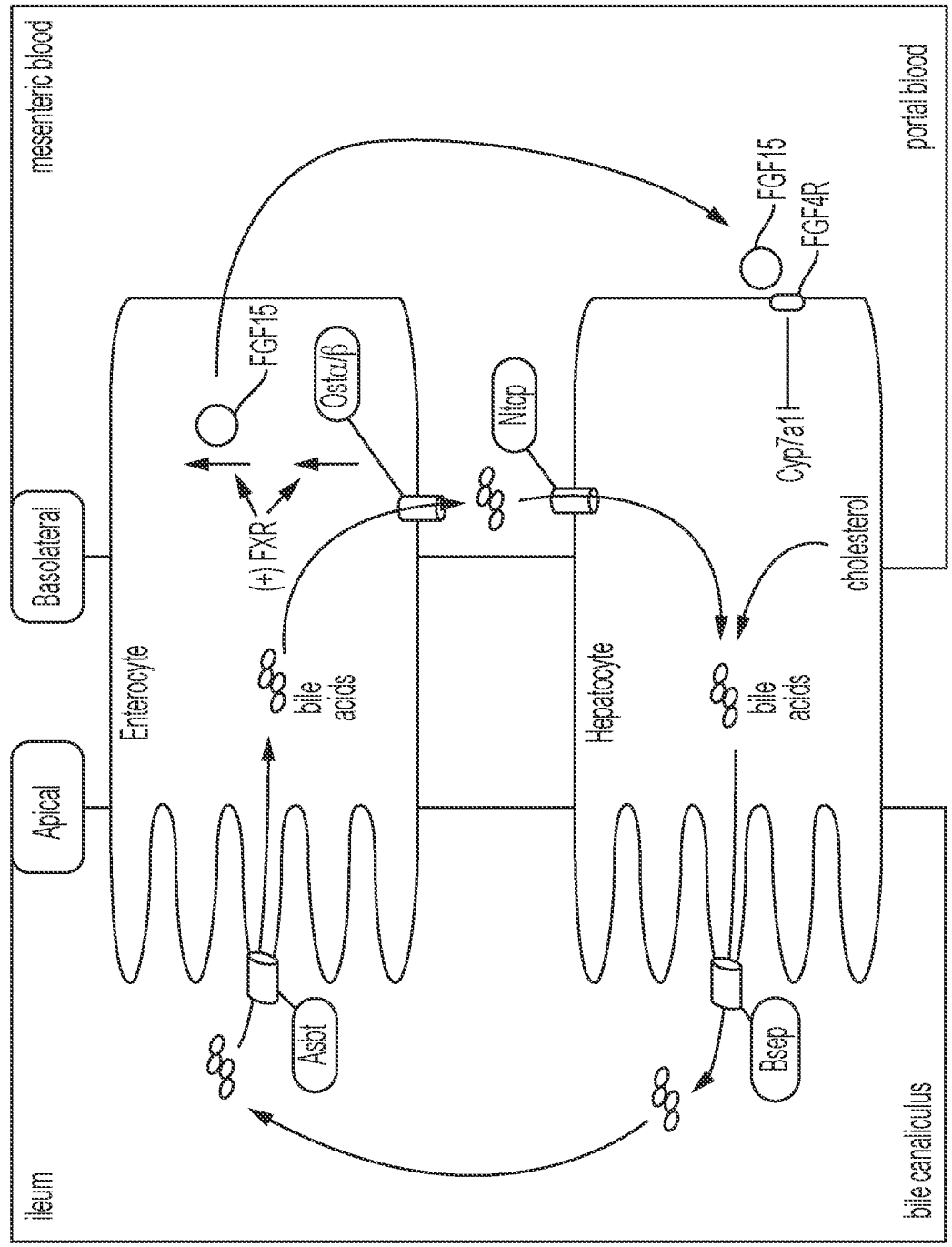
FIG. 3 is a diagram of enterocyte and hepatocyte bile transport.

The composition can also include one or more agents or compounds that modulate activation of a bile acid receptor or bile acid signaling pathway. Some nonlimiting examples of molecules that can modulate activation of the bile acid signaling pathways can include, agonists, antagonists, receptor ligands, receptor agonists, cAMP, receptor antagonists, bile acid transporters such as sodium-taurocholate cotransporting polypeptide (NTCP), organic anion-transporting polypeptides (OATPs), bile salt export pump (BSEP), canalicular conjugate export pump (multidrug resistent associated protein 2, MRP2), multidrug resistent associated protein 3 (MRP3), multidrug resistent associated protein 4(MRP4), organic solute transporter $\alpha\beta$ (Osta$\beta$), apical sodium bile salt transporter (ASBT), farnesoid X receptor/retinoid X receptor (FXR/RXR); nuclear receptors such as, farnesoid X receptor (FXR), CYP7A1, Liver X Receptors (LXR-$\alpha$ and LXR-$\beta$), retinoic acid receptor-related orphan receptors (ROR), retinoid X receptors (RXR), vitamin D receptor (VDR), pregnane X receptor (PXR) and others; and other receptors such as bile acid-dedicated G protein-coupled receptor (GPCR), TGR5 (GPR131) and muscarinic acetylcholine receptors (like M3). In one embodiment, the agent can modulate activation of a bile acid receptor. In another embodiment, the agent can modulate a cell surface receptor. See FIG. 3. In yet another embodiment, the agent can modulate a nuclear receptor. In a further embodiment, the agent can modulate a TGR5, a M3 muscarinic receptor, a FXR, a LXR, a RXR, a VDR, a ROR and a PXR.

The compositions can be formulated in a variety of forms. These include, for example, liquid, semi-solid and solid dosage forms, such as liquid solutions (e.g., injectable and infusible solutions), dispersions or suspensions, tablets, pills, powders, liposomes, suppositories, and other formulations. The compositions can also be formulated for high drug concentrations. The compositions can further be sterile and stable under the conditions of manufacture and storage. Sterile injectable solutions can be prepared by incorporating the compositions in a required amount of an appropriate solvent with one or a combination of ingredients enumerated above, as required, followed by filtered sterilization.

Exemplary forms of the compositions can depend on the intended mode of delivery and therapeutic application. Some compositions can be in the form of pill based delivery, such as disclosed in U.S. patent application Ser. No. 12/976, 648 entitled "Pill Catcher," filed Dec. 22, 2010, and delayed release methods. In one embodiment, the compositions can be formulated in a delayed release formulation. In another embodiment, the composition can be prepared with a carrier that will protect the composition against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978. "Sustained release" refers to release of a composition or an active compound thereof into the systemic circulation over a prolonged period of time relative to that achieved by delivery of a conventional formulation of the composition.

Another type of composition includes activatable forms, such as building a cocktail in the form of a pro-drug so that it is inactive by itself, and is converted by bacteria specific to the ileum and/or colon to an active form. In another embodiment, the compositions can be formulated as a pro-drug that can be converted to an active form by gastrointestinal bacteria. The composition can also be in a liquid form that is compatible with an implantable system. The composition can further be formulated to be stable at elevated temperatures, such as body temperatures, for extended periods of time. In an exemplary embodiment, the composition can be configured with an implantable system, such as a translumenal cathether.

Also included in the compositions can be a functional derivative of one or more bile acids. A "functional derivative" of a bile acid is a derivative which possesses a biological activity that is substantially similar to the biological activity of a bile acid. By "substantially similar" is meant activity which is quantitatively different but qualitatively the same. For example, a functional derivative of a bile acid would contain the same amino acid backbone but also contains other modifications such as post-translational modifications such as, for example, bound phospholipids, or covalently linked carbohydrate, depending on the necessity of such modifications for the performance of the diagnostic assay or therapeutic treatment. As used herein, the term is also meant to include a chemical derivative of a bile acid. Such derivatives may improve the composition's solubility, absorption, biological half life, affinity for receptors, etc. The derivatives may also decrease the toxicity of the composition, or eliminate or attenuate any undesirable side effect of the molecule, etc. Derivatives and specifically, chemical moieties capable of mediating such effects are disclosed in Remington's Pharmaceutical Sciences (1980). Procedures for coupling such moieties to a molecule are well known in the art. The term "functional derivative" is intended to include the "fragments," "variants," "analogues," or "chemical derivatives" of a molecule.

Dosage

The dosage of the compositions can be dependent on the types of bile acids present in the composition. The dosage can also be determined based on the bile acid level(s) or bile acid profile(s) of the subject. The dosage can also be determined by the delay or lack of delay in a bile acid response to the activity, such as the ingestion of food or physical activity. In one embodiment, the dosage can be effective to modulate the bile acid level. In another embodiment, the dosage can be effective to increase the bile acid level. The dosage can further be determined by serum bile acid levels. In one embodiment, the dosage can increase a serum bile acid level. In another embodiment, the dosage can decrease a serum bile acid level. In an exemplary embodiment, the dosage can increase a serum bile acid level to a first level, decrease a serum bile acid level to a second level and increase a serum bile acid level to a third level. The first, second and third levels can be associated with the movement of bile acids in enterohepatic circulation and repeated cycles of enterohepatic circulation. The dosage can also be determined by a level of activation of a bile acid receptor. In yet another embodiment, the dosage can be effective to modulate bile acid receptor activation.

The dosage of the composition can include one or more bile acids and/or bile acid sequestrants at an individual concentration or a total concentration of about 0.001 mg/kg, 0.005 mg/kg, 0.01 mg/kg, 0.05 mg/kg, 0.1 mg/kg, 0.5 mg/kg, 1.0 mg/kg, 1.25 mg/kg, 1.5 mg/kg, 1.75 mg/kg, 2.0 mg/kg, 2.25 mg/kg, 2.5 mg/kg, 2.75 mg/kg, 3.0 mg/kg, 3.25 mg/kg, 3.5 mg/kg, 3.75 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.25 mg/kg, 9.5 mg/kg, 9.75 mg/kg, 10.0 mg/kg, 10.25 mg/kg, 10.5 mg/kg, 10.75 mg/kg, 11 mg/kg, 11.25 mg/kg, 11.5 mg/kg, 11.75 mg/kg, 12 mg/kg, 13 mg/kg, 14 mg/kg, 15 mg/kg, 16 mg/kg, 17 mg/kg, 18 mg/kg, 19 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, and any concentration in between. In one embodiment, the dosage of one or more bile acids and/or bile acid sequestrants at an individual concentration or a total concentration in the composition can be in the range of about 0.001 mg/kg to about 100 mg/kg. In another embodiment, the dosage of one or more bile acids and/or bile acid sequestrants at an individual concentration or a total concentration in the composition can be in the range of about 0.1 mg/kg to about 50 mg/kg. In yet another embodiment, the dosage of one or more bile acids and/or bile acid sequestrants at an individual concentration or a total concentration in the composition can be in the range of about 1 mg/kg to about 10 mg/kg. The term "dosage unit form" as used herein refers to physically discrete units suited as unitary dosages for the subjects to be treated, each unit containing a predetermined quantity of active compound calculated to produce the desired therapeutic effect in association with the required pharmaceutical carrier.

Dosage regimens may be adjusted to provide the optimum desired response (e.g., a therapeutic or prophylactic response). For example, a single bolus may be delivered, several divided doses may be delivered over time or the dose may be proportionally reduced or increased as indicated by the exigencies of the therapeutic situation. It is especially advantageous to formulate parenteral compositions in dosage unit form for ease of delivery and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of individuals.

A typical dosage of a composition when employed in the method according to the present invention can be in the range from about 0.001 to about 100 mg/kg body weight per day, from about 0.01 to about 50 mg/kg body weight per day, such as from about 0.05 to about 10 mg/kg body weight per day, delivered in one or more doses, such as from 1 to 3 doses. A typical unit dosage form intended for oral delivery one or more times per day, such as from one to three times per day, can suitably contain from about 0.05 to about 1000 mg, preferably from about 0.1 to about 500 mg, such as from about 0.5 to about 200 mg of the active compound. In an exemplary embodiment, the composition includes one or more of cholic acid, taurine conjugated bile acid, primary taurine conjugated bile acid, secondary taurine conjugated bile acid, and sulfated bile acid in the range of about 0.01 to about 50 mg/kg body weight per day, delivered in one to three doses. In another exemplary embodiment, the composition includes one or more of hypolipidemic agents, cholestryamine, colestipol, and colesevelam in the range of about 0.01 to about 50 mg/kg body weight per day, delivered in one to three doses. The exact dosage will depend upon the frequency and mode of delivery, the gender, age, weight and general condition of the subject treated, the nature and severity of the condition treated, any concomitant diseases to be treated and other factors evident to those skilled in the art.

Delivery

The bile acid composition can be delivered or administered by a variety of methods known in the art. The terms "delivery," "deliver," "administration" and "administer" are used interchangeable herein. As will be appreciated by the skilled artisan, the route and/or mode of delivery will vary depending upon the desired results. In an exemplary embodiment, the mode of delivery is parenteral (e.g., intravenous, subcutaneous, intraperitoneal, intramuscular). In one embodiment, the bile acid composition is delivered by intravenous infusion or injection. In another embodiment, the bile acid composition is delivered by intramuscular or subcutaneous injection. In another embodiment, the bile acid composition is delivered perorally. In yet another embodiment, the bile acid composition is delivered orally. Yet another mode of delivery can include methods and combinations for delivery to the gut.

The bile acid composition can be delivered before the ingestion of food, pre-prandial, and/or after the ingestion of food, post-prandial. Delivery of the bile acid composition both pre-prandial and post-prandial can be therapeutic. In an exemplary embodiment, the bile acid composition can be delivered before, during, and/or after a meal. In one embodiment, the bile acid composition can be delivered before, during, and/or after a fasting or non-meal period. The non-meal period can be after a last meal of a day and before breaking a fast of a second or next day. In another embodiment, the bile acid composition can be delivered before, with, and/or after the first meal of the day. In yet another embodiment, the bile acid composition can be delivered before, with, and/or after the last meal of the day. In another embodiment, the bile acid composition can be delivered at least about 0 mins, 5 mins, 10 mins, 15 mins, 20 mins, 25 mins, 30 mins, 35 mins, 40 mins, 45 mins, 50 mins, 55 mins, 1 hr, 1.5 hrs, 2 hrs, 2.5 hrs, 3 hrs, 3.5 hrs, 4 hrs, 4.5 hrs, 5 hrs, 5.5 hrs, 6 hrs, 6.5 hrs, 7 hrs, 7.5 hrs, 8 hrs, 8.5 hrs, 9 hrs, 9.5 hrs, 10 hrs, 11 hrs, 12 hrs, before, and/or after a meal. In an exemplary embodiment, the bile acid composition can be delivered within about 3 hrs of a meal.

In one embodiment, the bile acid composition can be delivered before, during, and/or after a period of physical activity. In another embodiment, the bile acid composition can be delivered at least about 0 mins, 5 mins, 10 mins, 15 mins, 20 mins, 25 mins, 30 mins, 35 mins, 40 mins, 45 mins, 50 mins, 55 mins, 1 hr, 1.5 hrs, 2 hrs, 2.5 hrs, 3 hrs, 3.5 hrs, 4 hrs, 4.5 hrs, 5 hrs, 5.5 hrs, 6 hrs, 6.5 hrs, 7 hrs, 7.5 hrs, 8 hrs, 8.5 hrs, 9 hrs, 9.5 hrs, 10 hrs, 11 hrs, 12 hrs, before, and/or after a period of physical activity.

The bile acid composition can be delivered to modulate serum bile acid levels. In one embodiment, the bile acid composition can be delivered to increase a serum bile acid level. In another embodiment, the bile acid composition can be delivered to decrease a serum bile acid level. In an exemplary embodiment, the bile acid composition can be delivered to increase a serum bile acid level to a first level, decrease a serum bile acid level to a second level and increase a serum bile acid level to a third level. The first, second and third levels can be associated with the movement of bile acids in enterohepatic circulation and repeated cycles of enterohepatic circulation.

Delivery of the bile acid composition can also be repeated one or more times. The repeated delivery of the bile acid composition can also be one or more times before, during, and/or after a therapeutic intervention. The repeated delivery can further be in a manner similar to the initial delivery. The repeated delivery can be before, during, and/or after the first meal of the day. In one embodiment, the repeated delivery can be before, during, and/or after the last meal of the day. In another embodiment, the repeated delivery can be before, during, and/or after a fasting or non-meal period. The non-meal period can be after a last meal of a day and before breaking a fast of a second or next day. In another embodiment, the repeated delivery can be at least about 0 mins, 5 mins, 10 mins, 15 mins, 20 mins, 25 mins, 30 mins, 35 mins, 40 mins, 45 mins, 50 mins, 55 mins, 1 hr, 1.5 hrs, 2 hrs, 2.5 hrs, 3 hrs, 3.5 hrs, 4 hrs, 4.5 hrs, 5 hrs, 5.5 hrs, 6 hrs, 6.5 hrs, 7 hrs, 7.5 hrs, 8 hrs, 8.5 hrs, 9 hrs, 9.5 hrs, 10 hrs, 11 hrs, 12 hrs, before, and/or after a meal. In an exemplary embodiment, the composition can be delivered to a subject with a meal and an additional dosage of the composition is delivered during a non-meal period.

Delivery of the bile acid composition can also be repeated one or more times before, during, and/or after a period of activity. In one embodiment, the repeated delivery can be at least about 0 mins, 5 mins, 10 mins, 15 mins, 20 mins, 25 mins, 30 mins, 35 mins, 40 mins, 45 mins, 50 mins, 55 mins, 1 hr, 1.5 hrs, 2 hrs, 2.5 hrs, 3 hrs, 3.5 hrs, 4 hrs, 4.5 hrs, 5 hrs, 5.5 hrs, 6 hrs, 6.5 hrs, 7 hrs, 7.5 hrs, 8 hrs, 8.5 hrs, 9 hrs, 9.5 hrs, 10 hrs, 11 hrs, 12 hrs, before, and/or after a period of activity.

Delivery of the bile acid composition can be targeted to one or more regions in a subject. The regions can include but are not limited to a circulatory system, a enterohepatic circulation, a portal circulation, a gastrointestinal tract. In an exemplary embodiment, the delivery is targeted to a circulatory system, a portal circulation, and a gastrointestinal tract. The delivery can also be targeted to one or more tissues in a subject. The tissues can include, a gall bladder, an intestine, a brown adipocyte, a beige (or brown-like) adipocyte, a muscle and a liver.

The composition can also be delivered by a system that is on the skin or that can be at least partially implantable. The implantable system can be any of those known and used in the art. The system can include a programmable pump such as those commonly used to deliver insulin to a diabetic patient. One or more of these components may be modular and connected to a transcutaneous delivery means which may include a port, needle, patch, or the like. In an exemplary embodiment, the implantable system includes a reservoir and a port. The reservoir may include a refillable or reloadable container for holding the cocktail. In another embodiment, the system can include a catheter. In another embodiment, the implantable system is a translumenal cathether. The system can include one or more subsystems for determining a specific event (e.g., a meal, a time, a physical activity, etc.) that may initiate a treatment algorithm described herein. In an exemplary embodiment, the subsystem is a meal detection system that measures at least a heart rate variability in a subject. An exemplary subsystem is disclosed in U.S. application Ser. No. 12/980,695 entitled "OBESITY THERAPY AND HEART RATE VARIABILITY" filed on Dec. 29, 2010, the contents of which are hereby incorporated by reference in their entirety. The system can also be configured to deliver the composition at a prescribed dosage and/or a prescribed interval. The prescribed dosage and/or prescribed interval can be determined as described herein.

One skilled in the art will appreciate further features and advantages of the invention based on the above-described embodiments. Accordingly, the invention is not to be limited by what has been particularly shown and described in the examples or figures, except as indicated by the appended claims. All publications and references cited herein are expressly incorporated herein by reference in their entirety.

EXPERIMENTAL DATA

Example 1

Bile Acid Measurements

Plasma sampling was performed on 16 obese human subjects and 8 gender- and age-matched normal weight controls. Table 1 shows the assessment of food intake for 4 days and assessment of physical activity for 3 days that was measured for each individual to establish a baseline of intake and energy expenditure.

TABLE 1

Subjects' Activity Measurements

|  | MEN | | WOMEN | |
| --- | --- | --- | --- | --- |
|  | OBESE | LEAN | OBESE | LEAN |
| N | 10 | 4 | 6 | 4 |
| AGE* (Years) | 43.5 | 36.5 | 45.7 | 45.5 |
| BMI (kg/m$^2$) | 44.2 | 22.6 | 38.7 | 20.8 |
| Activity* (kcal/kg) | 43.5 | 46.9 | 37.1 | 45.0 |
| Intake (kcal) | 2255 | 2775 | 1862 | 1926 |

*p > 0.05

In the limited cohort tested, the post-prandial bile acid responses appeared to be gender dependent. Post-prandial bile acid levels measured in lean men demonstrated well defined peaks and cycling of increases and decreases of bile acid levels. See FIG. 2. In contrast, obese men demonstrated blunted post-prandial bile acid levels with delayed increases and decreased cycling of bile acid levels. Bile acid conjugation also was decreased in obese men after food intake (FIGS. 4A and 4B).

Figure 6A:
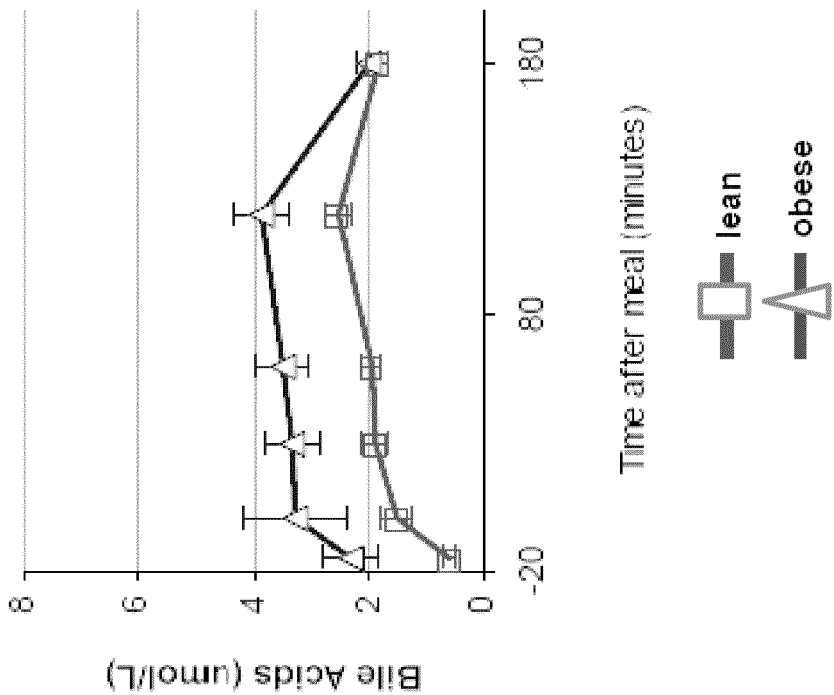
FIG. 6A shows a graph of unconjugated bile acids present in serum for lean and obese women in relation to a meal.
Figure 6B:
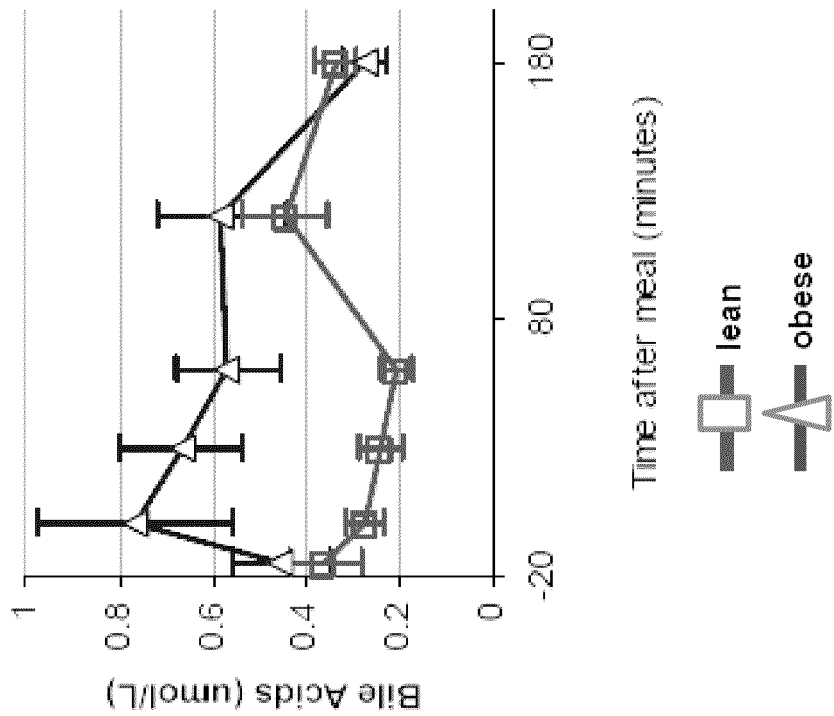
FIG. 6B shows a graph of conjugated bile acids present in serum for lean and obese women in relation to a meal.
Figure 7B:
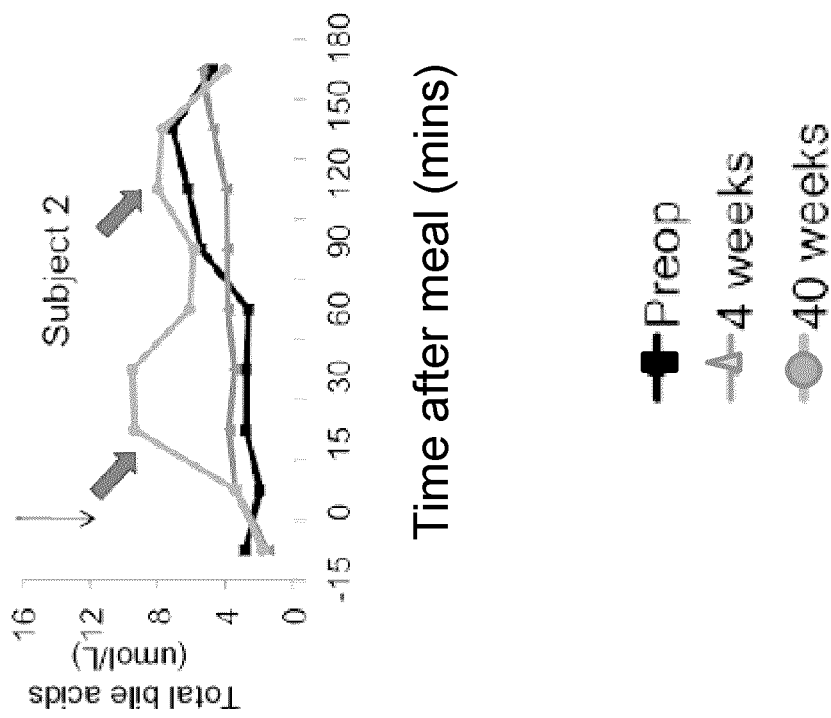
FIG. 7B shows a graph of total bile acids present in serum of Subject 2 preoperative 4 weeks postoperative and 40 weeks postoperative in relation to a meal.
Figure 7A:
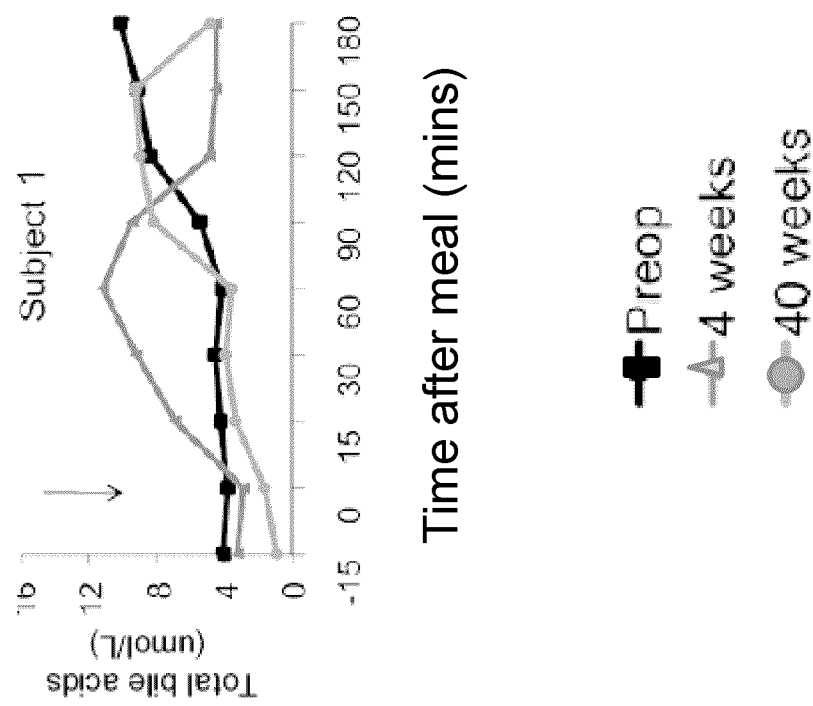
FIG. 7A shows a graph of total bile acids present in serum of Subject 1 preoperative 4 weeks postoperative and 40 weeks postoperative in relation to a meal.
Figure 7D:
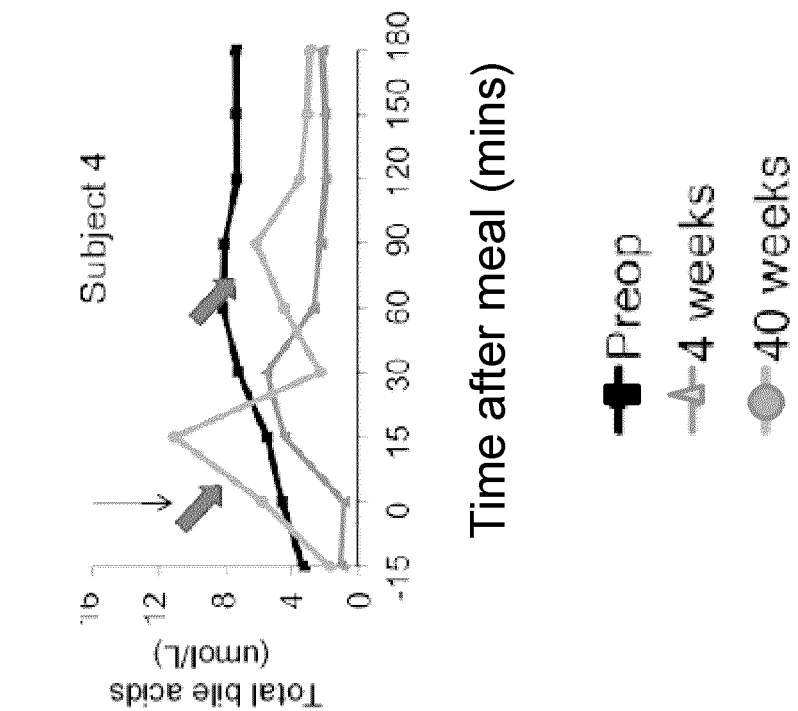
FIG. 7D shows a graph of total bile acids present in serum of Subject 4 preoperative 4 weeks postoperative and 40 weeks postoperative in relation to a meal.
Figure 7C:
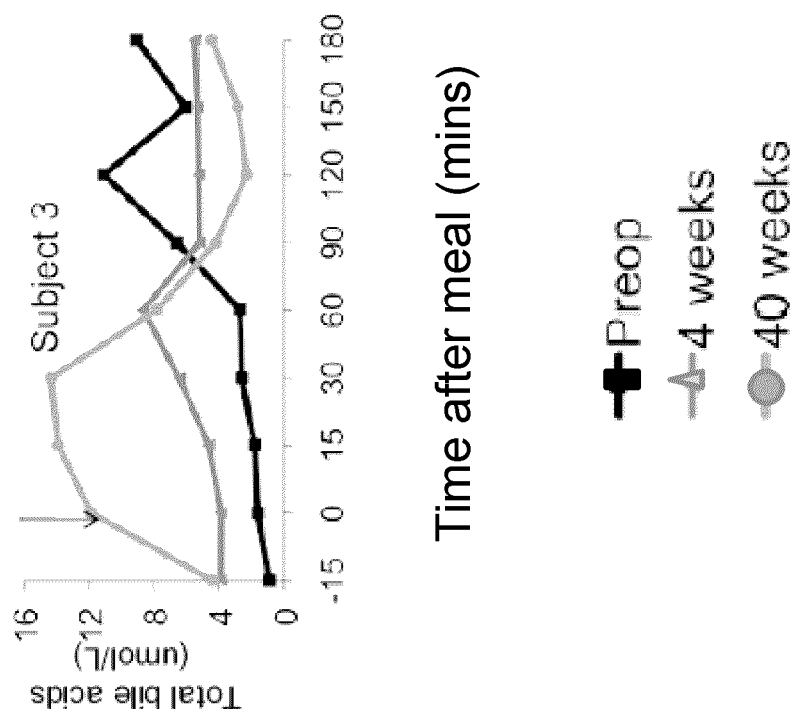
FIG. 7C shows a graph of total bile acids present in serum of Subject 3 preoperative 4 weeks postoperative and 40 weeks postoperative in relation to a meal.

In the female cohort, post-prandial bile acid levels appeared to lack well defined peaks and cycling of increases and decreases in bile acid levels for both lean and obese women (FIG. 5). However, conjugated bile acid levels also failed to demonstrate well defined peaks and cycling in both lean and obese women after food intake (FIGS. 6A and 6B).

Example 2

Surgical Intervention and Bile Acid Levels

To determine whether Roux-en-Y gastric bypass (RYGB) induces changes in the circulating concentrations of bile acids, total serum bile acids were determined in obese subjects. Five subjects were given a liquid meal after an overnight 8 hour fast. The meal was taken slowly over 20 minutes and consisted of 8 oz, approximately 450 calories, 40% carbohydrate, 40% fat, and 20% protein. Serum bile acid measurements were taken 15 minutes prior to meal ingestion, at the end of meal ingestion (time 0), and 15, 30, 60, 90, 120, 150 and 180 minutes after ingestion. Measurements were repeated prior to RYGB procedure, 4 weeks post procedure and 40 weeks post procedure. FIGS. 7A-7E show that total serum bile acid levels were abnormal in obese individuals prior to surgery and surgery normalizes the bile acid response to food ingestion.

Figure 8:
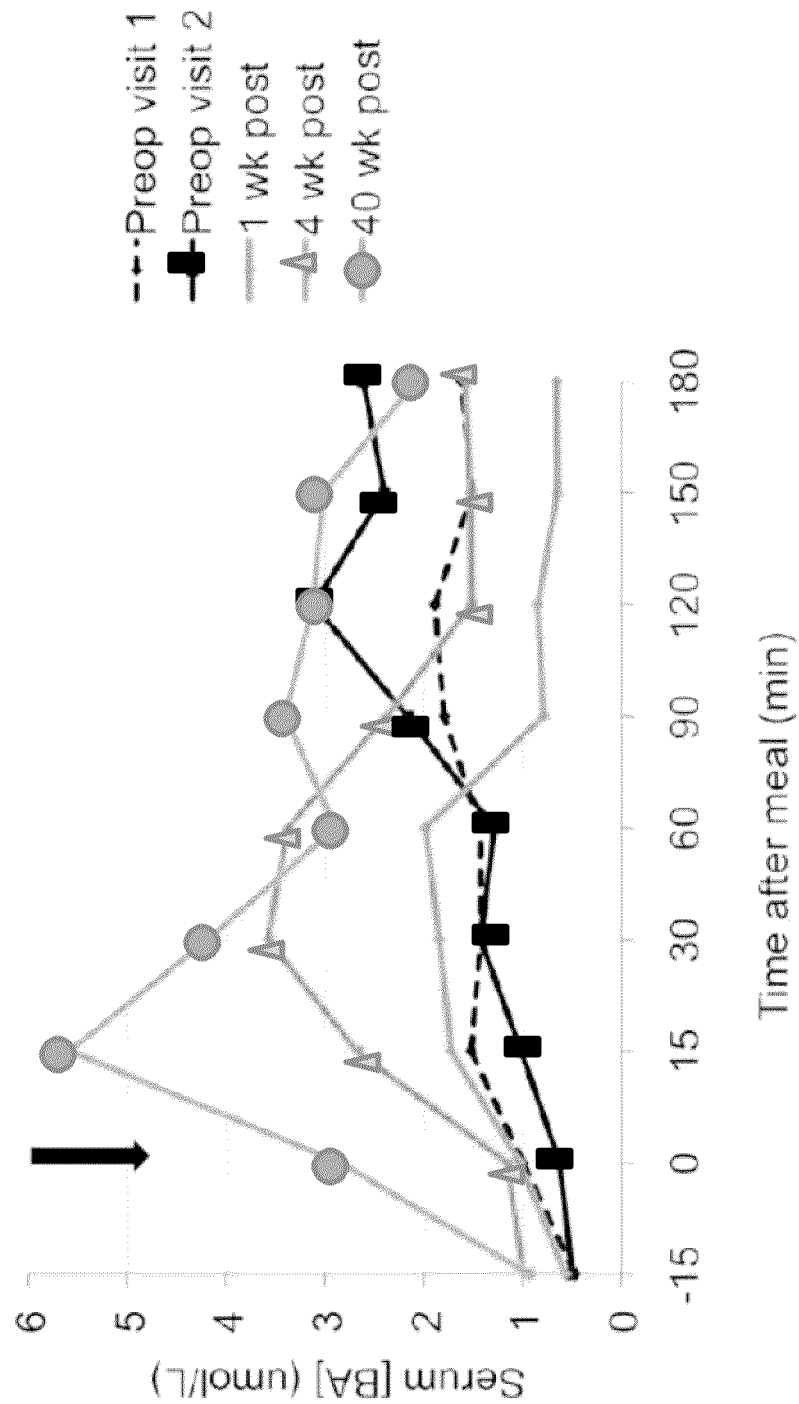
FIG. 8 shows a graph of primary conjugated bile acids present in serum of lean men preoperative visit 1, preoperative visit 2, 1 week postoperative, 4 weeks postoperative and 40 weeks postoperative in relation to a meal.
Figure 9:
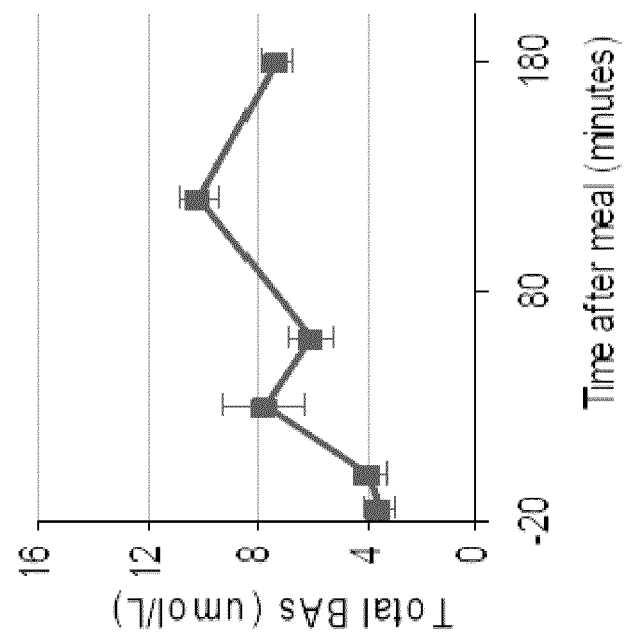
FIG. 9 shows a graph of total bile acids present in serum in lean men in relation to a meal.

To determine whether individuals that have undergone surgical intervention demonstrate variances in bile acid level, the 5 subjects underwent RYGB procedures. Each individual bile acid levels was measured twice prior to surgical intervention and at 1 week post, 4 weeks post and 40 weeks post surgery. Similar to the tests described above, individuals were given a liquid meal after an overnight 8 hour fast. The meal was taken slowly over 20 minutes and consisted of 8 oz, approximately 450 calories, 40% carbohydrate, 40% fat, and 20% protein. Serum bile acid measurements were taken 15 minutes prior to meal ingestion, at the end of meal ingestion (time 0), and 15, 30, 60, 90, 120, 150 and 180 minutes after ingestion. FIG. 8 shows that primary conjugated bile acid levels in response to food ingestion were elevated and accelerated in individuals post surgery. In fact, the bile acid levels of obese men that had undergone RYGB surgery demonstrated well defined cycling of increased and decreased levels of conjugated bile acids after meals, similar to lean men as seen in FIG. 9. The data demonstrated that RYGB appeared to accelerate postprandial response of primary conjugated bile acids.

Figure 10:
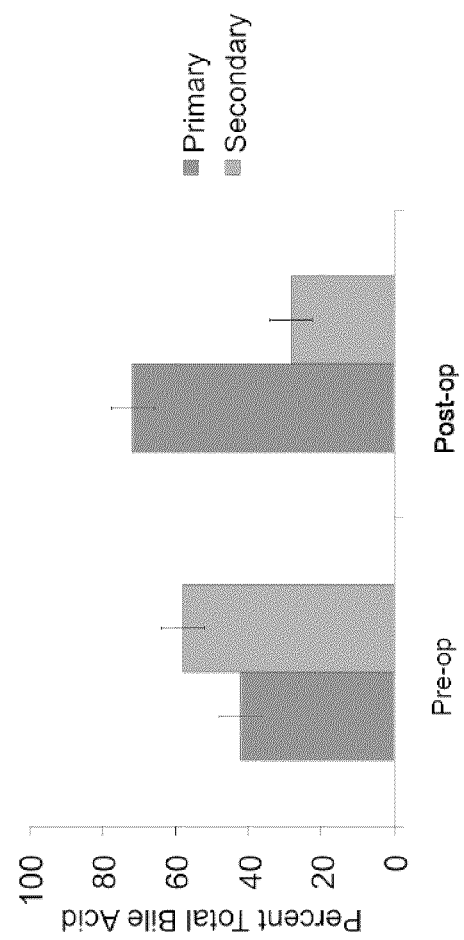
FIG. 10 shows a bar graph of the percent of primary and secondary bile acids in total bile acids present in serum of obese individuals preoperative and postoperative.
Figure 11:
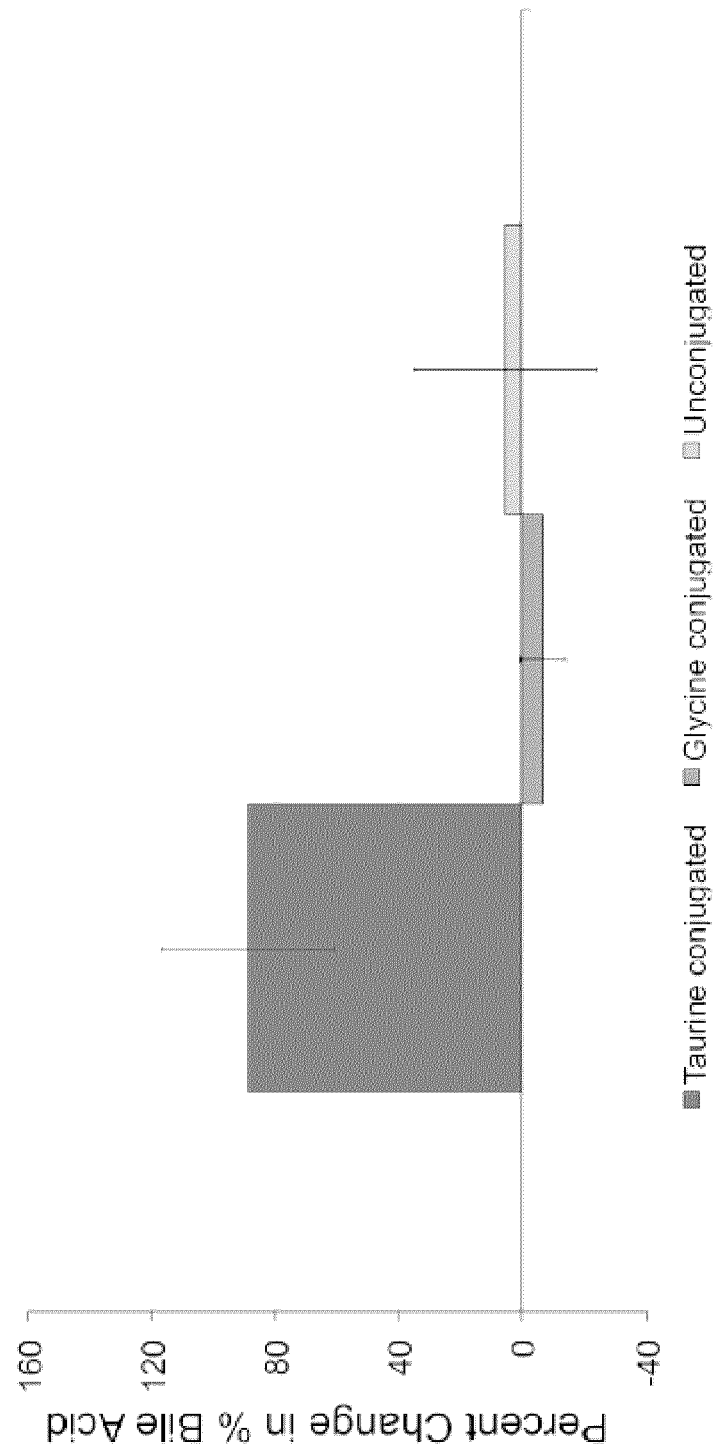
FIG. 11 shows a bar graph of the percent change of taurine conjugated, glycine conjugated and unconjugated bile acids in serum of obese men 4 weeks postoperative.
Figure 12:
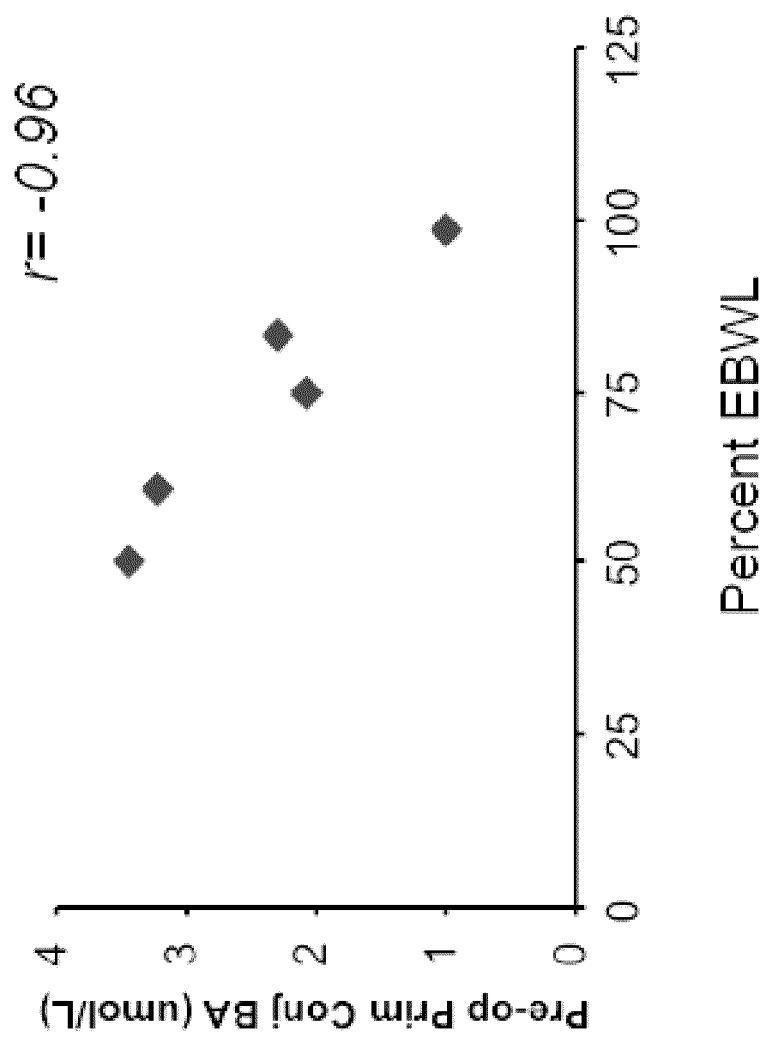
FIG. 12 shows a scatter plot of the pre-operative bile acid levels and the percent of excess body weight loss (EBWL) in obese individuals.
Figure 13:
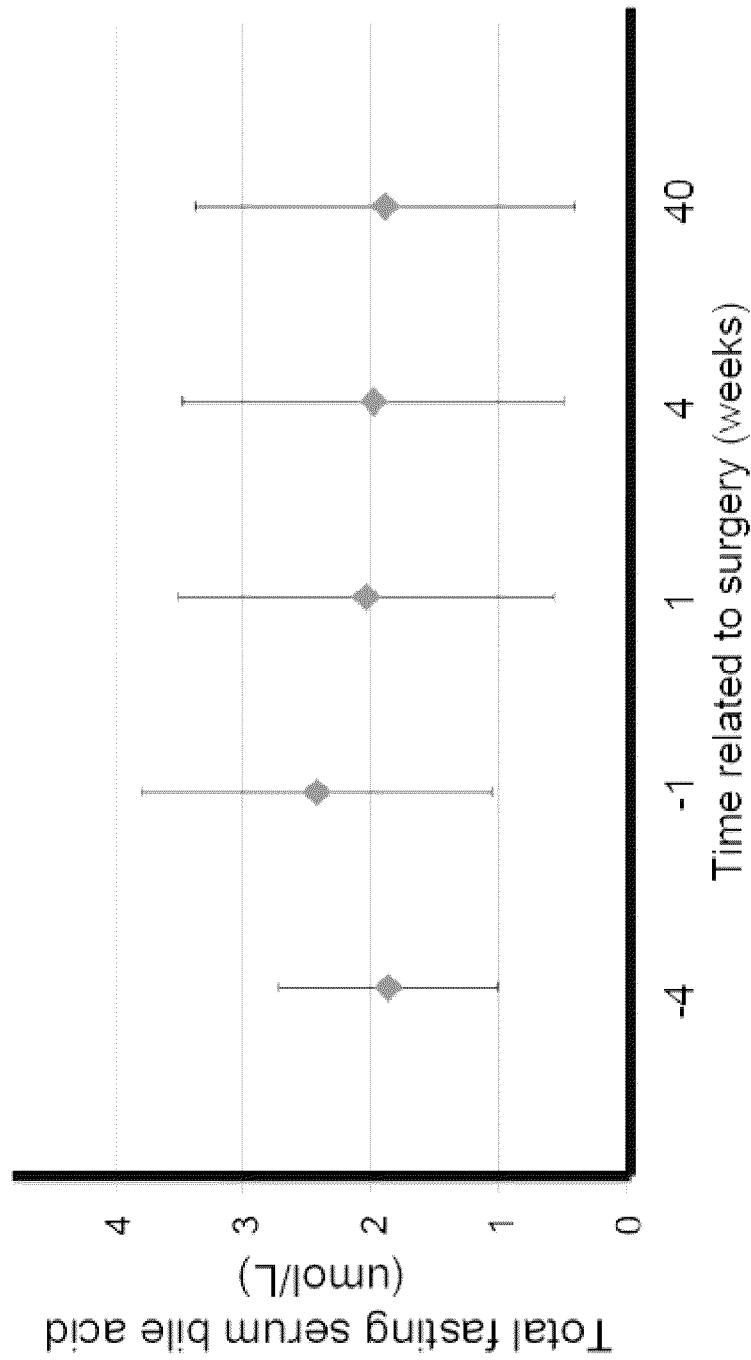
FIG. 13 shows a graph of the total fasting bile acid levels in obese individuals pre- and post-Roux-en-Y gastric bypass (RYGB), at 4 weeks preoperative, 1 week preoperative, 1 week postoperative, 4 weeks postoperative and 40 weeks postoperative.

Moreover, surgical intervention lead to increased primary to secondary bile acid ratios. See FIG. 10. Primary and secondary bile acids and their taurine and glycine conjugates were measured using reverse phase HPLC/MS. Prior to surgery, measurements indicated individuals had a higher percentage of secondary bile acids than primary bile acids. After surgery, the greatest change in percentage of bile acids was observed in the taurine conjugated bile acids (FIG. 11). Interestingly, a correlation was seen between pre-operative bile acid levels and weight loss outcome after RYGB (FIG. 12). Individuals with lower pre-operative primary conjugated bile acid levels had a greater percent weight loss after surgery than individuals with high pre-operative primary conjugated bile acid levels. Based on these findings, it is conceived that a measurement of pre-operative bile acid levels may be used as a predictor of weight loss outcomes following RYGB. Individuals demonstrated little change in their fasting serum bile acid levels from 4 weeks pre-operative to 40 weeks after RYGB (FIG. 13).

Figure 14:
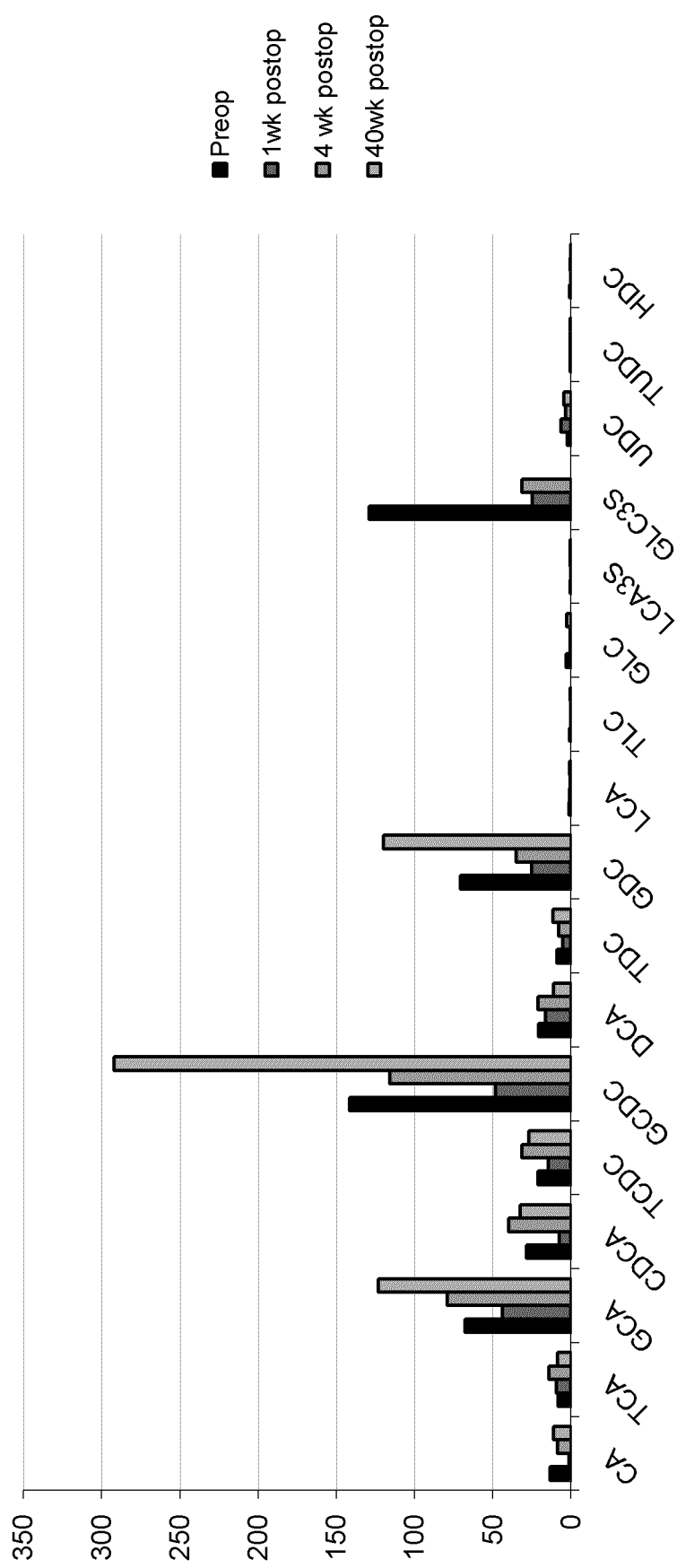
FIG. 14 shows a graph of post-prandial area-under-the-curve (AUC) analysis of individual bile acids before RYGB and 1 week, 4 weeks and 40 weeks after RYGB.

Post-prandial area-under-the-curve (AUC) analysis was conducted to assess the individual bile acids before and after RYGB. Analysis was performed on patients preoperative and 1 week, 4 weeks and 40 weeks after RYGB (FIG. 14). AUC was calculated using the trapezoidal method. Statistical analyses were performed using SPSS, version 18 (IBM, Armonk, N.Y.). A $p<0.05$ was considered significant. Data are depicted as mean+/−standard error of the mean (s.e.m.).

Example 3

Individual Bile Acid Measurements

Circulating concentrations of individual bile acids were measured in lean and obese individuals. More than a dozen types of bile acids are known, such as cholic acid, chenodeoxycholic acid, deoxycholic acid, lithocholic acid, and ursodeoxycholic acid, as well as their taurine or glycine conjugated forms.

Figure 15:
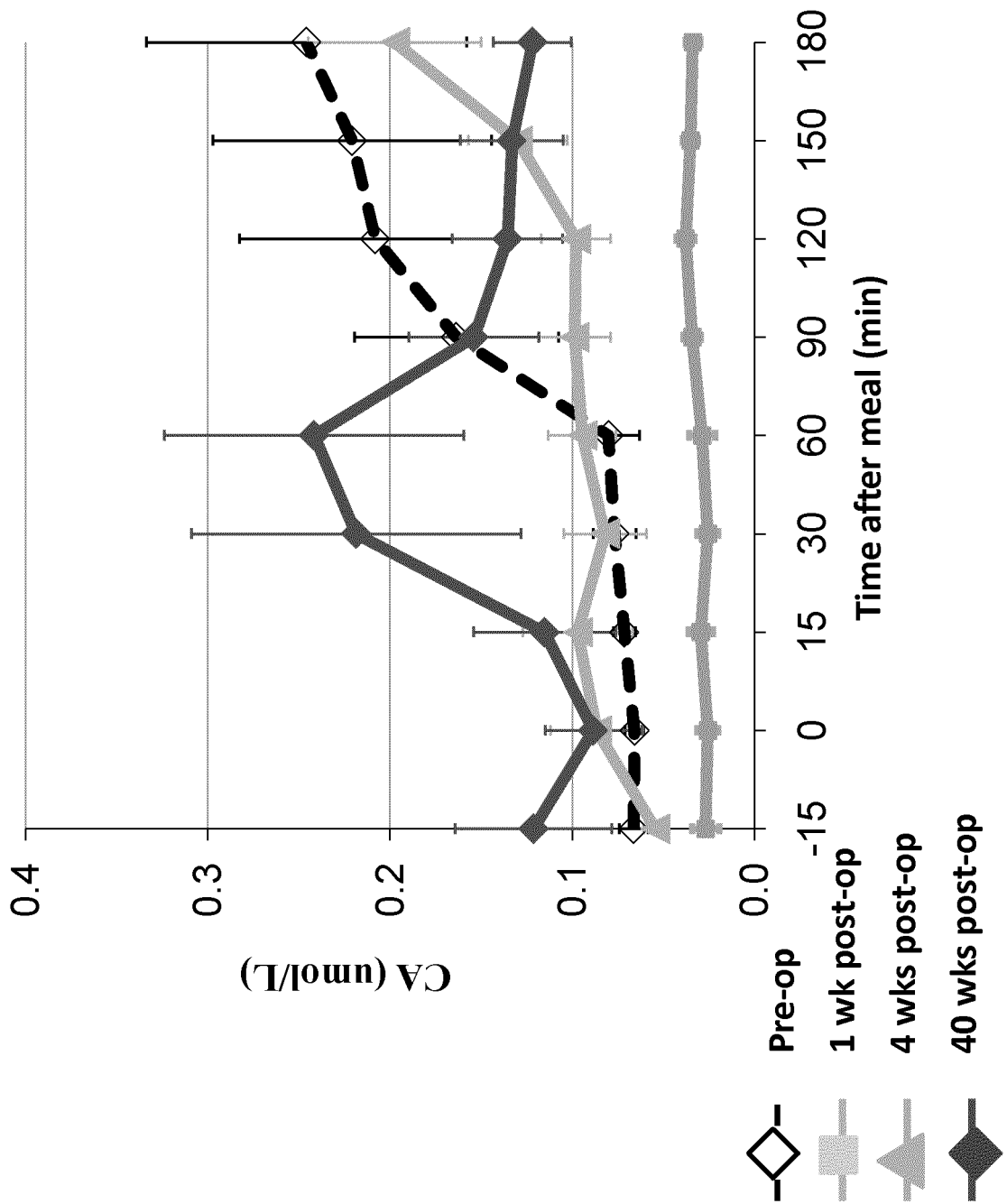
FIG. 15 shows a graph of cholic acid (CA) present in serum of obese individuals preoperative, 1 week postoperative, 4 weeks postoperative and 40 weeks postoperative in relation to a meal.
Figure 16:
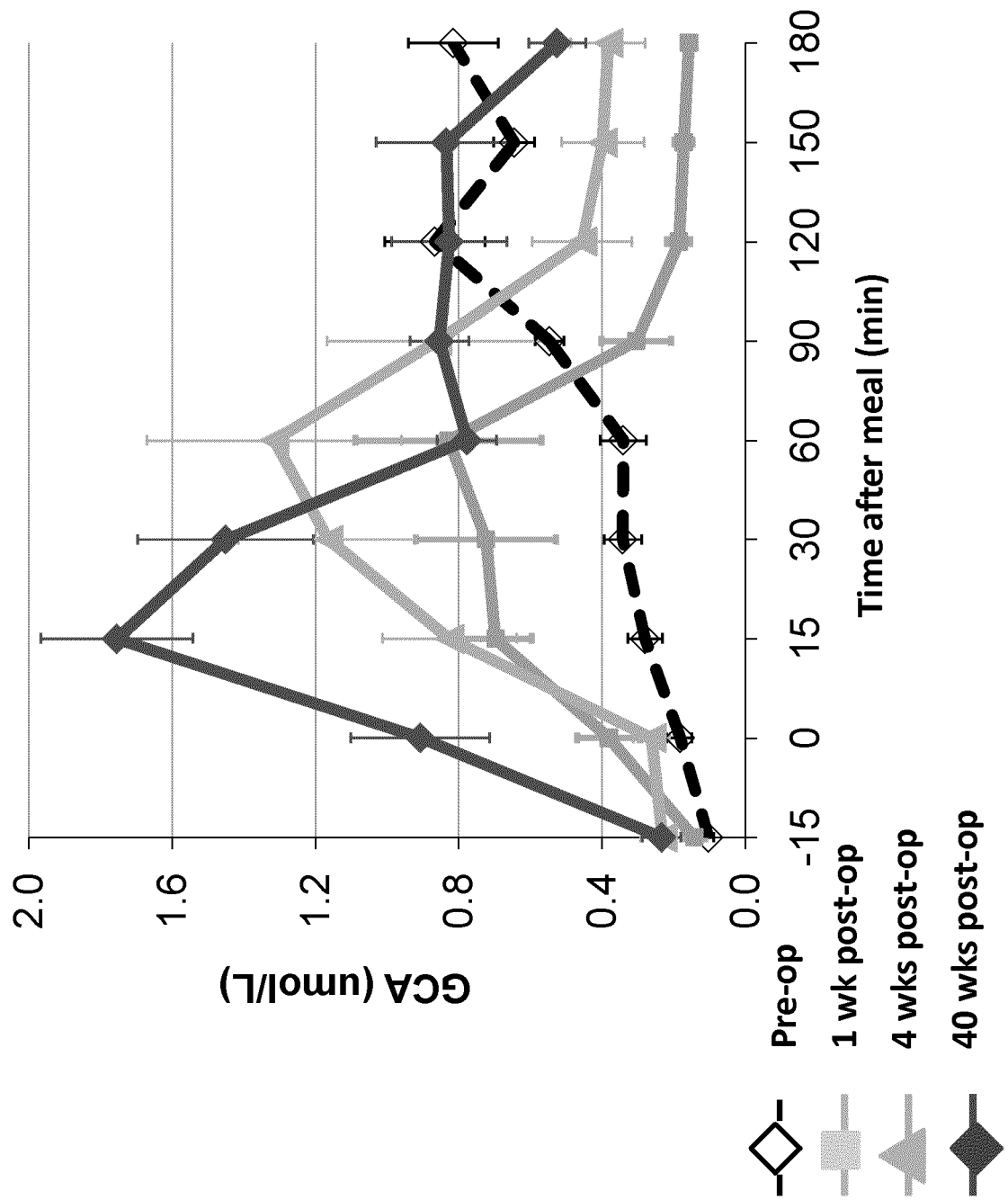
FIG. 16 shows a graph of glycocholic acid (GCA) present in serum of obese individuals preoperative, 1 week postoperative, 4 weeks postoperative and 40 weeks postoperative in relation to a meal.
Figure 17:
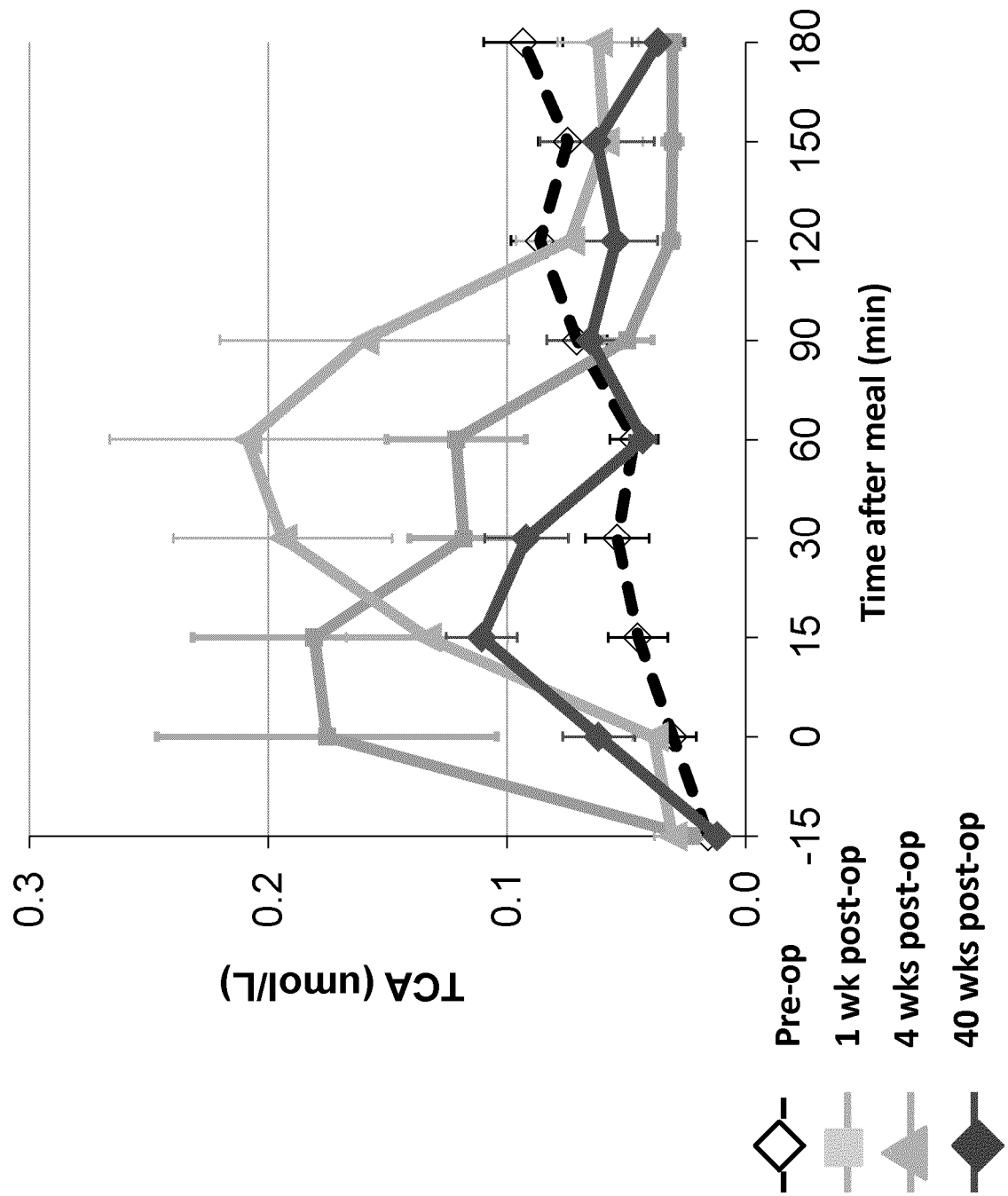
FIG. 17 shows a graph of taurine cholic acid (TCA) present in serum of obese individuals preoperative, 1 week postoperative, 4 weeks postoperative and 40 weeks postoperative in relation to a meal.
Figure 18:
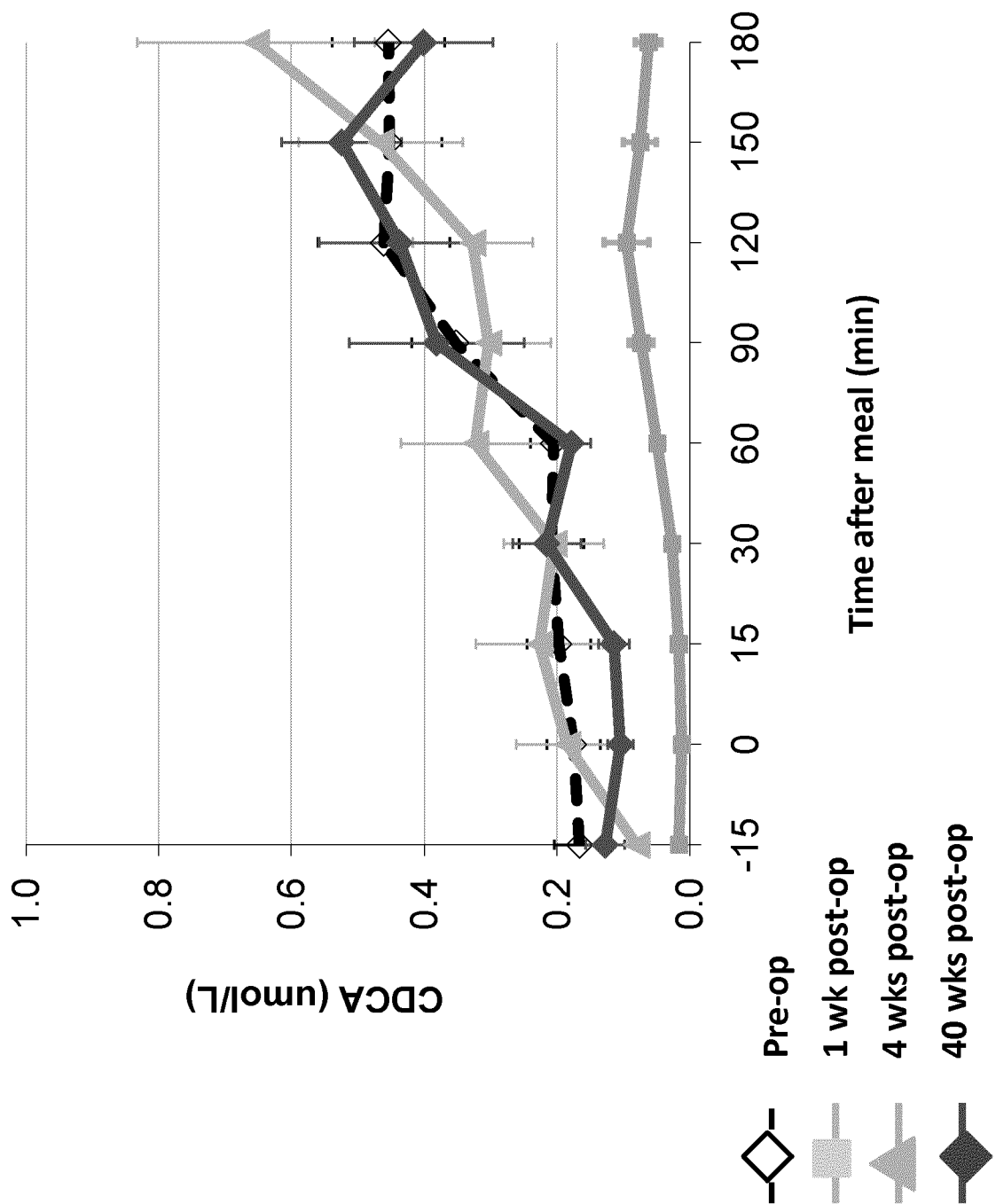
FIG. 18 shows a graph of chenodeoxycholic acid (CDCA) present in serum of obese individuals preoperative, 1 week postoperative, 4 weeks postoperative and 40 weeks postoperative in relation to a meal.
Figure 19:
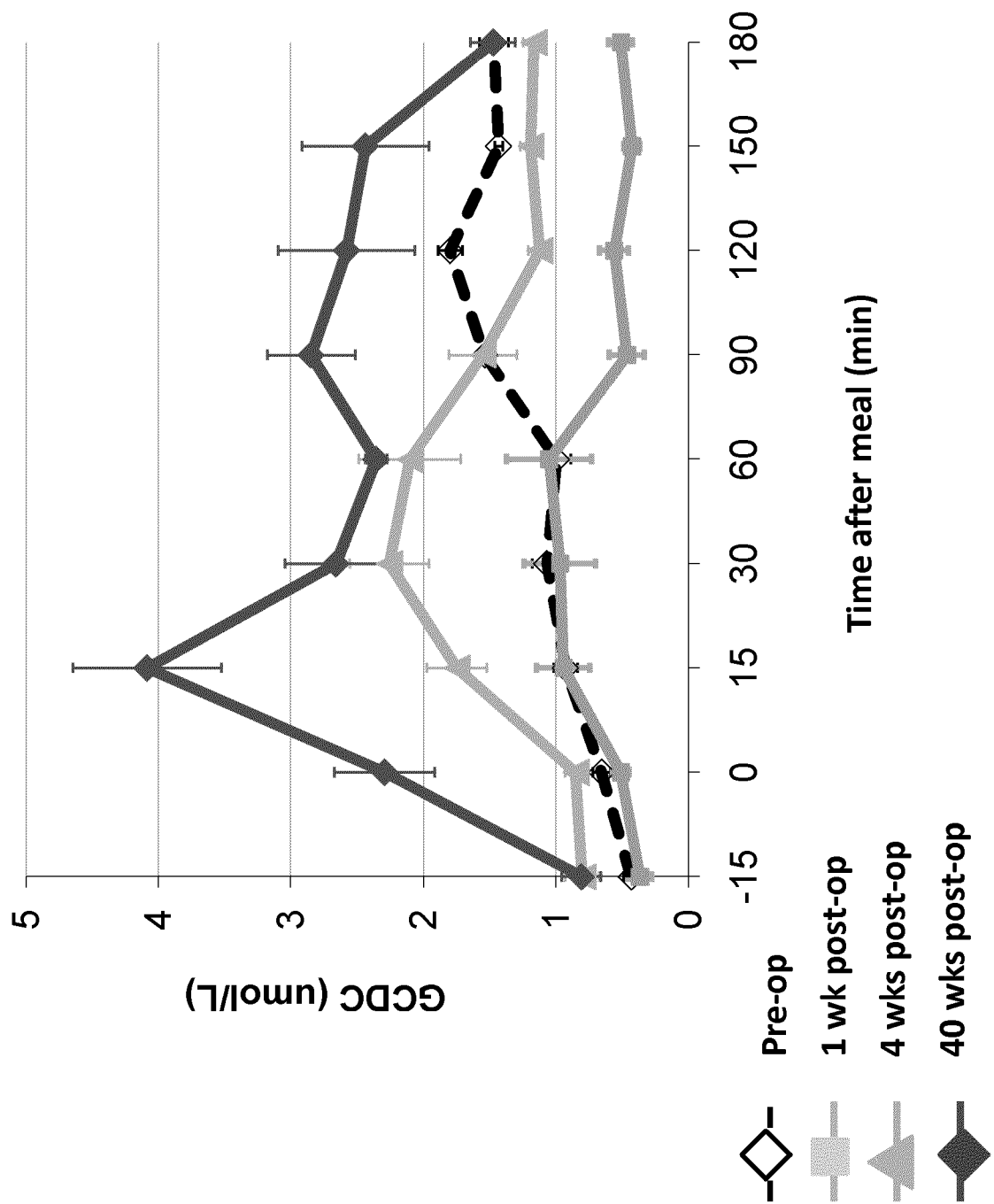
FIG. 19 shows a graph of glycine chenodeoxycholic acid (GCDC) present in serum of obese individuals preoperative, 1 week postoperative, 4 weeks postoperative and 40 weeks postoperative in relation to a meal.
Figure 20:
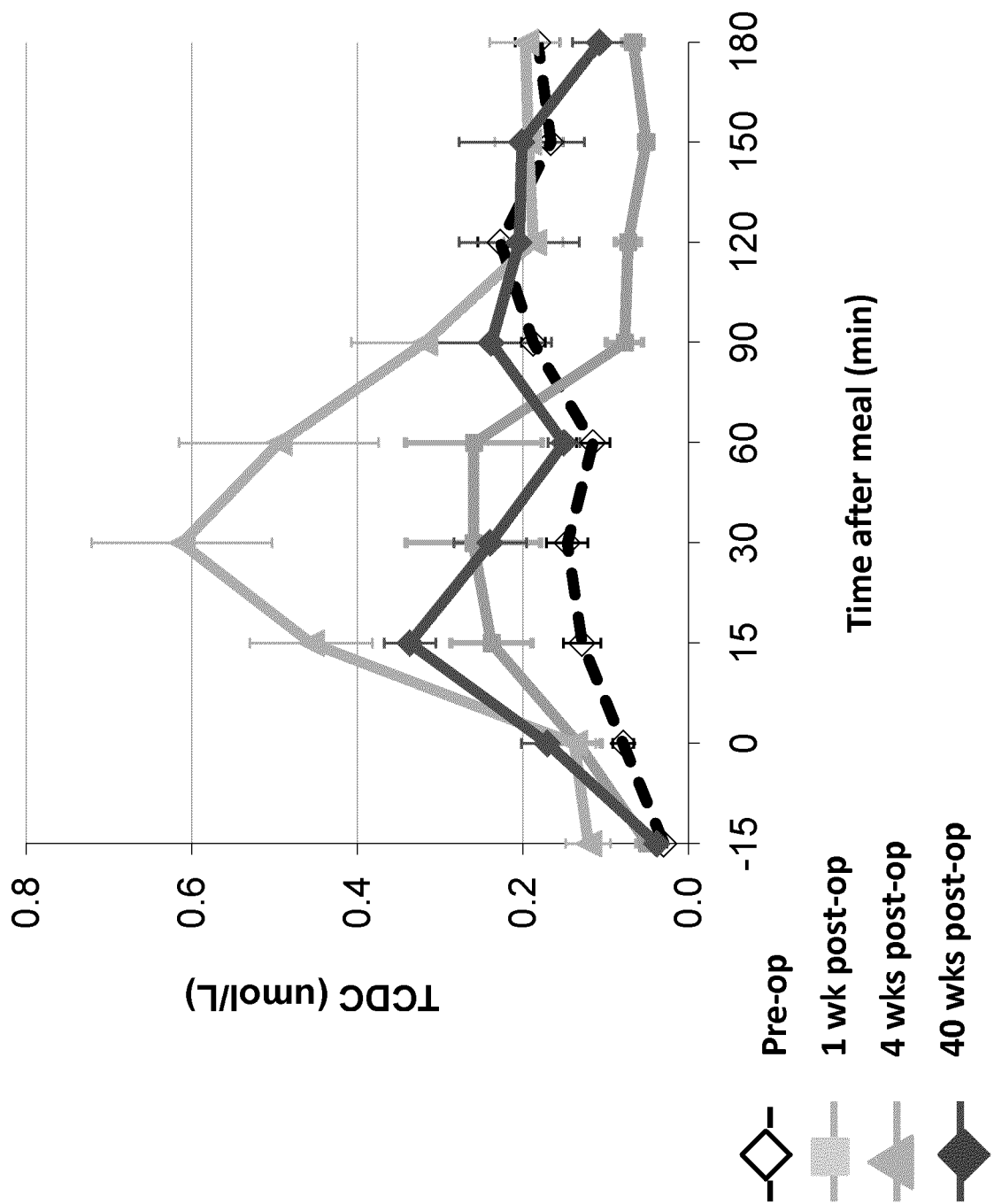
FIG. 20 shows a graph of taurine chenodeoxycholic acid (TCDC) present in serum of obese individuals preoperative, 1 week postoperative, 4 weeks postoperative and 40 weeks postoperative in relation to a meal.
Figure 21:
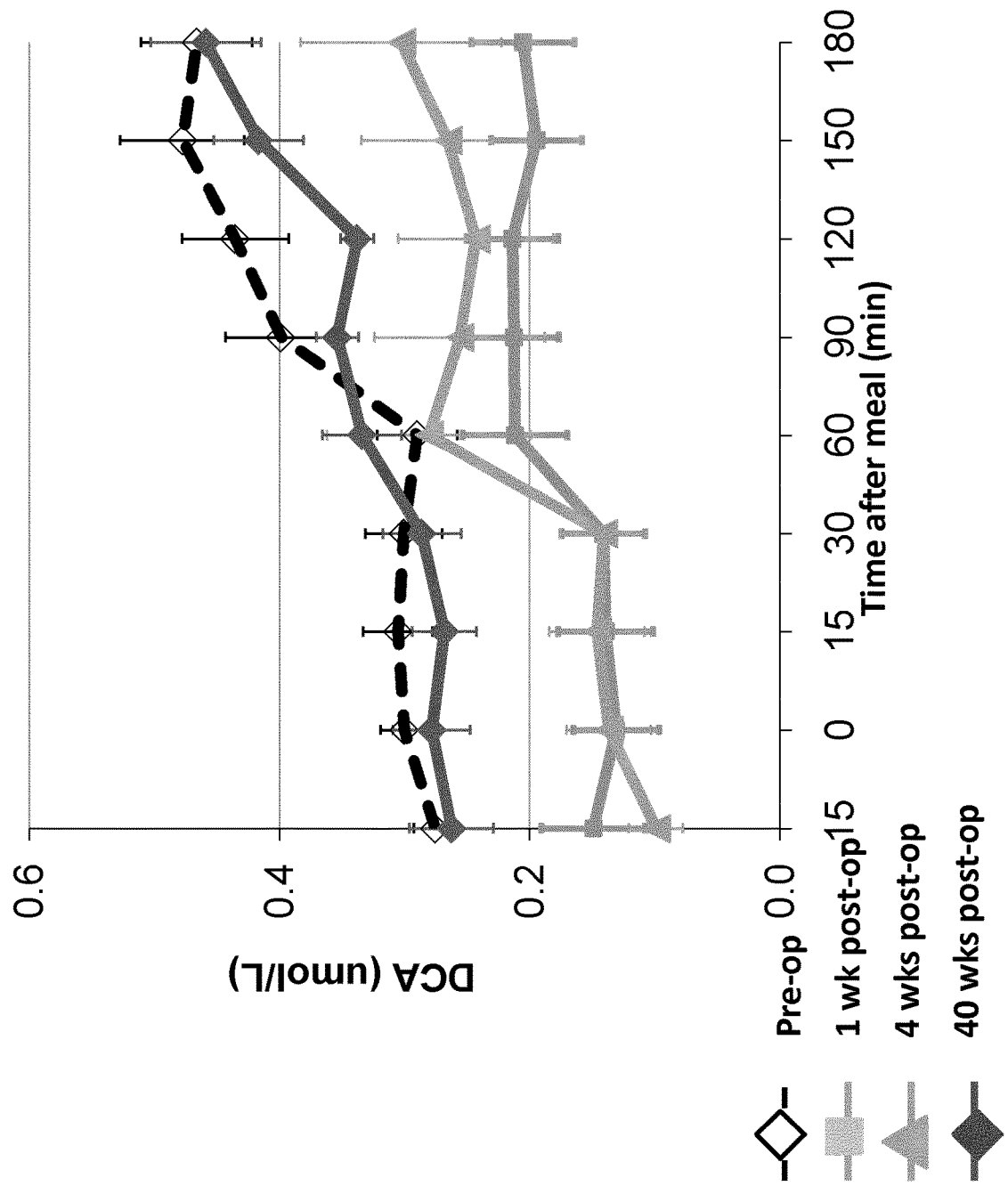
FIG. 21 shows a graph of deoxycholic acid (DCA) present in serum of obese individuals preoperative, 1 week postoperative, 4 weeks postoperative and 40 weeks postoperative in relation to a meal.
Figure 22:
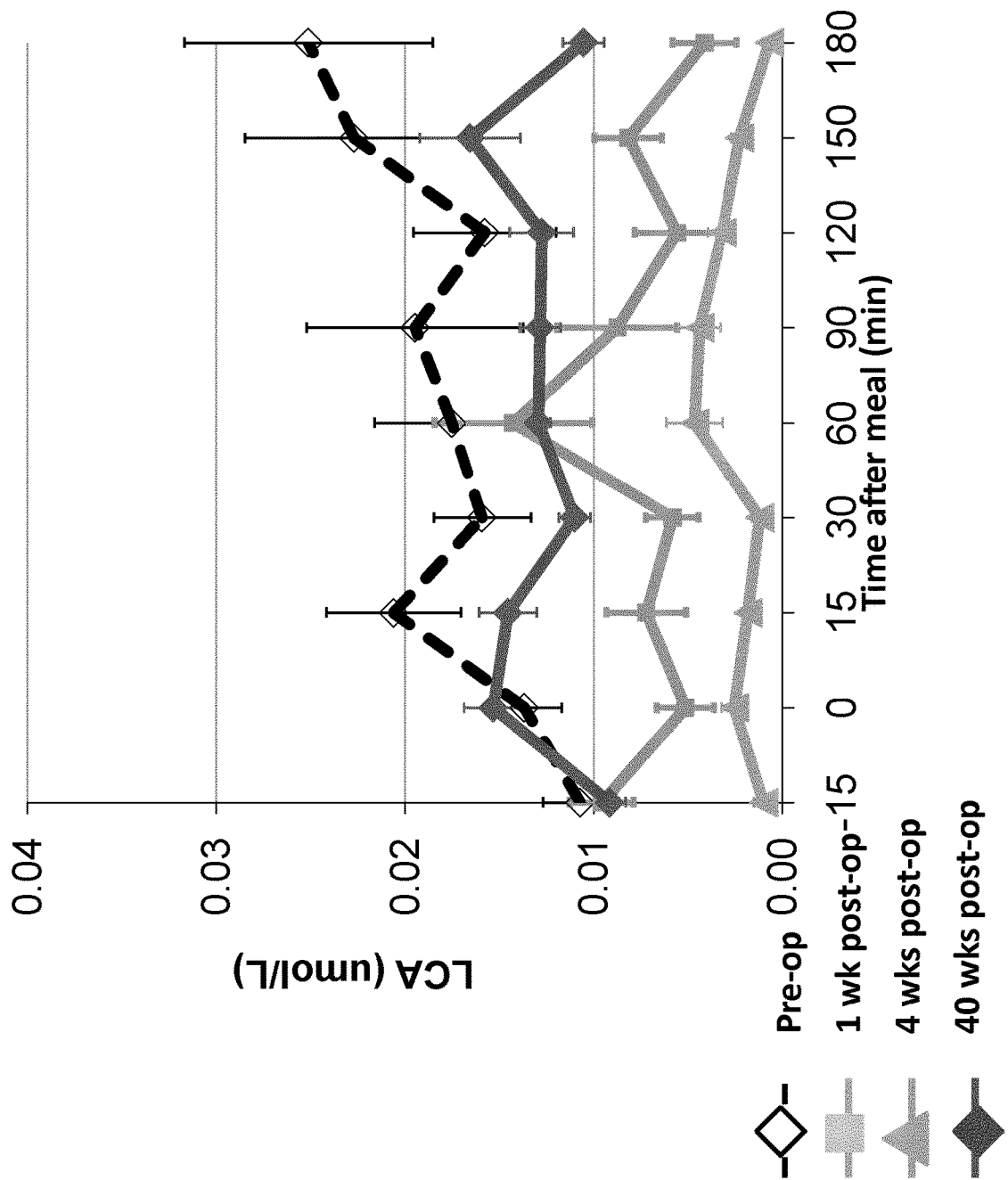
FIG. 22 shows a graph of lithocholic acid (LCA) present in serum of obese individuals preoperative, 1 week postoperative, 4 weeks postoperative and 40 weeks postoperative in relation to a meal.
Figure 23:
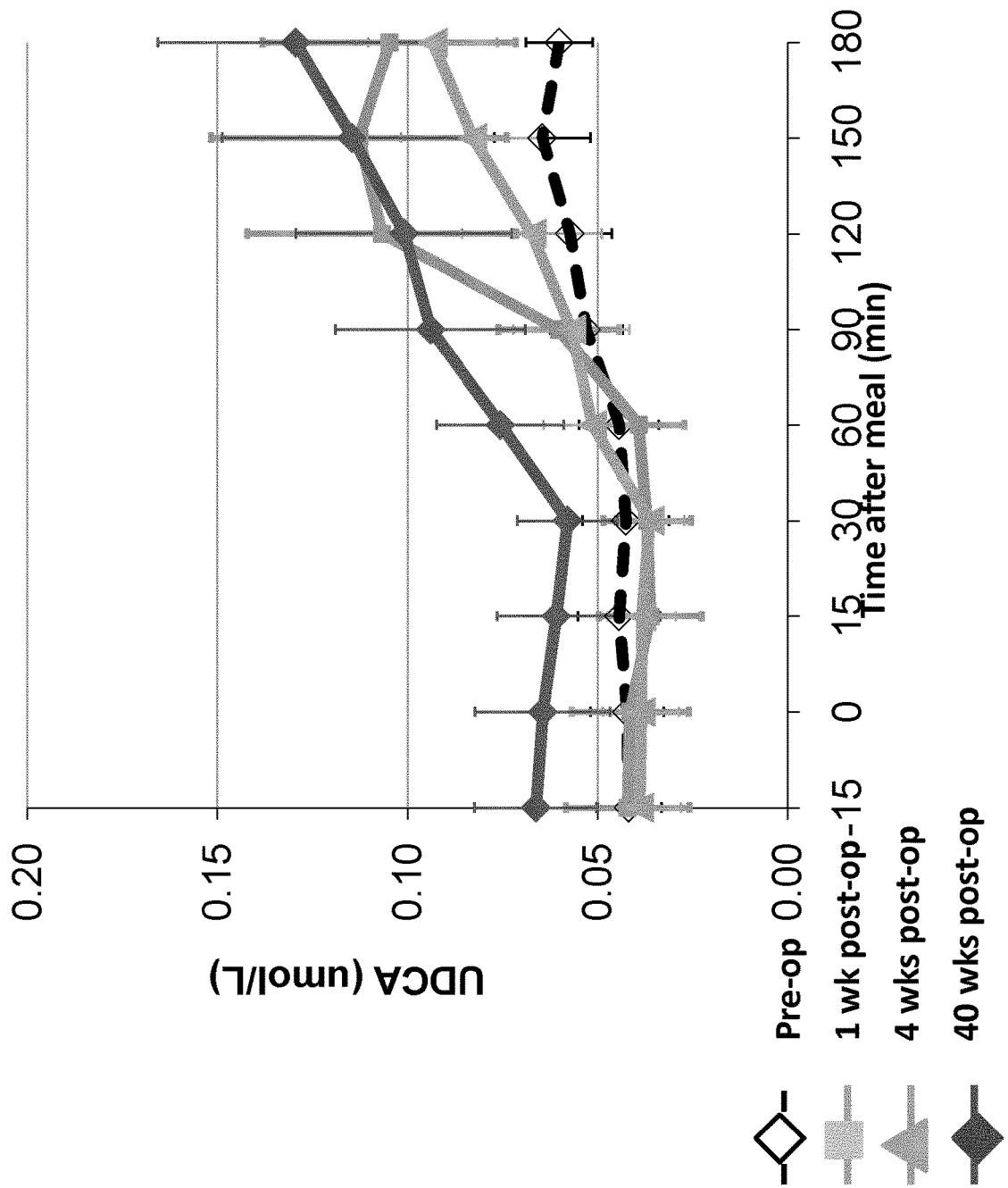
FIG. 23 shows a graph of ursodeoxycholic acid (UDCA) present in serum of obese individuals preoperative, 1 week postoperative, 4 weeks postoperative and 40 weeks postoperative in relation to a meal.
Figure 24:
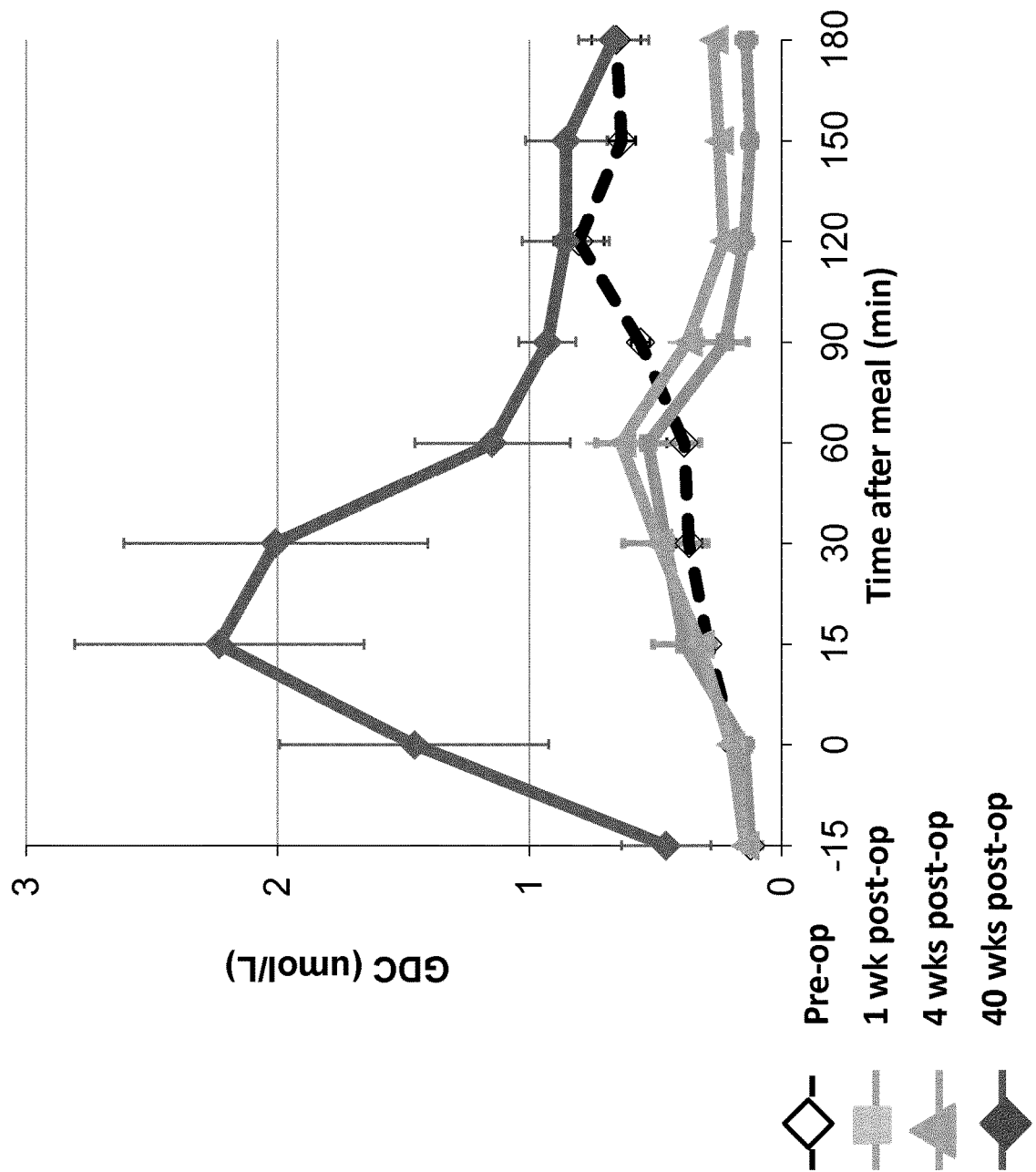
FIG. 24 shows a graph of glycine deoxycholic acid (GDC) present in serum of obese individuals preoperative, 1 week postoperative, 4 weeks postoperative and 40 weeks postoperative in relation to a meal.
Figure 25:
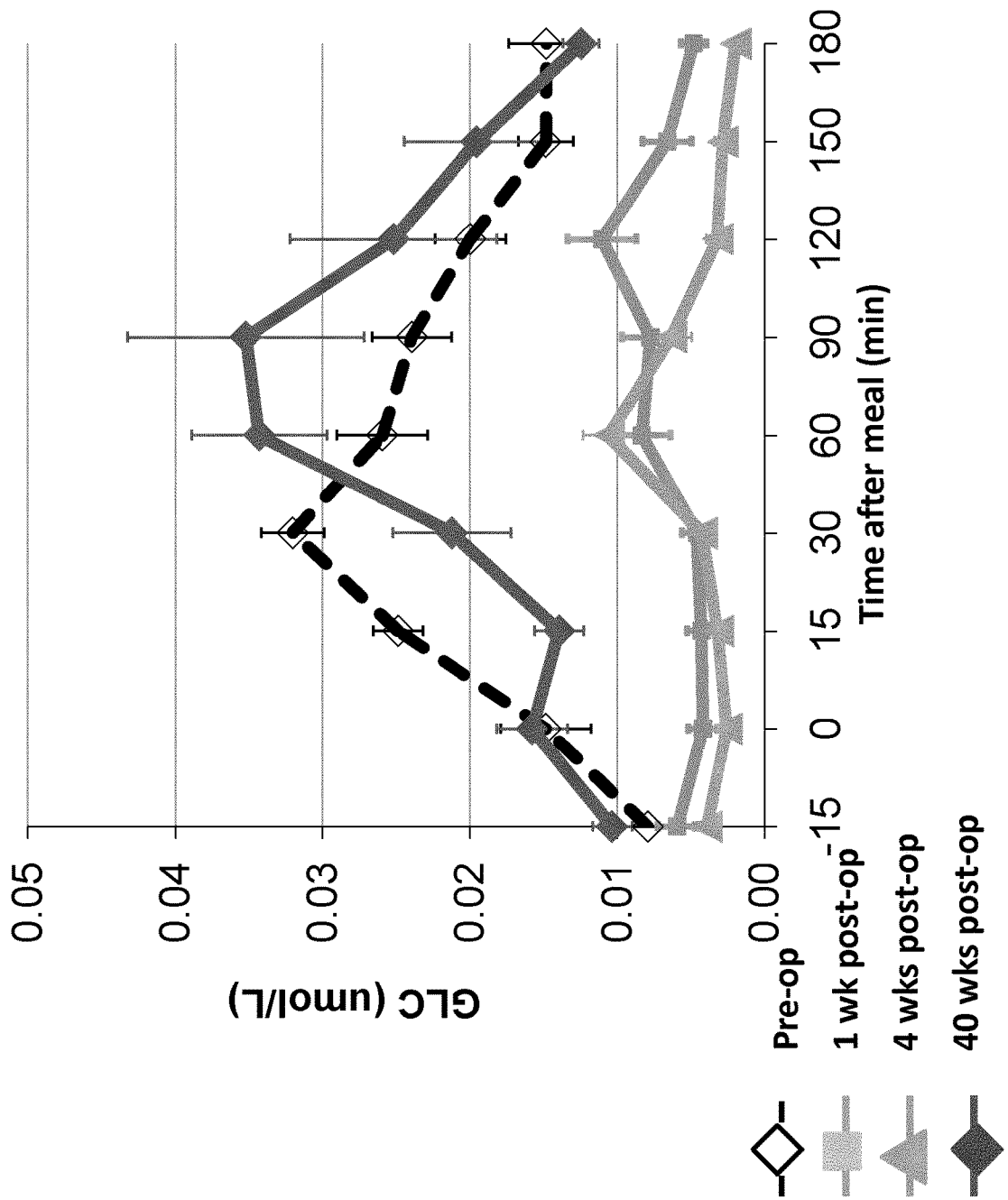
FIG. 25 shows a graph of glycine lithocholic acid (GLC) present in serum of obese individuals preoperative, 1 week postoperative, 4 weeks postoperative and 40 weeks postoperative in relation to a meal.
Figure 26:
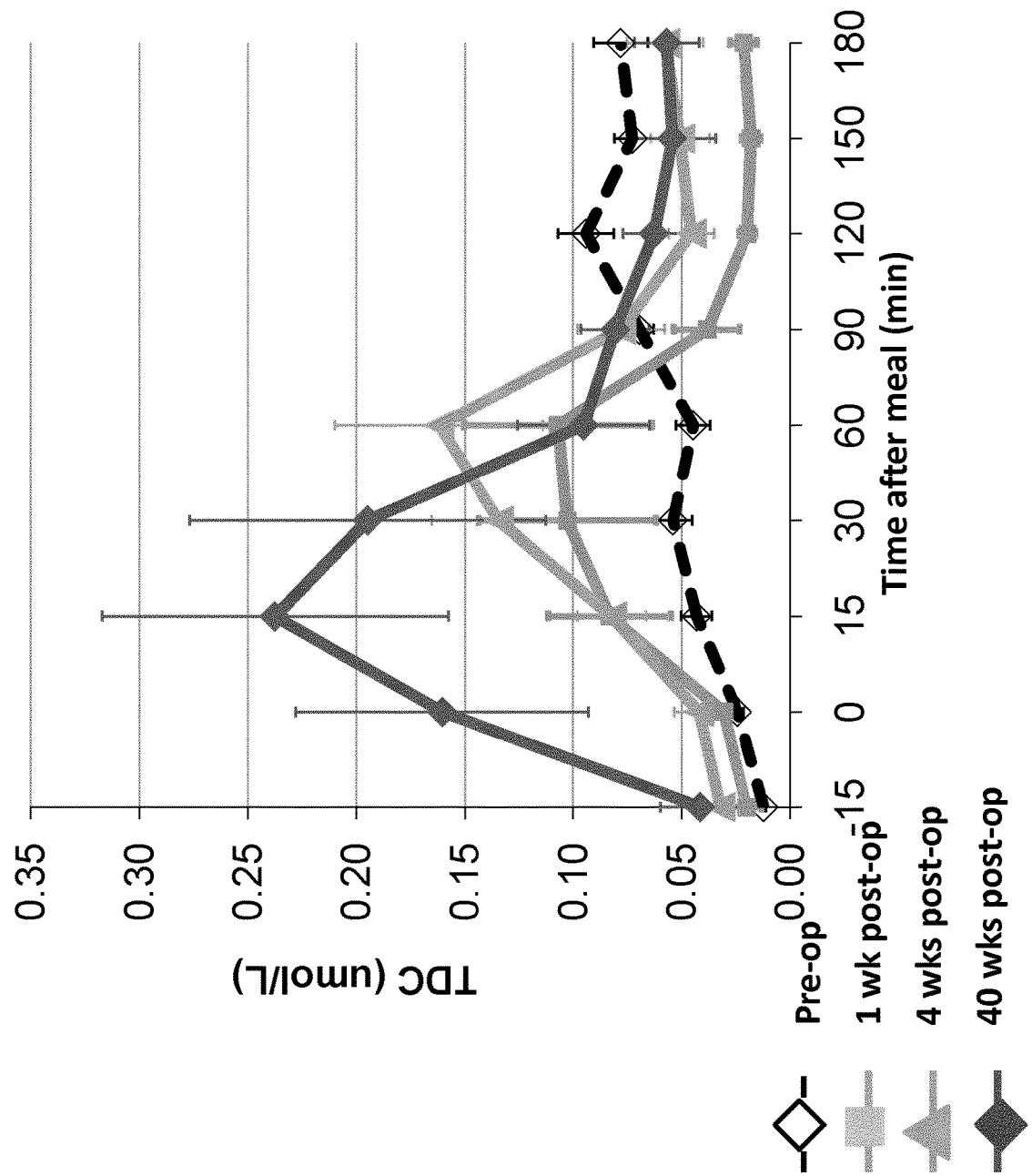
FIG. 26 shows a graph of taurine deoxycholic acid (TDC) present in serum of obese individuals preoperative, 1 week postoperative, 4 weeks postoperative and 40 weeks postoperative in relation to a meal.
Figure 27:
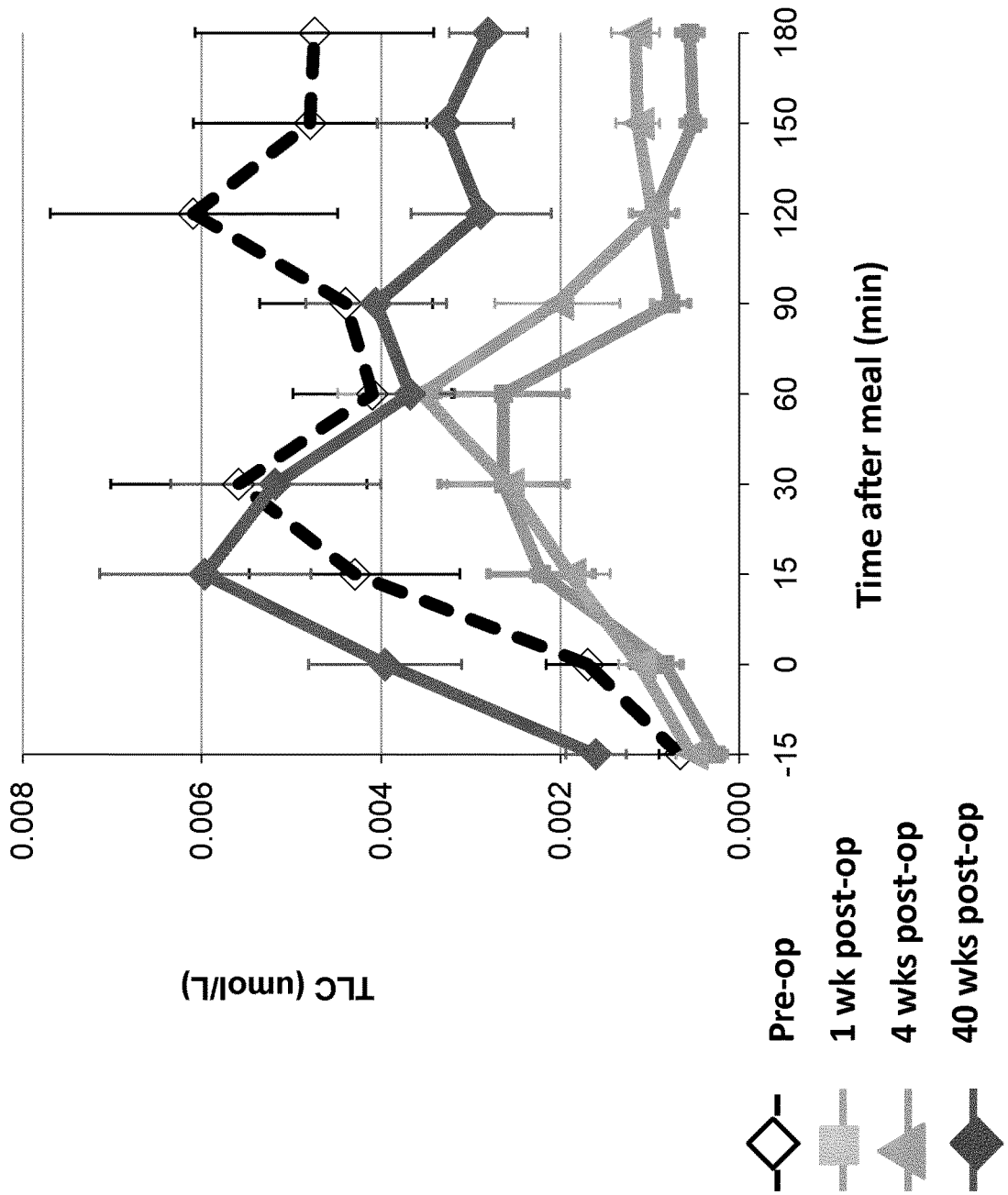
FIG. 27 shows a graph of taurine lithocholic acid (TLC) present in serum of obese individuals preoperative, 1 week postoperative, 4 weeks postoperative and 40 weeks postoperative in relation to a meal.
Figure 28:
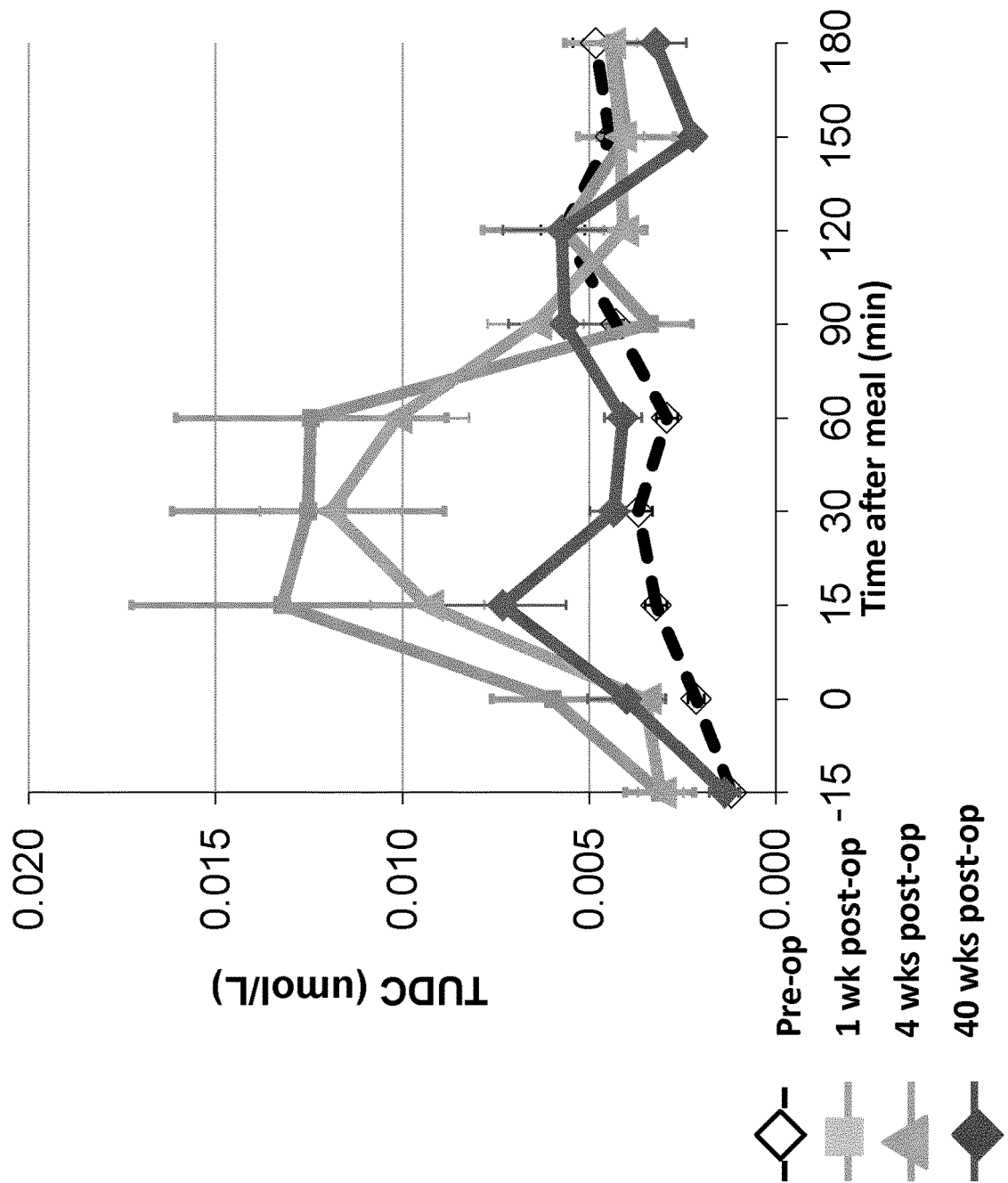
FIG. 28 shows a graph of taurine ursodeoxycholic acid (TUDC) present in serum of obese individuals preoperative, 1 week postoperative, 4 weeks postoperative and 40 weeks postoperative in relation to a meal.

Levels of cholic acid (CA, FIG. 15), glycocholic acid (GCA, FIG. 16), taurine cholic acid (TCA, FIG. 17), chenodeoxycholic acid (CDCA, FIG. 18), glycine chenodeoxycholic acid (GCDC, FIG. 19), taurine chenodeoxycholic acid (TCDC, FIG. 20), deoxycholic acid (DCA, FIG. 21), lithocholic acid (LCA, FIG. 22), ursodeoxycholic acid (UDCA, FIG. 23), glycine deoxycholic acid (GDC, FIG. 24), glycine lithocholic acid (GLC, FIG. 25), taurine deoxycholic acid (TDC, FIG. 26), taurine lithocholic acid (TLC, FIG. 27), taurine ursodeoxycholic acid (TUDC, FIG. 28) were measured in subjects prior to surgical intervention and at 1 week post surgical intervention, 4 weeks post surgical intervention and 40 weeks post surgical intervention. Obesity was associated with a decrease in primary conjugated bile acids and all secondary bile acids (21-78% for different bile acids). Most significant reductions were observed for glycocholic acid, ursodeoxycholic acid and all 3 lithocholic acid (LCA) moieties ($p<0.05$ by AUC analyses). In contrast, obesity in women was associated with a rise (4-343%) in 13 of the 15 major bile acids.

In men, obesity attenuates the meal-induced rise in circulating bile acids most notably in LCAs, which have the highest affinity for the receptor, TGR5. These lower bile acid levels may decrease the satiety response and the thermic effect of food due to decreased activation of TGR5 after a meal. Obesity in women is associated with an increase in the post-prandial bile acid response.

Example 5

Meal-Induced Circulating Bile Acids

A detailed analysis of fasting and post-prandial circulating bile acid (BA) responses was conducted. Post-gastric bypass individuals were examined using a longitudinal design in which each subject served as the subject's own control. Four lean men (BMI 18-25 kg/m$^2$) and 10 men with moderate to severe obesity (BMI≥35 kg/m$^2$), four of whom were scheduled to undergo RYGB, were recruited. Subjects with evidence of liver disease, with a disrupted enterohepatic circulation from previous bowel resection, diarrheal or malabsorptive syndromes, on treatments expected to alter the gut microbiota such as probiotics or antibiotics, or on treatments with BA sequestrants were excluded. Written informed consent was obtained from each subject. The study was approved by the Massachusetts General Hospital Institutional Review Board.

To control for the potential effects of diet and activity on BA levels, subjects completed a 4-day food diary and 3-day Bouchard physical activity diary prior to each study visit. Subjects were admitted to the Clinical Research Center at 9:00 am after an 8-hour overnight fast. Upon admission, height and weight were measured in light clothing without shoes using a calibrated stadiometer and scale. Subjects were asked to drink a standard 8-ounce liquid meal (Two-CalHN, 475 calories, 40% carbohydrate, 40% fat, 20% protein) slowly over a 20-minute period. The 20 minutes was allotted to standardize intake across all groups and was based on tolerability of the liquid meal ingestion early after RYGB. Blood samples were drawn through an indwelling intravenous catheter 15 minutes prior to meal ingestion, at the completion of meal ingestion (time 0), and at 30, 60, 120 and 180 minutes after meal completion. Samples were collected into EDTA-containing tubes and processed within 15 minutes of collection. Plasma aliquots were stored at −80° C. for later analysis.

The four subjects with obesity undergoing surgery were further evaluated longitudinally, and each subject underwent the testing procedures described above at 5 separate visits; four weeks before and one week before RYGB; and one, four and 40 weeks after surgery. At each of these visits, sampling time points for the subjects included 15 minutes prior to meal ingestion and every 30 minutes after meal ingestion for up to three hours.

Concentrations of individual BAs were determined using reverse-phase high-performance liquid chromatography/mass spectroscopy (TNO Laboratories, The Netherlands), as previously described in Bobeldijk, I. et al., *J. Chromatogr. B Analyt. Technol. Biomed. Life Sci.* 871: 306-313. The BAs measured were cholic acid (CA), taurocholic acid (TCA), glycocholic acid (GCA), chenodeoxycholic acid (CDCA), taurochenodeoxycholic acid (TCDCA), glycochenodeoxycholic acid (GCDCA), deoxycholic acid (DCA), taurodeoxycholic acid (TDCA), glycodeoxycholic acid (GDCA), lithocholic acid (LCA), taurolithocholic acid (TLCA), glycolithocholic acid (GLCA), ursodeoxycholic acid (UDCA), tauroursodeoxycholic acid (TUDCA), and glycoursodeoxycholic acid (GUDCA). These 15 BAs account for more than 95 percent of the circulating BAs found in humans. Pooled aliquots from each of the study samples were used as quality control (QC) samples that were run in every tenth position. Samples were run in five batches. To more stringently control for measurement error, QC samples were included in random positions within and between batches to which the testing laboratory was blinded so as to obtain an unbiased estimate of the within-batch and between-batch variation for individual BAs.

BA concentrations were compared for obese and lean groups using independent sample t-tests, and for before and after RYGB using paired t-tests. The analyses of each fasting and post-prandial timepoint as well as area-under-the-curve (AUC) analysis of post-prandial BA excursion were conducted. AUC was calculated using the trapezoidal method. Statistical analyses were performed using SPSS, version 18 (IBM, Armonk, N.Y.). A p<0.05 was considered significant. Data are depicted as mean+/−standard error of the mean (s.e.m.).

The mean BMI was 44.3 (±6.6) kg/m$^2$ in subjects with obesity, and 22.6 (±1.5) kg/m$^2$ in lean subjects. The mean age was 43.5 (±13.9) and 36.5 (±7.7) years in the obesity and lean groups, respectively (p=0.37). Table 2 shows the characteristics of subjects in the obesity and lean groups. There was no difference in physical activity or total dietary intake between the groups. The group of men with obesity had a greater percentage of their total calories derived from protein (19.2 [±1.4] vs 14.4 [±4.5]; p=0.008) and a lower percentage from carbohydrates (40.1 [±4.6] vs 50.0 [±10.7]; p=0.03). Absolute carbohydrate intake (grams/day) was also lower in the obesity group than in the lean group (p=0.004). There was no difference in dietary fat consumption between the groups.

TABLE 2

Subject Characteristics

| | Obese men | Lean men | p-value |
|---|---|---|---|
| N | 10 | 4 | n/a |
| Age, years, mean (SD) | 43.5 (13.9) | 36.5 (7.7) | 0.37 |
| BMI, kg/m$^2$, mean (SD) | 44.3 (6.6) | 22.6 (1.5) | <0.0001 |
| Activity, kcal/kg/day, mean (SD) | 43.6 (7.1) | 46.9 (6.2) | 0.44 |
| Total Food Intake | | | |
| grams/day, mean (SD) | 2824 (751) | 3498 (389) | 0.12 |
| kcal/day, mean (SD) | 2255 (535) | 2774 (329) | 0.10 |
| Fat Intake | | | |
| grams/day, mean (SD) | 100.3 (27.3) | 107.4 (28.8) | 0.67 |
| % of total calories, mean (SD) | 39.5 (5.6) | 34.1 (6.6) | 0.14 |
| Protein Intake | | | |
| grams/day, mean (SD) | 106.7 (21.0) | 102.3 (39.7) | 0.79 |
| % of total calories, mean (SD) | 19.2 (1.4) | 14.4 (4.5) | 0.008 |
| Carbohydrate Intake | | | |
| grams/day, mean (SD) | 230.9 (53.6) | 345.6 (55.5) | 0.004 |
| % of total calories, mean (SD) | 40.1 (4.6) | 50.0 (10.7) | 0.03 |

The average intra- and inter-batch coefficients of variation (CVs) were both <10% for the individual BAs in and across all five batches, except for three outliers, LCA, TUDC, and TLCA. These three BAs with low circulating concentrations had intra-batch CVs >30% for one out of five, one out of five, and two out of five runs, respectively.

Figure 29C:
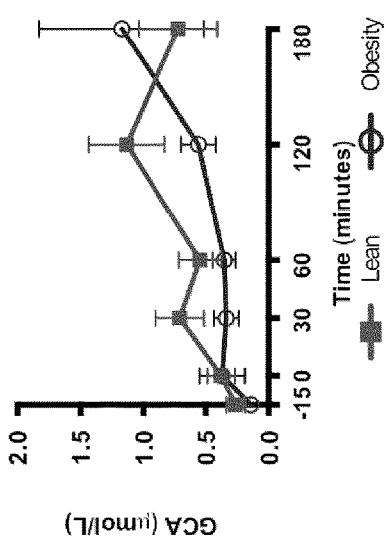
FIG. 29C is a line graph of glycocholic acid (GCA)
Figure 29B:
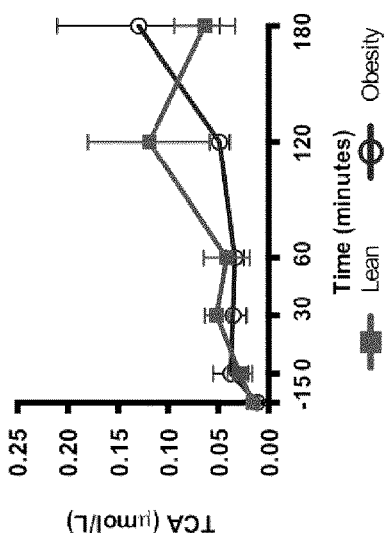
FIG. 29B is a line graph of taurocholic acid (TCA)
Figure 29A:
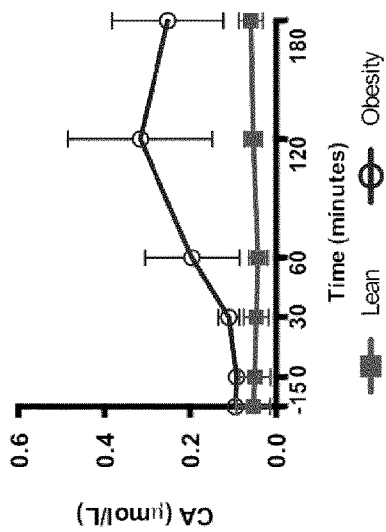
FIGS. 29A-29O are graphs of fasting and post-prandial circulating bile acid (BA) levels over time in obese individuals. Time course of individual plasma BAs before and after ingestion of a standard liquid meal in individuals with obesity (open circles) and lean controls (closed squares). *P<0.05.
Figure 29F:
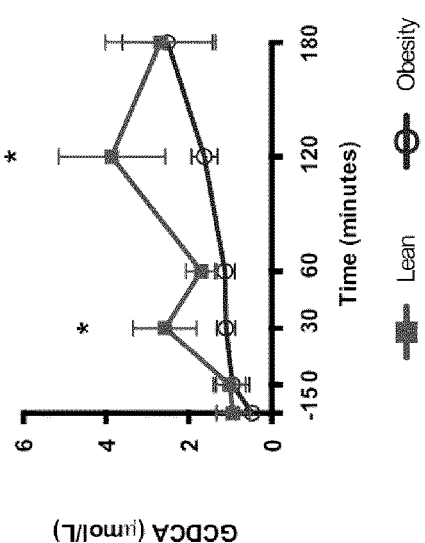
FIG. 29F is a line graph of glycochenodeoxycholic acid (GCDCA)
Figure 29E:
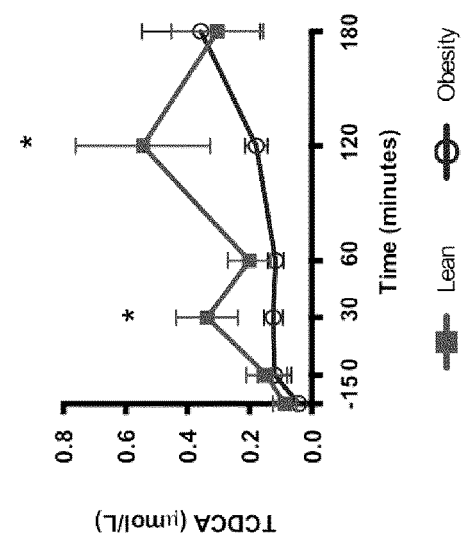
Figure 29D:
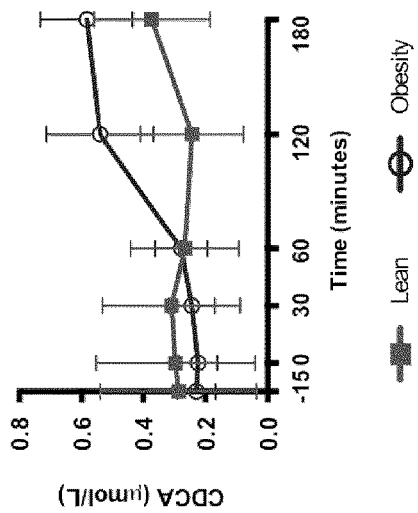
FIG. 29D is a line graph of chenodeoxycholic acid (CDCA)
Figure 29I:
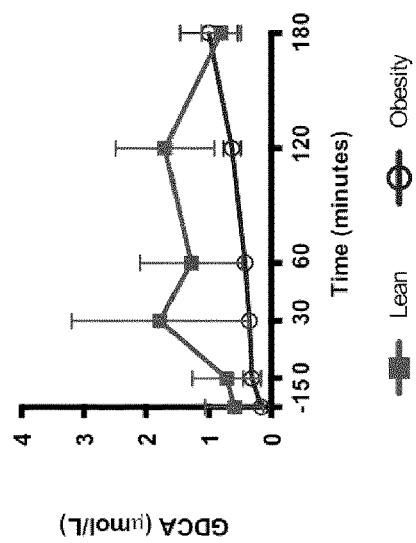
FIG. 29I is a line graph of glycodeoxycholic acid (GDCA)
Figure 29H:
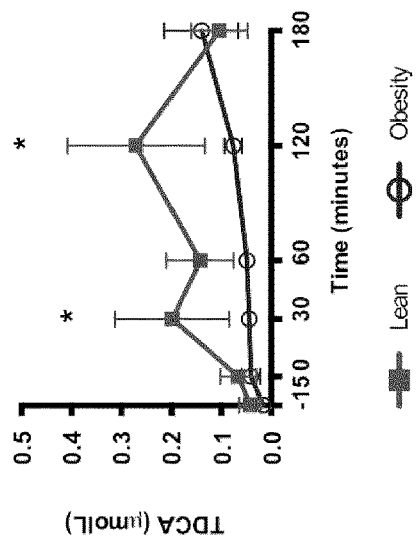
FIG. 29H is a line graph of taurodeoxycholic acid (TDCA)
Figure 29G:
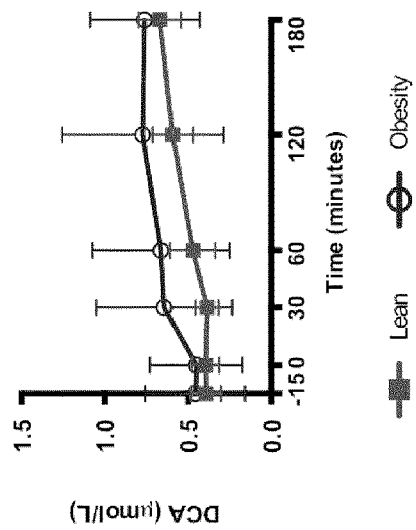
FIG. 29G is a line graph of deoxycholic acid (DCA)
Figure 29L:
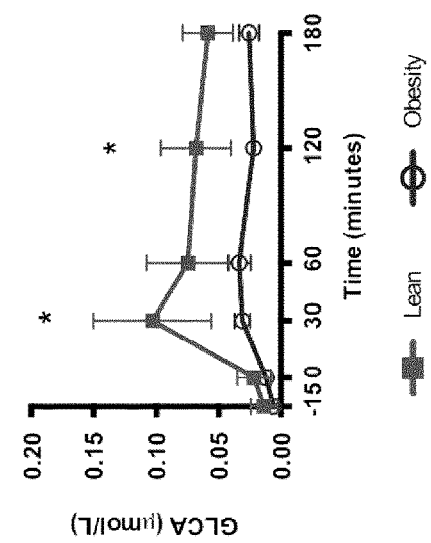
FIG. 29L is a line graph of glycolithocholic acid (GLCA)
Figure 29K:
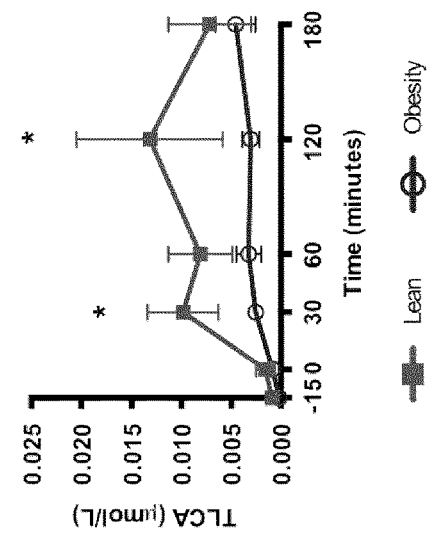
FIG. 29K is a line graph of taurolithocholic acid (TLCA)
Figure 29J:
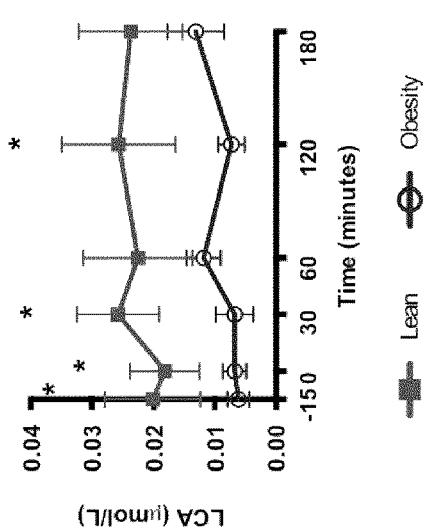
FIG. 29J is a line graph of lithocholic acid (LCA)
Figure 29O:
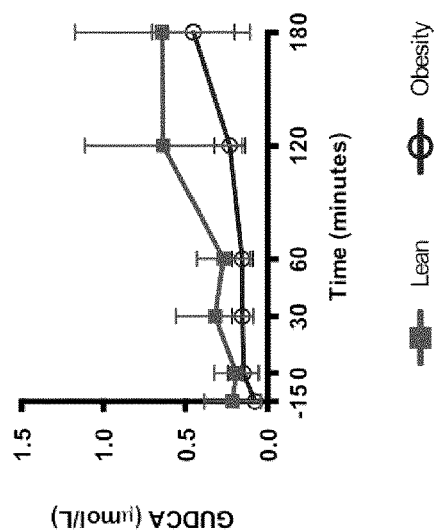
Figure 29N:
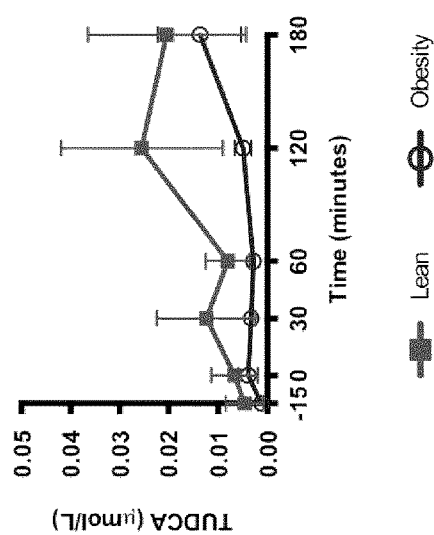
FIG. 29N is a line graph of tauroursodeoxycholic acid (TUDCA)
Figure 29M:
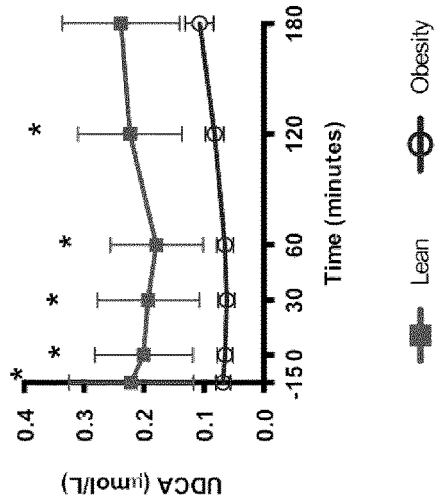
FIG. 29M is a line graph of ursodeoxycholic acid (UDCA)

Men with obesity had lower fasting circulating BAs and a blunting of the early post-prandial BA response compared to lean men (FIGS. 29A-29O show the individual bile acids). Fasting unconjugated LCA (FIG. 29J) and UDCA (FIG. 29M) levels were statistically significantly lower in the obesity group (0.006 [±0.006] µmol/L vs. 0.020 [±0.015] µmol/L, 0.07 [±0.04] µmol/L vs. 0.22 [±0.21]µmol/L, respectively; p<0.05). The total fasting conjugated BA subset was 59% lower in the obesity group (0.91 [±0.26]µmol/L vs. 2.2 [±0.78] µmol/L; p<0.05).

At 30 and 120 minutes after meal ingestion, the expected increase in circulating BAs was significantly blunted in the obesity group compared to the lean group for most of the glycine- and taurine-conjugated BAs, including GCDCA (FIG. 29F), GLCA (FIG. 29L), TCDCA (FIG. 29E), TDCA (FIG. 29H), and TLCA (FIG. 29K) (p<0.05). Similarly, circulating levels of LCA (FIG. 29J) and UDCA (FIG. 29M) were decreased in the obesity group at several time points after meal ingestion (p<0.05). A similarly low concentration at 30 and 120 minutes after meal ingestion was noted for several of the remaining BAs (GCA, GDCA, GUDCA, TCA, TUDCA and DCA) in the obesity group. There was a noticeable difference in the timing and pattern of the post-prandial BA excursion curve between the two groups. In subjects with obesity, BA levels rose gradually throughout the 3-hour post-prandial period. In contrast, lean men displayed a rapid rise in circulating BA levels in response to a meal with an earlier and higher peak at 30 minutes after meal ingestion and a second peak at 120 minutes for all taurine- and glycine-conjugated, primary and secondary BAs.

Figure 30A:
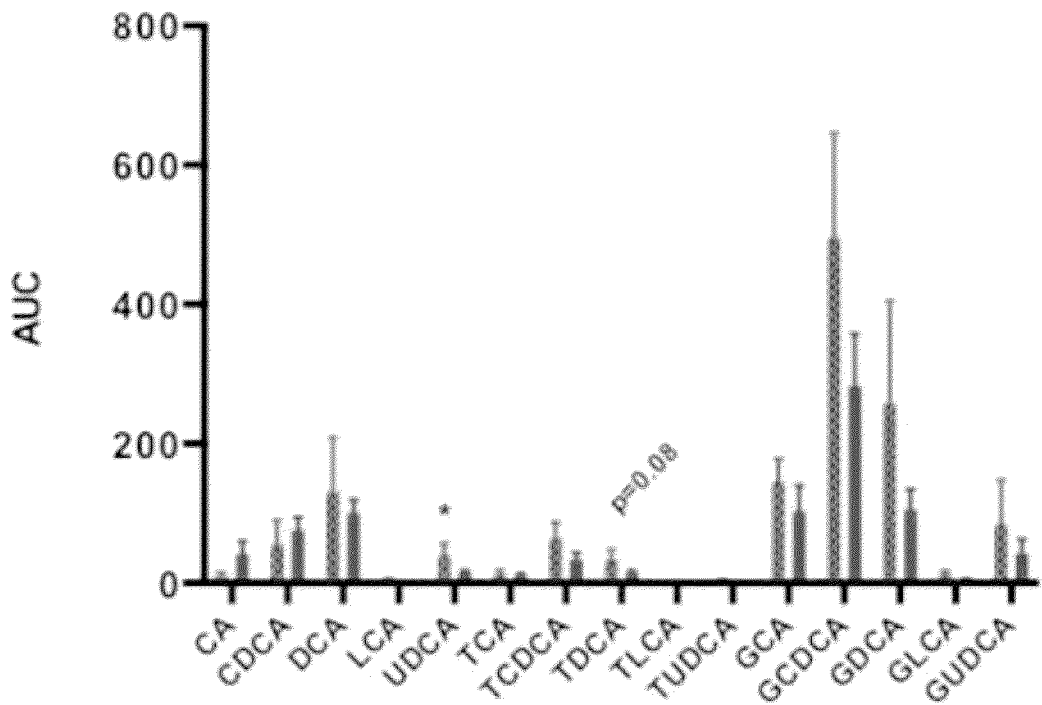
FIGS. 30A-C show graphs of area under the curve (AUC) analyses of the 3-hour post-prandial BA excursions. *P<0.05.
Figure 30B:
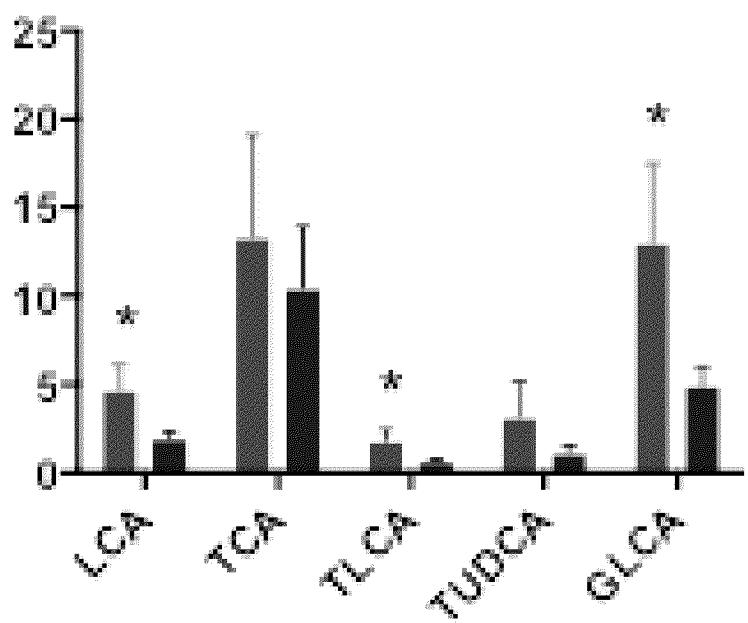
Figure 30C:
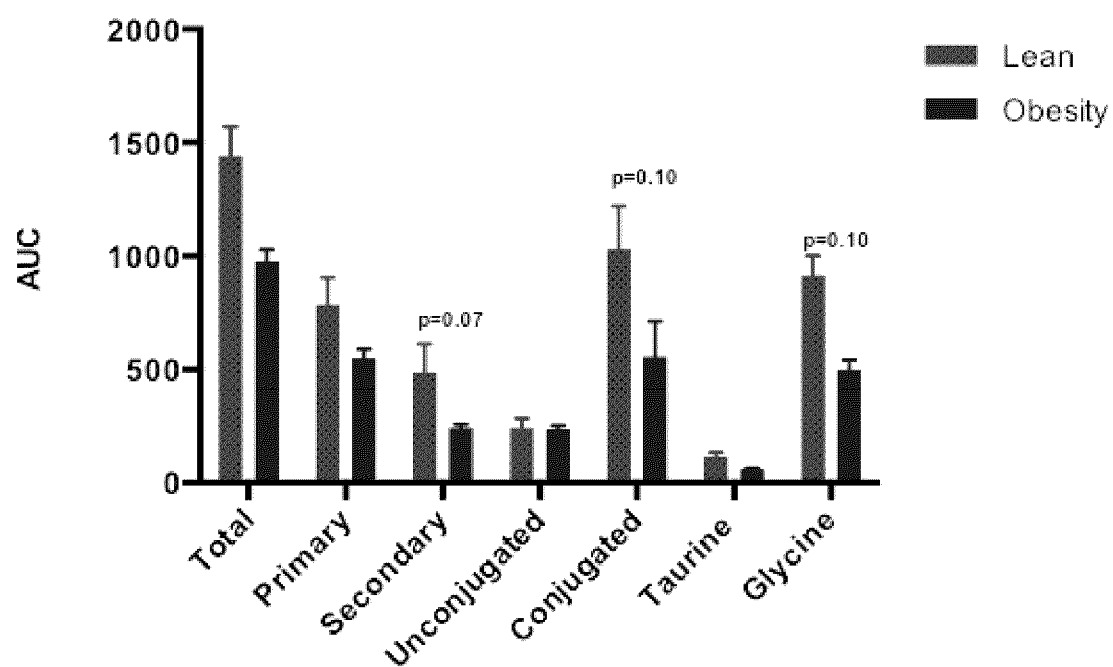

Despite the small number of subjects studied, the AUC for the post-prandial excursion of lithocholate moieties (LCA, TLCA and GLCA) and UDCA in the obesity group were statistically lower than in the lean group (p<0.05; FIGS. 30A and 30B, left bar=lean, right bar=obesity). While these differences did not reach statistical significance in this pilot study, the average AUC of the post-prandial excursion of the circulating BA curve in the obesity group appeared to be lower than in the lean group for all the remaining individual taurine- and glycine-conjugated BAs as well as for total BAs and primary, secondary, total conjugated, taurine-conjugated and glycine-conjugated BA subsets (FIG. 30C, left bar=lean, right bar=obesity). There were no observed differences between the obesity and lean groups in the overall composition of the circulating BA pool.

Four of the subjects with obesity underwent RYGB (mean age 47 [±13.8] years, mean initial BMI 49.3 [±7.0] kg/m²). All had uncomplicated perioperative and post-operative courses. Pre-operative and post-operative subject characteristics are displayed in Table 3. The percent excess body weight loss (% EBWL) exhibited by each subject was consistent with the distribution of % EBWL clinically observed and previously reported at our center. Subjects displayed a statistically significant decrease in reported physical activity at post-operative week one, reflecting the early post-surgical recovery phase. Physical activity subsequently returned to baseline with no significant difference in activity between baseline and 40 weeks after surgery.

TABLE 3

Subject Characteristics Before and After RYGB

|  | Pre-op | 1 week post-op | p-value[a] | 4 weeks post-op | p-value[a] | 40 weeks post-op | p-value[a] |
|---|---|---|---|---|---|---|---|
| Weight, kg, mean (SD) | 167.7 (16.6) | 158.3 (16.7) | 0.002 | 149.4 (16.7) | 0.004 | 113.3 (11.9) | 0.006 |
| BMI, kg/m², mean (SD) | 49.3 (7.0) | 46.6 (6.8) | 0.002 | 44.0 (7.3) | 0.001 | 33.2 (3.8) | 0.009 |
| EBWL, %, mean (SD) | n/a | 12.1 (4.7) | n/a | 23.6 (8.7) | n/a | 66.9 (13.8) | n/a |
| Activity, kcal/kg/day, mean (SD) | 42.9 (5.1) | 34.6 (2.2) | 0.02 | 38.4 (3.2) | 0.06 | 48.7 (7.5) | 0.12 |
| Total Food Intake |  |  |  |  |  |  |  |
| grams/day, mean (SD) | 2368 (145) | 1775 (678) | 0.14 | 2180 (417) | 0.47 | 1869 (598) | 0.19 |
| kcal/day, mean (SD) | 1885 (210) | 448 (171) | 0.004 | 649 (240) | 0.05 | 1338 (356) | 0.05 |
| Fat Intake |  |  |  |  |  |  |  |
| grams/day, mean (SD) | 88.5 (20.1) | 7.6 (5.2) | 0.003 | 25.7 (10.2) | 0.08 | 59.3 (32.1) | 0.28 |
| % of total calories, mean (SD) | 42.0 (6.2) | 14.5 (9.1) | 0.0005 | 34.5 (4.5) | 0.31 | 36.8 (13.7) | 0.63 |
| Protein Intake |  |  |  |  |  |  |  |
| grams/day, mean (SD) | 90.5 (11.1) | 24.6 (7.6) | 0.006 | 42.4 (25.2) | 0.16 | 71.7 (22.1) | 0.29 |
| % of total calories, mean (SD) | 19.6 (0.39) | 24.0 (4.7) | 0.14 | 25.8 (5.8) | 0.19 | 22.4 (8.4) | 0.55 |
| Carbohydrate Intake |  |  |  |  |  |  |  |
| grams/day, mean (SD) | 185.8 (28.7) | 71.5 (28.9) | 0.02 | 63.9 (17.2) | 0.04 | 135.7 (38.3) | 0.14 |
| % of total calories, mean (SD) | 38.0 (5.6) | 61.4 (5.5) | <0.0001 | 39.4 (8.3) | 0.83 | 40.3 (15.2) | 0.84 |

Although pre- and post-operative diets did not differ significantly in total grams per day, total daily caloric intake decreased significantly throughout the post-operative period. The composition of the diet was demonstrably altered at post-operative week one with a significant decrease in percent fat and a significant increase in percent carbohydrate intake. These differences in composition, however, did not persist at post-operative weeks 4 or 40.

No significant changes in fasting circulating BA levels after RYGB were detected. The post-prandial excursion of circulating BAs was significantly altered after RYGB (FIGS. 31A-31N). Pre-operatively, all measured BAs except the lithocholic acid moieties, rose gradually throughout the three-hour post-prandial period. As early as one week after RYGB, this pattern of excursion was altered, with the majority of measured BAs rising rapidly and reaching peak concentrations between 15 and 60 minutes after meal ingestion. For the glycine conjugates of the major BAs (GCA, FIG. 31C; GCDCA, FIG. 31G; and GDCA, FIG. 31D), there was a progressive increase in peak post-prandial levels and shortening of the time to peak from post-operative week one through post-operative week 40. In contrast, for several taurine conjugates, including TCA (FIG. 31B), TCDCA (FIG. 31F) and TUDCA (FIG. 31N), the highest post-prandial peak concentrations were noted at postoperative week 4 with a subsequent decline towards baseline by postoperative week 40. Post-prandial levels of all measured lithocholic acid species (LCA, GLCA and TLCA) initially decreased after surgery and returned to the preoperative baseline by 40 weeks after surgery. Notably, we observed no changes in the patterns of the unconjugated circulating BAs (CDCA, DCA and UDCA) in response to RYGB.

Figure 31P:
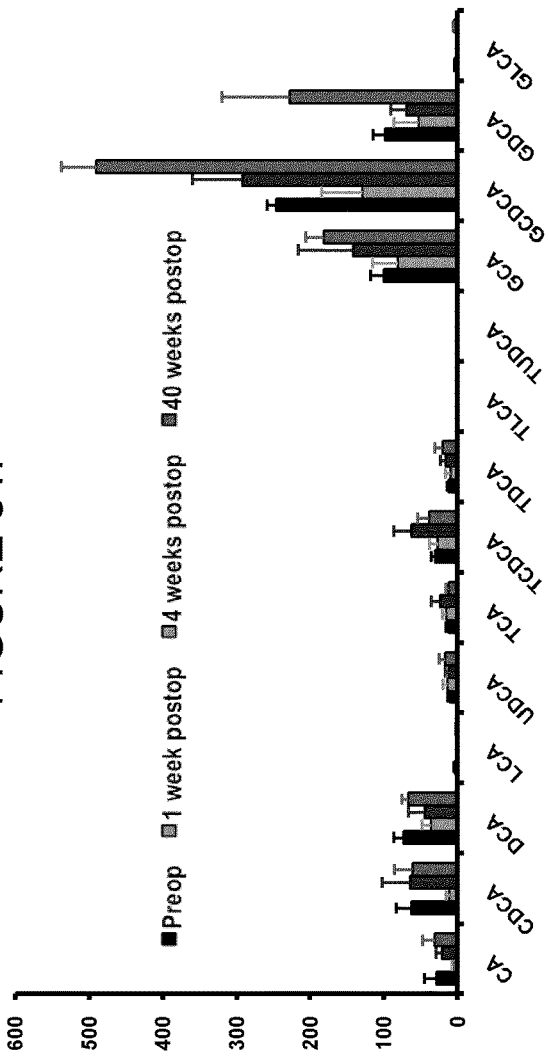
Figure 31Q:
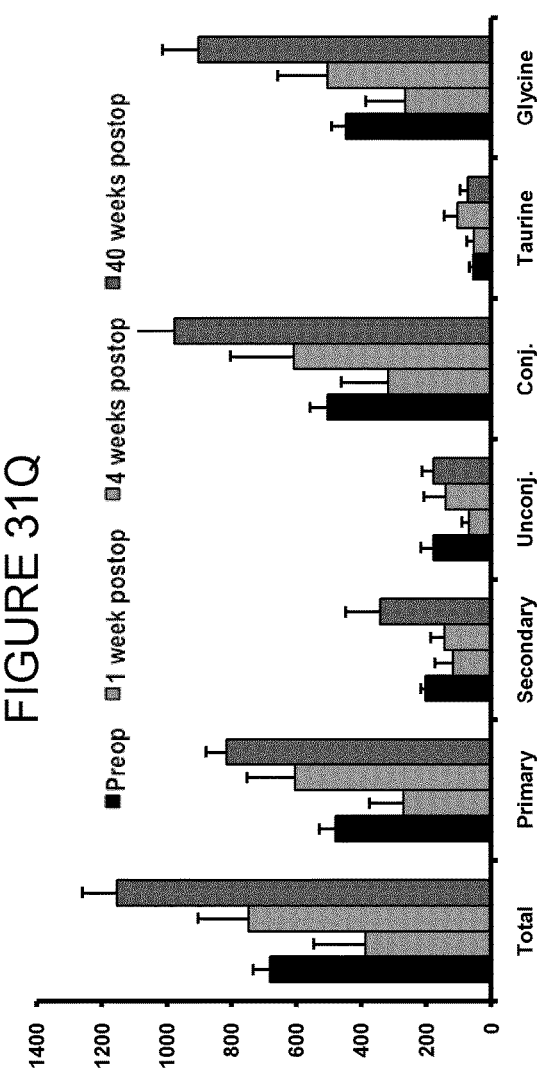
Figure 32A:
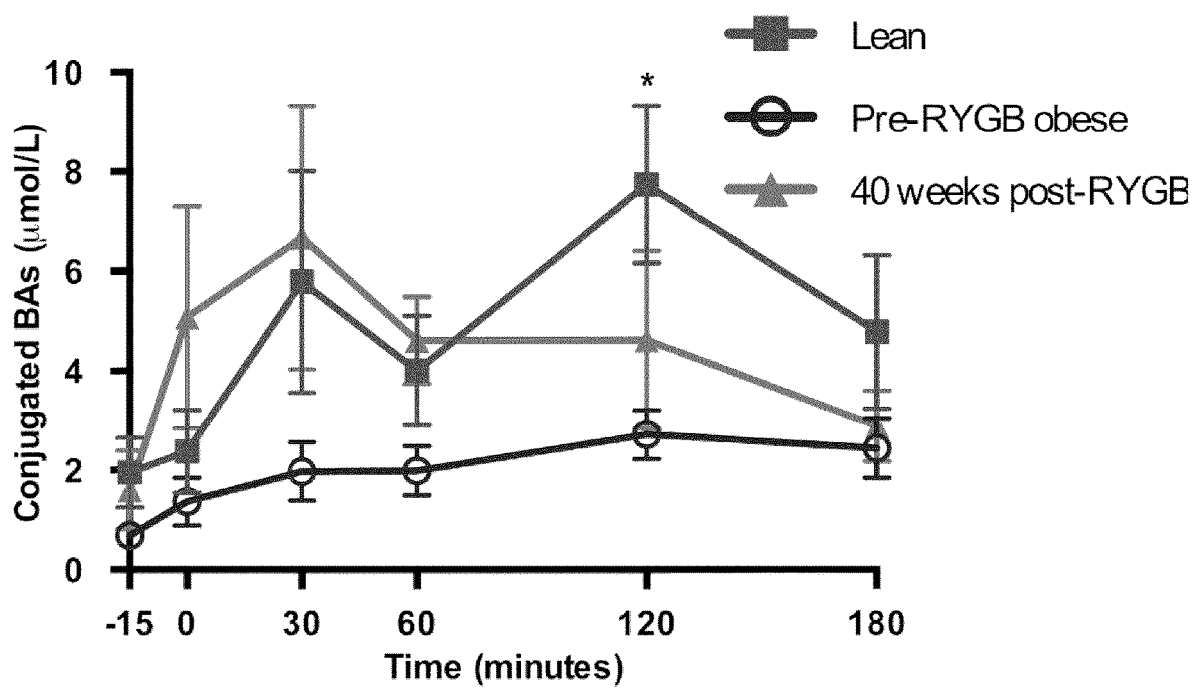
FIG. 32A is a graph of post-prandial excursion of conjugated BAs for four subjects prior to undergoing RYGB (open circles) and 40 weeks after RYGB (closed triangles) compared to lean controls (closed squares)*P<0.05 pre-RYGB.
Figure 32B:
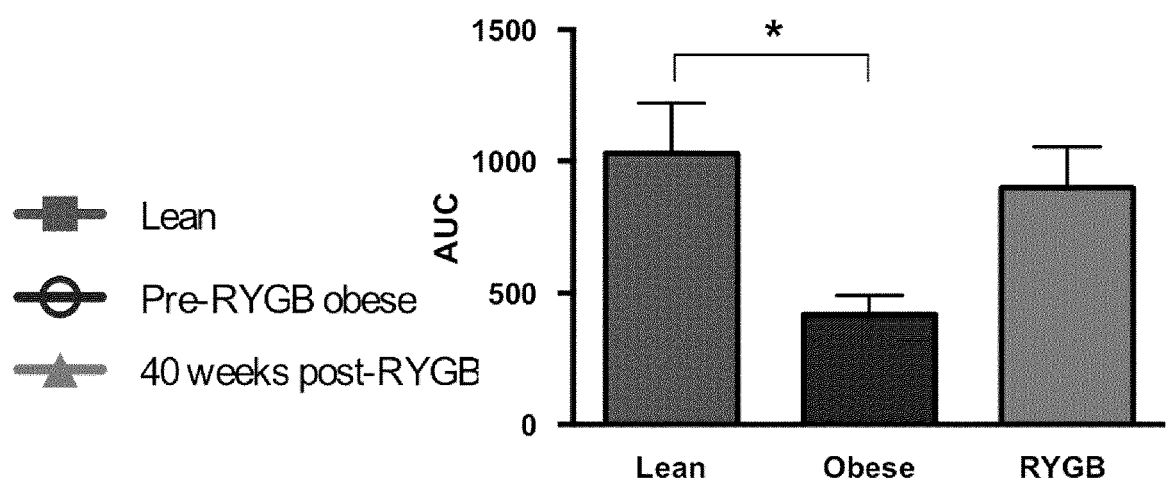
FIG. 32B is a graph of the AUC analyses of total conjugated BAs for four subjects prior to undergoing RYGB (open circles) and 40 weeks after RYGB (closed triangles) compared to lean controls (closed squares) *P<0.05 pre-RYGB.

AUC analysis of total BAs and BA subsets showed that total BAs rose significantly by post-operative week 40 as did primary, total conjugated and glycine-conjugated subsets ($p<0.05$, FIGS. 31O-31Q). By post-operative week 40, there was no statistically significant difference between the BA responses of the 4 subjects who underwent RYGB and the 4 lean controls (FIG. 32A) and the AUC analysis of the BA responses (FIG. 32B).

Example 5

In Vivo Delivery of Bile Acids

Six Sprague-Dawley rats, between the ages of 34 and 38 weeks of age, were separated into three groups (2 rats per group) for the study. Group 1 included rats maintained on a normal chow diet, Lean. Group 2 included diet-induced obese rats maintained on 60% high fat diet and underwent sham operation 6 weeks prior to the start of the study, (Sham). Group 3 included diet-induced obese rats maintained on 60% high fat diet and underwent Roux en Y gastric bypass operation 6 weeks prior to the start of the study, (RYGB). All rats were maintained under standards and guidelines approved by Subcommittee on Research Animal Care for the Institutional Animal Care and Use Committee at Massachusetts General Hospital.

On day 0, all animals underwent surgical placement of jugular venous catheters (JVC). The animals were allowed to recover for 2 days, then transferred to TSE Metabolic System cages for 3 days for acclimatization prior to the first injection.

On days 6-8, the rats in each group received a control injection of 500 µl of saline via the JVC followed by a 500 µl heparin flush daily just prior to the dark phase. Measurements for body weight, food intake, energy expenditure, and physical activity were taken daily after saline administration.

On days 9-11, the rats in each group received a bile acid injection of 500 µl of bile acid cocktail via the JVC followed by a 500 µl heparin flush daily just prior to the dark phase cycle. Measurements for body weight, food intake, total energy expenditure, and physical activity were taken after bile acid administration. The measurements taken after saline administration and prior to administration of bile acids served as internal controls for measurable effects bile acids had on total energy expenditure and physical activity.

The bile acid cocktail dosages were calculated from bile acid levels obtained from prior RYGB and sham-operated Sprague-Dawley rats following fasting levels of conjugated bile acids in plasma. The bile acid cocktails included:
TUDC: 0.027 umol/L
TDC: 0.032 umol/L
GDC: 0.002 umol/L
TCDC: 0.151 umol/L
GCDC: 0.003 umol/L
TCA: 1.504 umol/L
GCA: 0.064 umol/L A total of 0.06 mg of bile acids per 500 µl injection per 500 gram rat was delivered on each of the three days.

Figure 33:
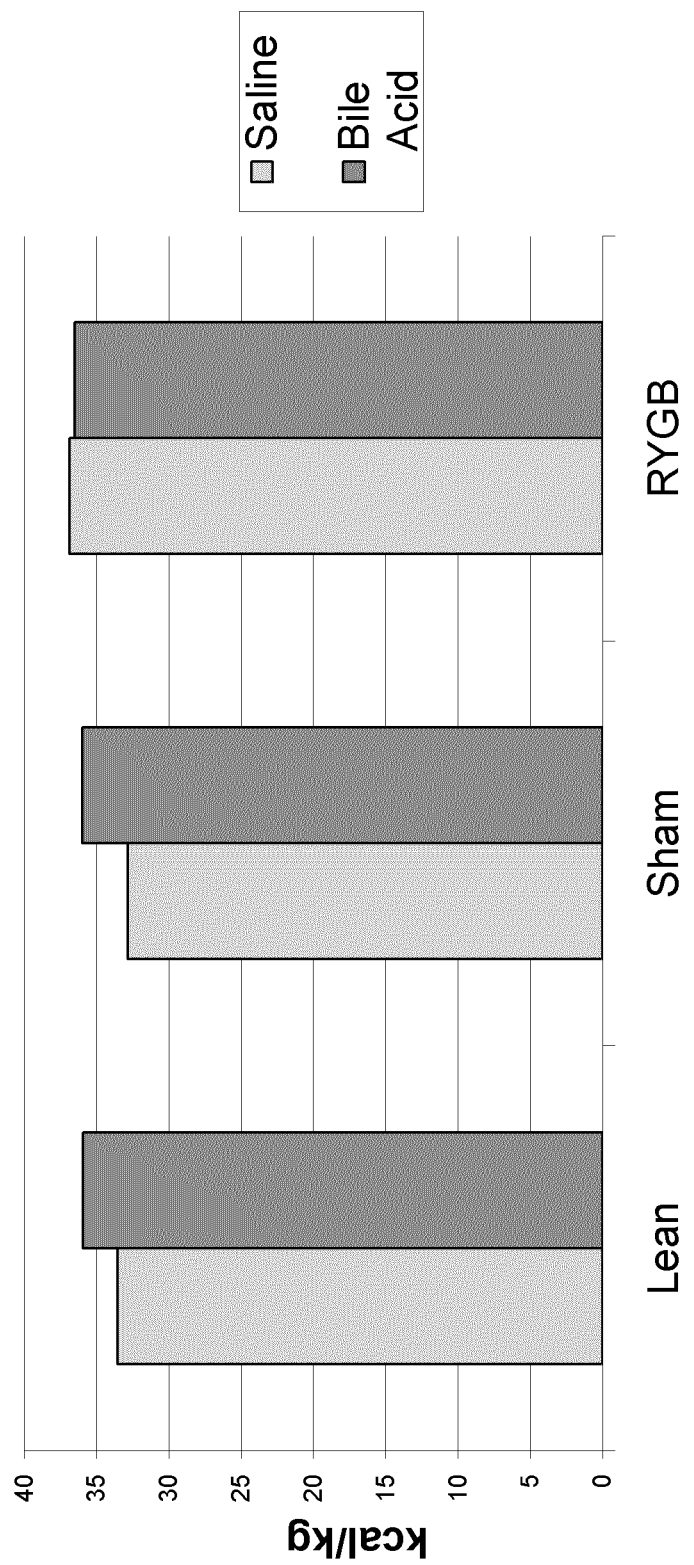
FIG. 33 shows a bar graph of resting energy expenditure measured in Lean, Sham and RYGB rats after administration of saline or bile acids.

Calculated values of resting energy expenditure, as shown in FIG. 33, demonstrate that administration of bile acids to Lean and Sham groups increased the resting energy expenditure as compared to resting levels seen after administration of saline. While bile acid administration had little effect on resting energy expenditure in the RYGB group animals, bile acid administration elevated resting energy expenditure of the Lean and Sham group animals to levels seen in the RYGB rats. Thus, the data supports bile acid administration as a mechanism to alter energy expenditure.

Example 6

Effect of TUDCA on Weight Gain

To examine the effect of circulating bile acids on body weight gain, C57BL/6J mice on a high-fat diet (HFD) were given subcutaneous injections of tauroursodeoxycholic acid (TUDCA, 500 mg/kg) or placebo for 10 weeks (N=6 per group). TUDCA was prepared daily in 0.15 M NaHCO$_3$ (pH adjusted to 7.4). TUDCA or placebo (0.15 M NaHCO$_3$, pH 7.4) was administered twice a week (Monday/Thursday) as 10 µl solution/g of body weight. Body weight (BW) was measured and recorded immediately before each injection and used to calculate the TUDCA or placebo dose to be administered.

Animals were 10 weeks of age at the start of the experiment (BW=32.6 g±2.6) and were on a RFD from weaning that provided 60% of total energy as fat, 20% as carbohydrate, and 20% as protein (D12492 diet; Research Diets, New Brunswick, N.J.). Animals were individually housed on wire floors without bedding and maintained in a 12-hour light-dark cycle (lights on at 0700 hours) in a facility with an ambient temperature of 19-22° C.

Figure 34:
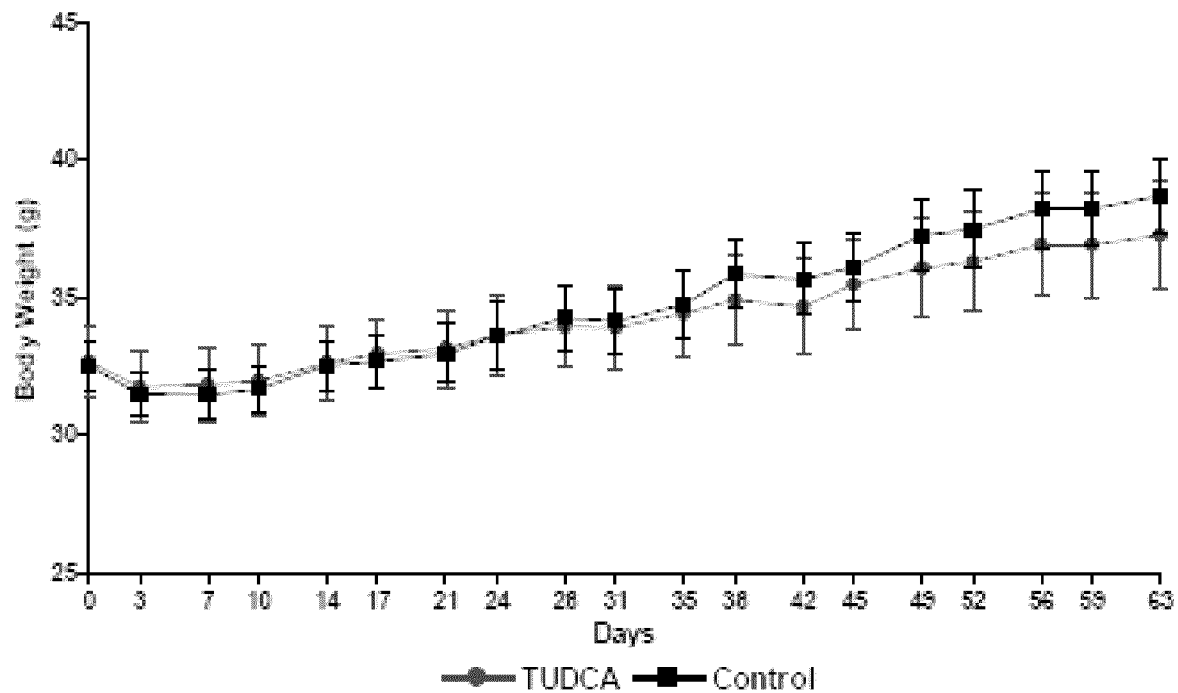
FIG. 34 is a graph of the weights of animals administered tauroursodeoxycholic acid (TUDCA) or placebo and maintained on a high fat diet.
Figure 35:
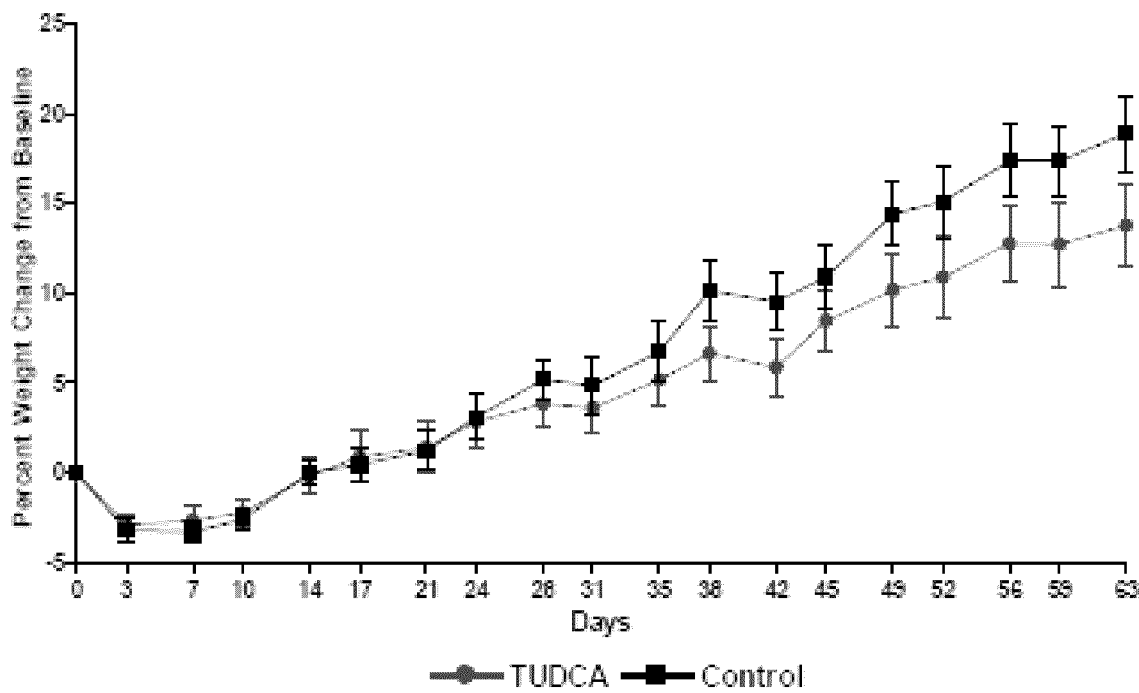
FIG. 35 is a graph of the percent weight change from baseline of animals administered TUDCA or placebo and maintained on a high fat diet.

Body weight was recorded twice a week, food intake was obtained weekly, and fasting blood glucose was measured every other week. While differences between the groups did not reach statistical significance, peripheral TUDCA administration resulted in a trend towards decreased weight gain on a RFD (FIG. 34). The percent weight change (FIG. 35) in the TUDCA animals showed a trend toward decreased weight even while maintained on a high fat diet. This suggests that extended monitoring of the animals beyond 52 days or more frequent dosing of bile acids may produce greater differences in weight change between TUDCA and placebo animals.

Figure 36:
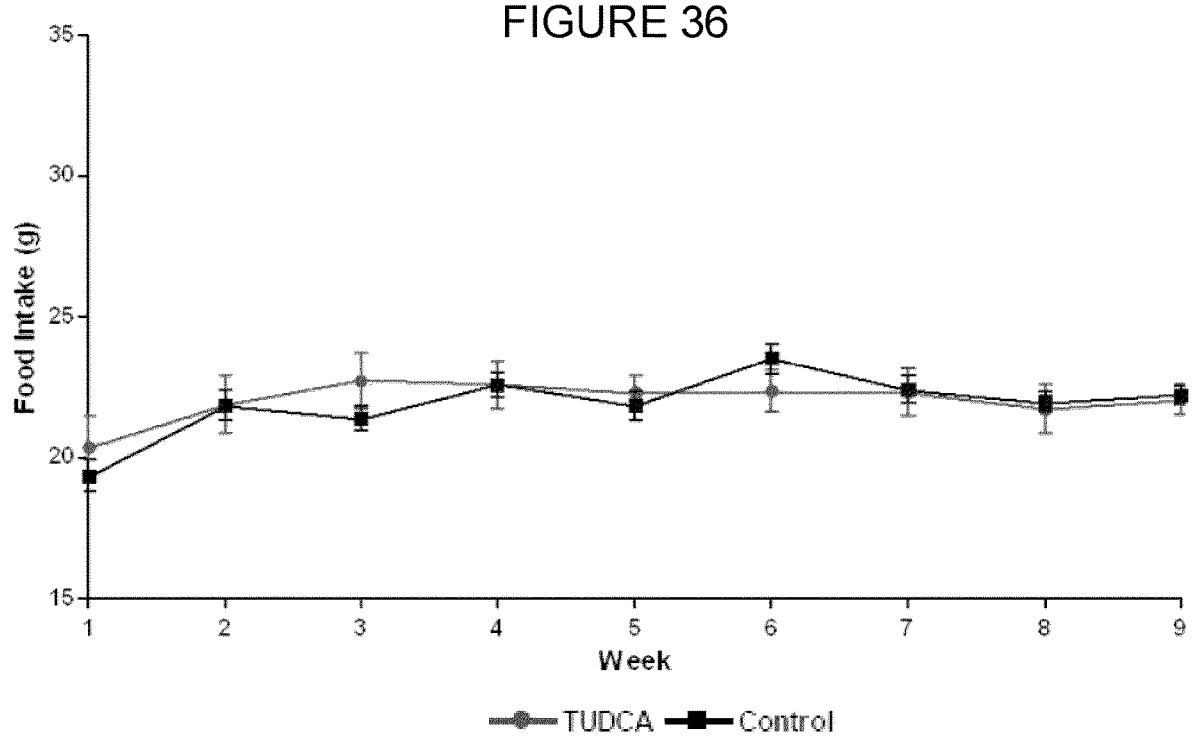
FIG. 36 is a graph of the weekly food intake of animals administered TUDCA or placebo.
Figure 37:
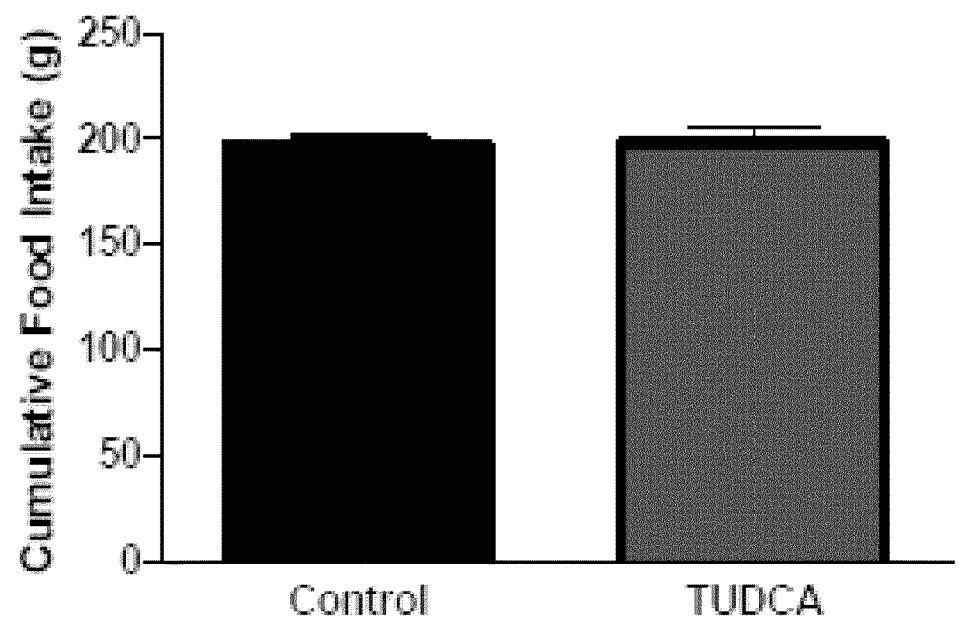
FIG. 37 is a graph of the cumulative food intake of animals administered TUDCA or placebo.

Moreover, weekly food intake (FIG. 36) and cumulative food intake (FIG. 37) of the TUDCA and placebo animals was similar. This suggests that peripheral administration of bile acids, like TUDCA, increases energy expenditure to effect weight loss in the animals since food intake was essentially the same among the two groups.

Example 7

In Vivo Delivery of Bile Acids

Eight Sprague-Dawley rats, between the ages of 34 and 38 weeks of age, were separated into two groups (4 rats per group) for the study. Group 1 included diet-induced obese rats maintained on 60% high fat diet that underwent Roux en Y gastric bypass operation 10 weeks prior to the start of the study, (RYGB). Group 2 included diet-induced obese rats maintained on 60% high fat diet that underwent sham operation 10 weeks prior to the start of the study, (Sham). All rats were maintained under standards and guidelines approved by Subcommittee on Research Animal Care for the Institutional Animal Care and Use Committee at Massachusetts General Hospital.

On day 0, all animals were administered a 3 cc liquid diet via oral gavage under anesthesia. Tail vein blood samples were obtained before (under anesthesia) and every 20 minutes for two hours after the liquid meal (no anesthesia).

Figure 38:
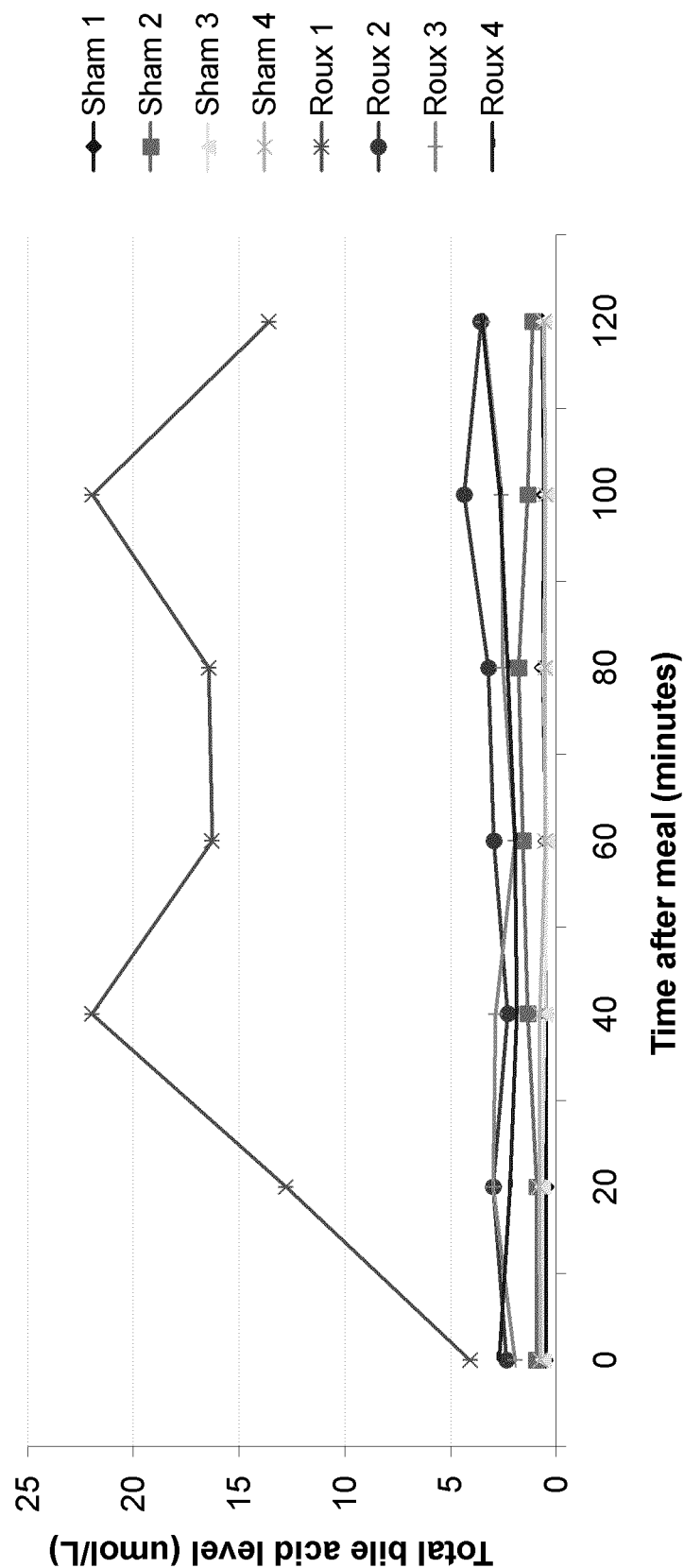
FIG. 38 is a time course graph of total bile acid levels in RYGB and Sham animals pre- and post-prandial.
Figure 39:
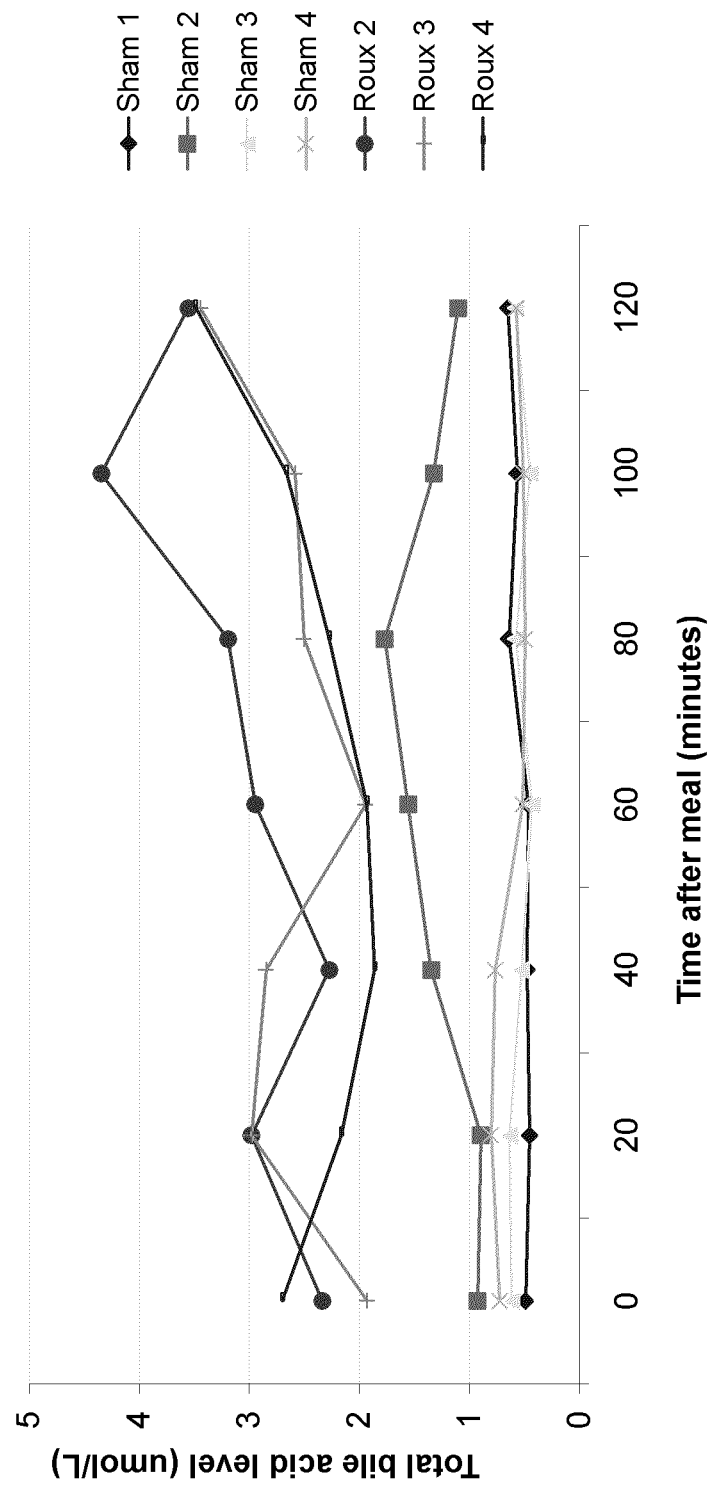
FIG. 39 is a time course graph of circulating bile acid levels in RYGB and Sham animals pre- and post-prandial with a single outlier excluded.
Figure 40:
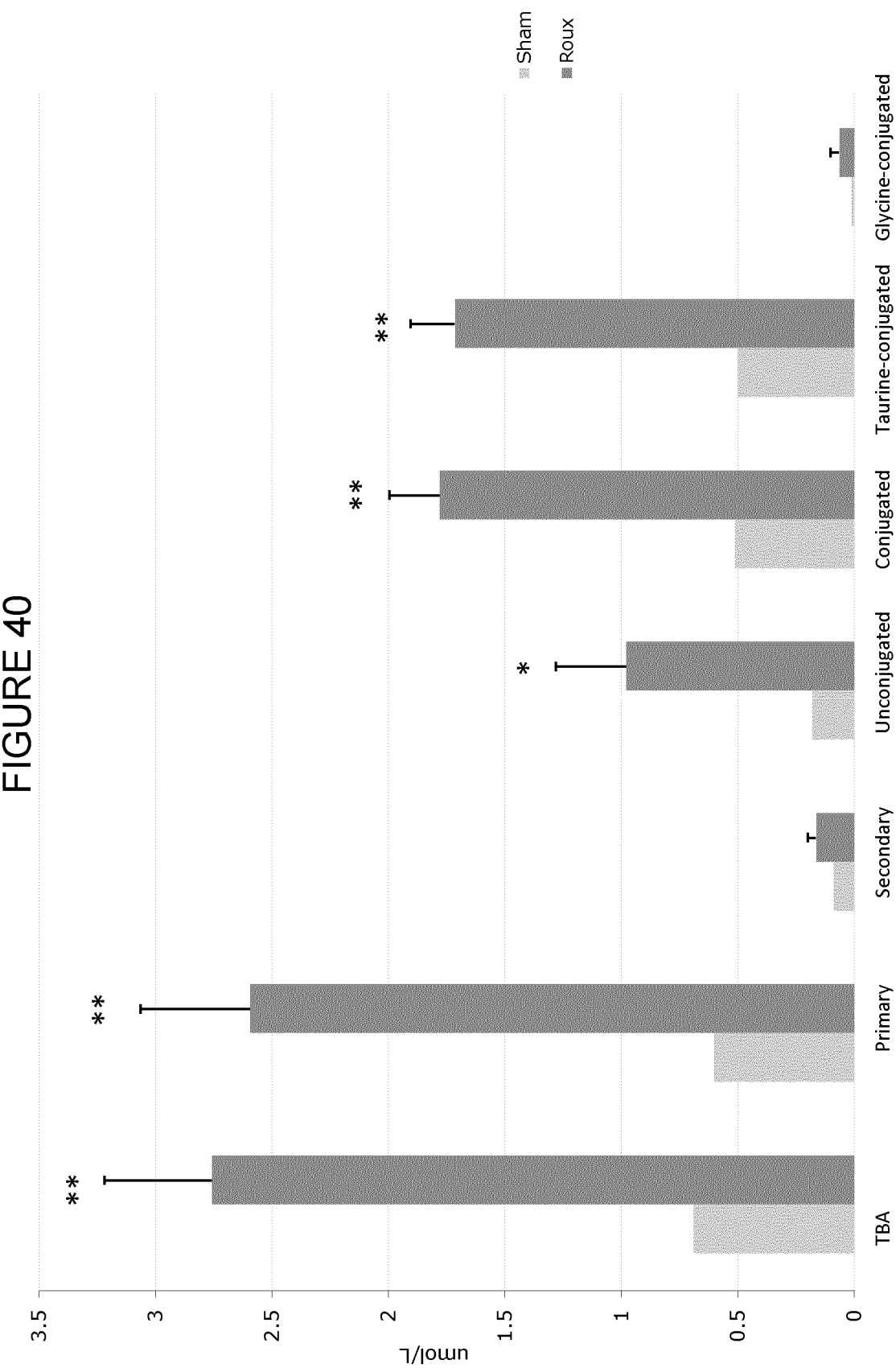
FIG. 40 is a graph of fasting bile acid subset levels in RYGB and Sham animals, *p<0.05, **p<0.01.
Figure 41:
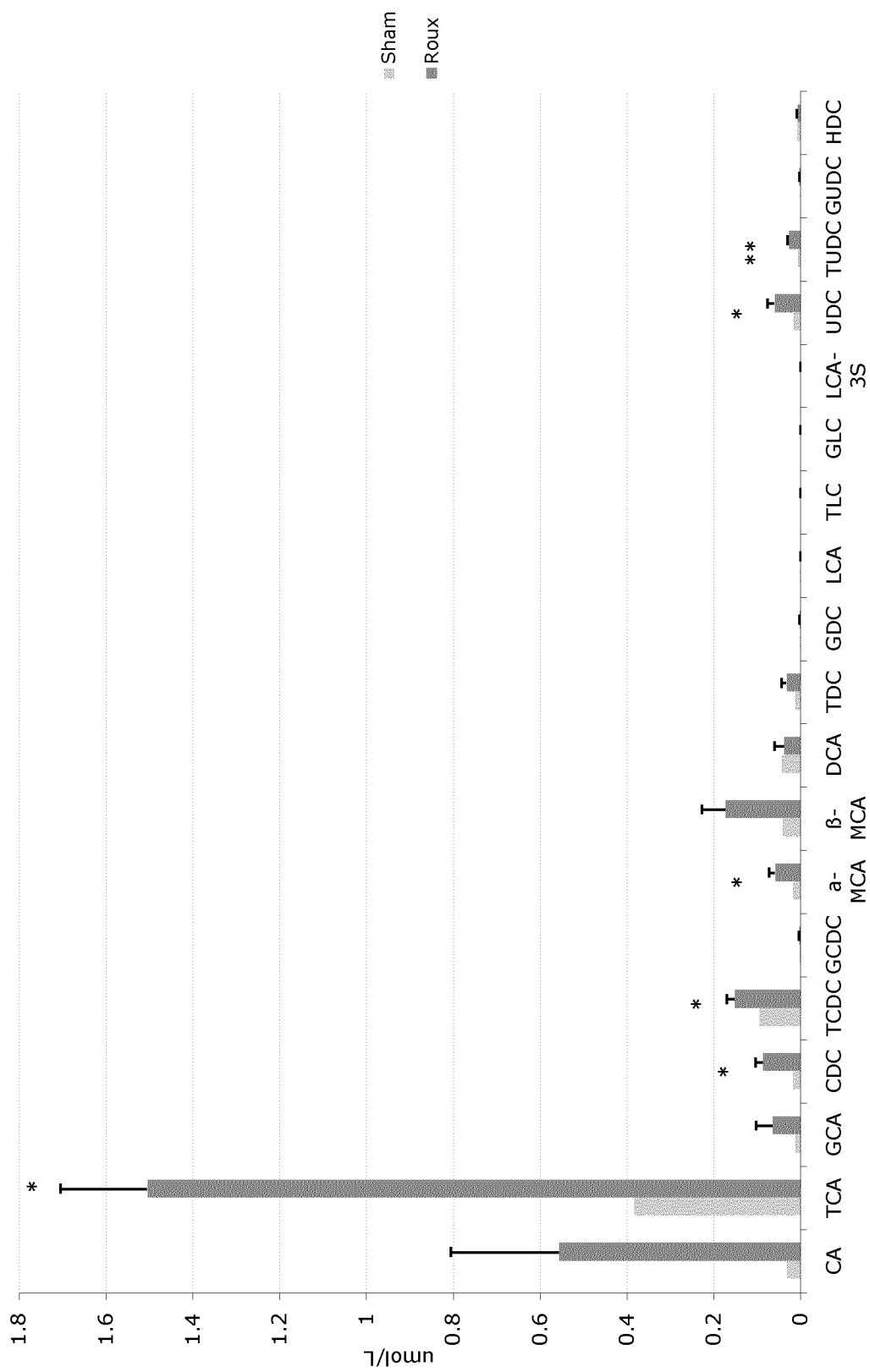
FIG. 41 is a graph of individual bile acid levels pre-prandial in RYGB and Sham animals, *p<0.05, **p<0.01.
Figure 42:
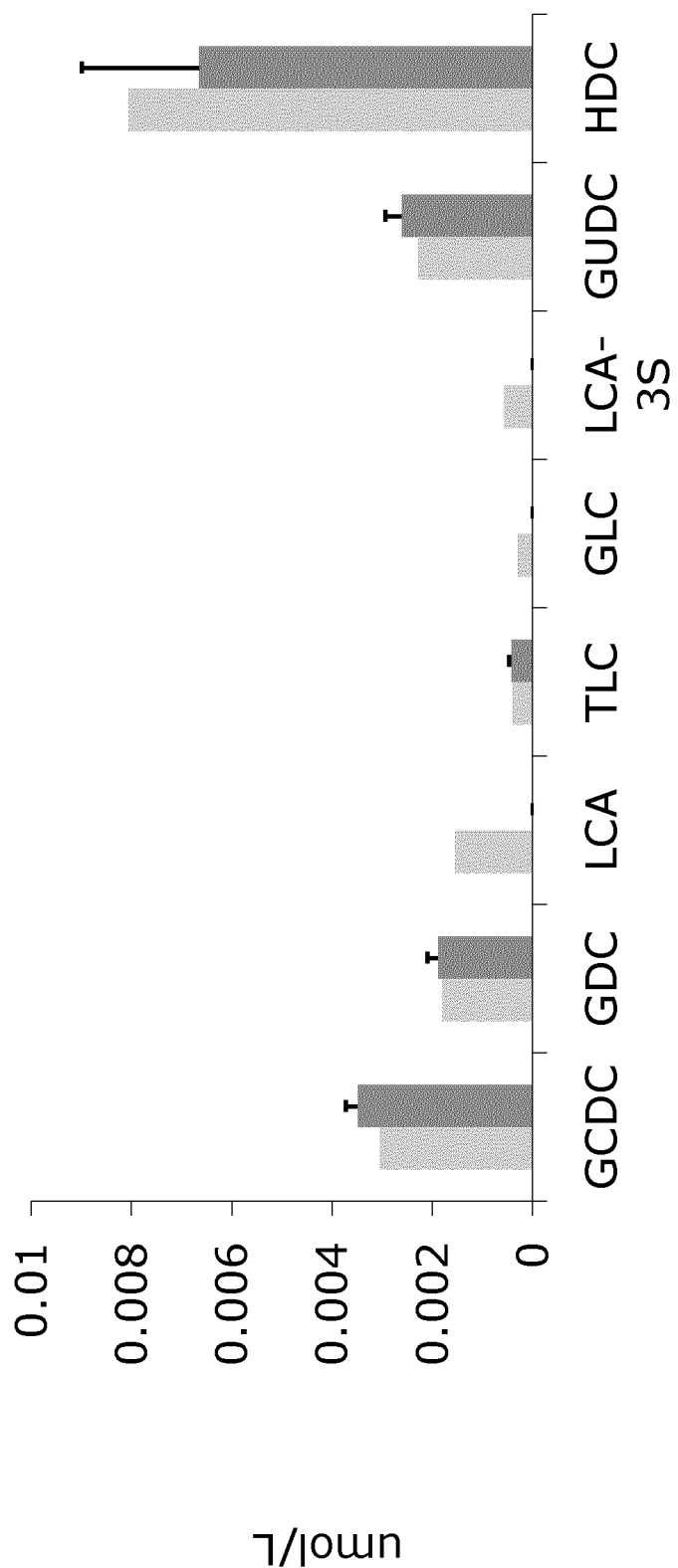
FIG. 42 is a graph of individual bile acid levels pre-prandial in RYGB and Sham animals, *p<0.05, **p<0.01.

Over the time course, total bile acid levels appeared stable, under 5 µmol/L for both RYGB and Sham animals, except one outlier (see FIG. 38). RYGB appears to increase the circulating bile acids pre- and post-prandial (FIG. 39). Also, fasting bile acid levels are significantly increased in RYGB animals. Total bile acids, primary, unconjugated, conjugated and taurin-conjugated bile acids were significantly increased in RYGB over Sham animals (FIG. 40). Levels of taurine cholic acid (TCA), chenodeoxycholic acid (CDC), taurochenodeoxycholic acid (TCDC), alpha-muricholic acid (α-MCA), ursodeoxycholic acid (UDC) and tauroursodeoxycholic acid (TUDC) all were significantly increased over Sham levels (FIGS. 41-42).

Figure 43:
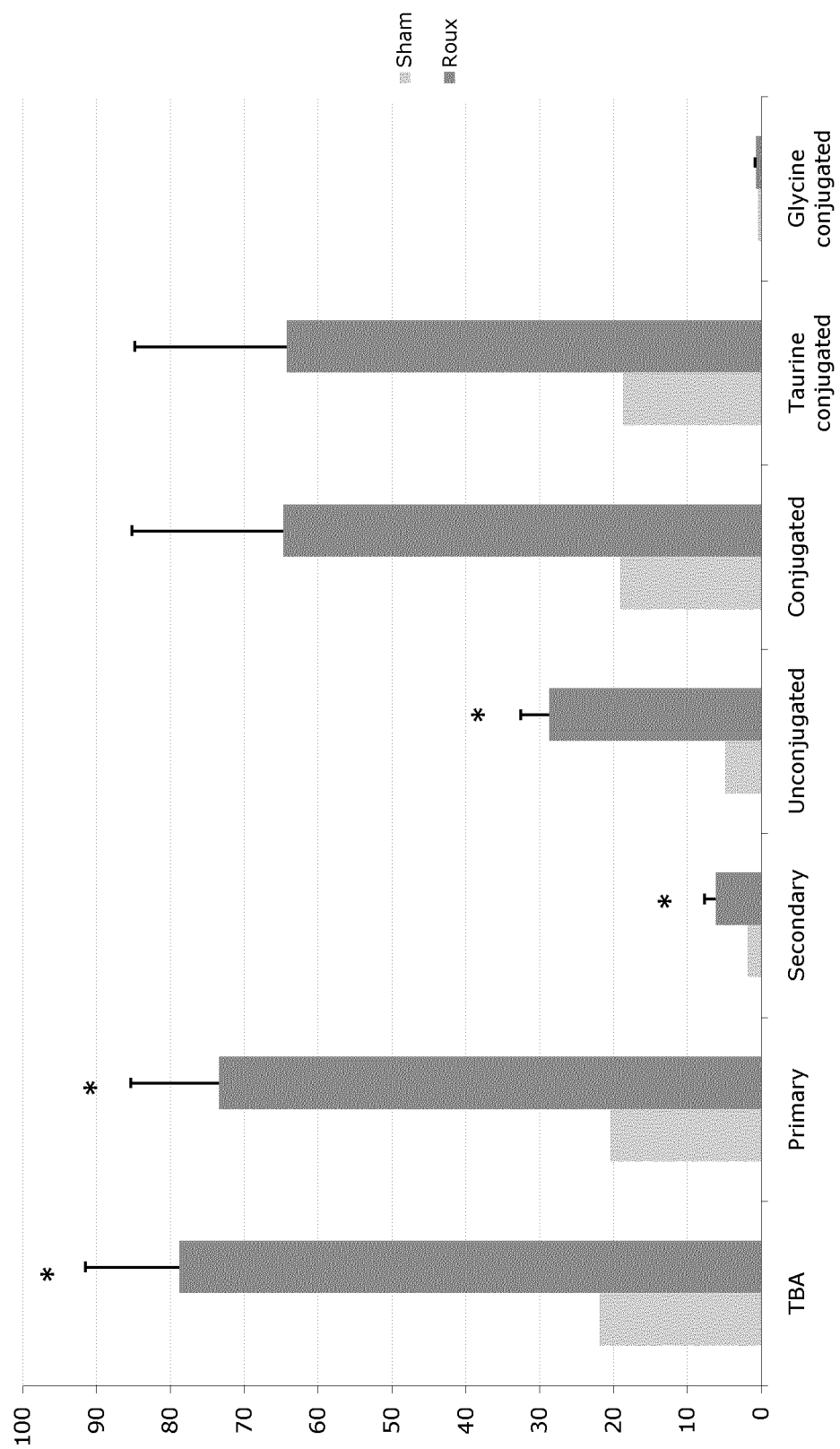
FIG. 43 is a graph of post-prandial bile acid subset levels in RYGB and Sham animals, *p<0.05, **p<0.01.
Figure 44:
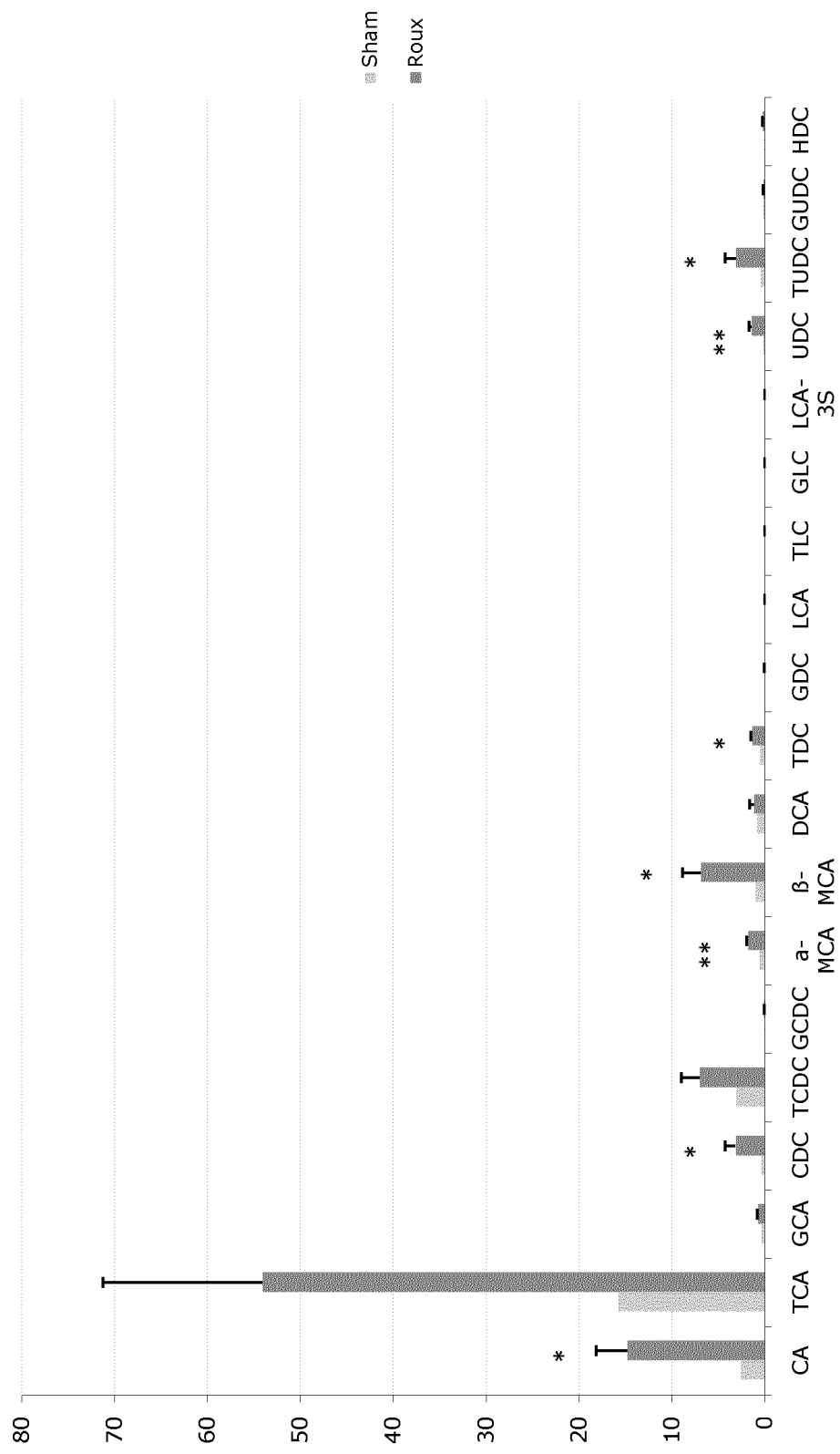
FIG. 44 is a graph of individual bile acid levels post-prandial in RYGB and Sham animals, *p<0.05, **p<0.01.

RYGB appears to increase the circulating bile acids post-prandial. The post-prandial total bile acids, primary, secondary, unconjugated, conjugated and taurin-conjugated bile acids were significantly increased in RYGB over Sham animals (FIG. 43). Levels of cholic acid (CA), chenodeoxycholic acid (CDC), taurochenodeoxycholic acid (TCDC), alpha-muricholic acid (α-MCA), beta-muricholic acid (β-MCA), taurodeoxycholic acid (TDC), ursodeoxycholic acid (UDC) and tauroursodeoxycholic acid (TUDC) all were significantly increased over Sham levels (FIG. 44).

Example 8

Pharmocokinetics of Subcutanteous TUDCA Administration

Pharmacokinetics of subcutaneous TUDCA administration were determined with C57BL/6J mice, 10 weeks of age, maintained on a high fat diet (D12492 diet; Research Diets, New Brunswick, N.J.). Animals were individually housed on bedding and maintained on a 12-hour light-dark cycle (lights on at 0700 hours) in a facility with an ambient temperature of 19-22° C. They were fed RFD ad libitum.

TUDCA was prepared on the day of injection in 0.15 M NaHCO$_3$ (pH adjusted to 7.4). TUDCA was administered subcutaneously as 10 µl solution/g of body weight. The animals were injected with TUDCA 500 mg/kg and euthanized for blood collection at the following time intervals: 0, 0.5, 1, 2, 4, 8, 12, 24, 48, 72, and 96 hours after injection (N=3 per time point).

Figure 45:
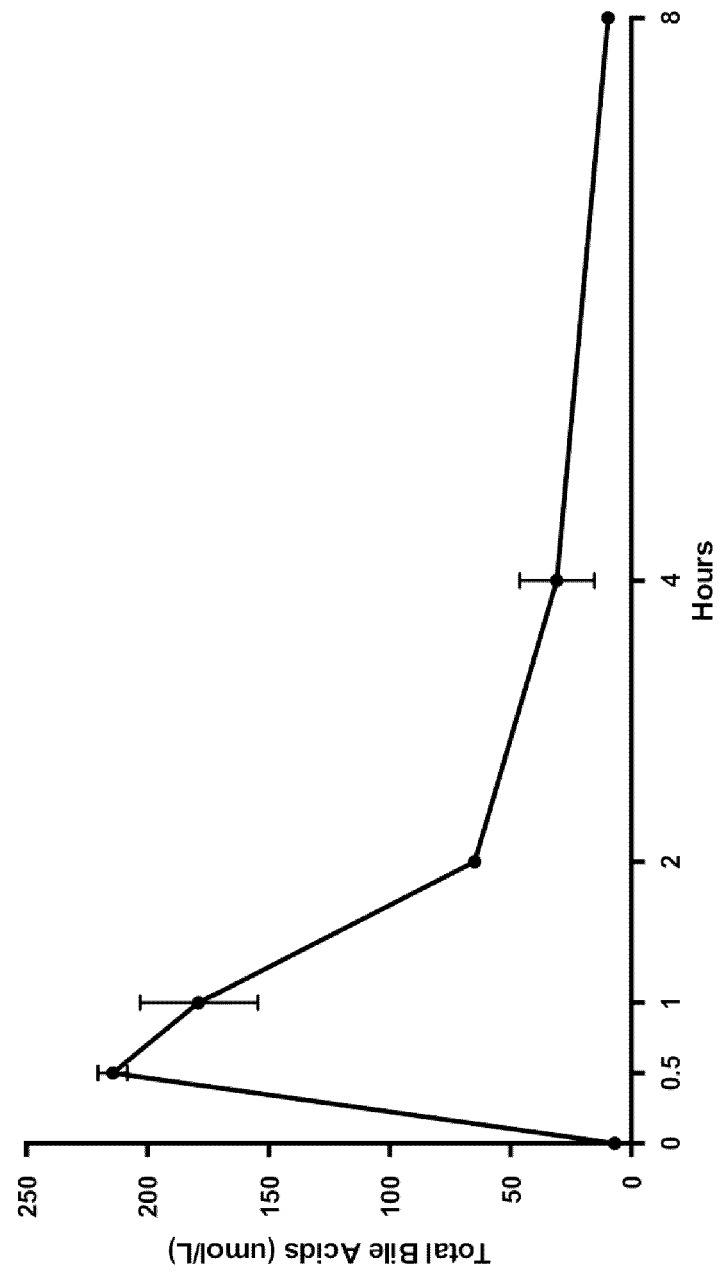
FIG. 45 is a graph of the pharmacokinetics of subcutaneous TUDCA administration of animals with prolonged bioavailability at 30 minutes to 4 hours post injection.

Body weight (BW) was measured and recorded immediately before injection. All injections were performed between 0800 and 0930 AM. Blood was collected via cardiac puncture after euthanizing the animal using CO$_2$ and cervical dislocation as approved by the Subcommittee on Research Animal Care (SRAC), the Institutional Animal Care and Use Committee (IACUC) for MGH. After immediate transfer to EDTA-containing tubes, samples were placed on ice and then centrifuged for 20 minutes at 4° C., and plasma aliquots were stored at −80° C. Total bile acids (TBA) were measured using the 3-α hydroxy-steroid dehydrogenase method (Diazyme TBA kit, DZ092A-K) and demonstrated subcutaneous administration provided prolonged bioavailability, 30 minutes to 4 hours post injection, above baseline levels, see FIG. 45.

Terminology

All publications, patents and patent applications cited herein are hereby incorporated by reference in their entirety. As used in this specification and the appended claims, the singular forms "a," "an," and "the" include plural references unless the content clearly dictates otherwise. The terms used in this invention adhere to standard definitions generally accepted by those having ordinary skill in the art. In case any further explanation might be needed, some terms have been further elucidated below.

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. The term does not denote a particular age or sex. In a specific embodiment, the subject is human.

As used herein, the term "metabolic disorders" refers to medical conditions characterized by problems with an organism's metabolism. Since a healthy, functioning metabolism is crucial for life, metabolic disorders are treated very seriously. A broad range of conditions including, but not limited to, diabetes (including type 1 and type 2 diabetes), hypo-thyroidism, and obesity are some examples of disorders that can be classified as metabolic disorders. Metabolic disorders can result in excessive weight gain. The term "metabolic syndrome" refers to a cluster of conditions that occur together, and increase the risk for heart disease, stroke and diabetes. Having just one of these conditions such as increased blood pressure, elevated insulin levels, excess body fat around the waist or abnormal cholesterol levels increases the risk of the above mentioned diseases. In combination, the risk for coronary heart disease, stroke and diabetes is even greater. The main features of metabolic syndrome include insulin resistance, hypertension, cholesterol abnormalities, and an increased risk for clotting. Patients are most often overweight or obese.

What is claimed is:

1. A method of increasing a serum bile acid level in an obese subject comprising:
   delivering to the subject a composition comprising a bile acid cocktail comprising at least four of a cholic acid, a taurine conjugated bile acid, a primary taurine conjugated bile acid, a secondary taurine conjugated bile acid, a sulfated bile acid, and/or a bile acid sequestrant, and
   wherein the composition increases the serum bile acid level thereby decreasing weight gain in the subject.

2. The method of claim 1 wherein the step of delivering the composition comprises delivering the bile acid to at least one of the circulatory system, the portal circulation, and the gastrointestinal tract.

3. The method of claim 1 wherein the step of delivering the composition comprises delivering the composition at least one of before a meal, with a meal, after a meal, and during a period of physical activity.

4. The method of claim 3 wherein the step of delivering the composition further comprises altering the serum bile acid level within about 3 hours of the meal.

5. The method of claim 3 wherein the step of delivering the composition further comprises increasing the serum bile acid level to a first level, decreasing the serum bile acid level to a second level, and increasing the serum bile acid level to a third level.

6. The method of claim 3 wherein the step of delivering the composition with a meal further comprises delivering an additional dosage of the composition during a non-meal period.

7. The method of claim 6 wherein the non-meal period is after a last meal of a first day and before breaking a fast of a second day.

8. The method of claim 1, further comprising delivering at least one agent to modulate activation of at least one bile acid receptor.

9. The method of claim 8, wherein the bile acid receptor is selected from the group consisting of a cell surface receptor and a nuclear receptor.

10. The method of claim 8, wherein the bile acid receptor is selected from the group consisting of a TGR5, a M3 muscarinic receptor, a FXR, a LXR, a RXR, a VDR, a ROR, and a POR.

11. The method of claim 1, wherein the composition is effective to treat a comorbid condition selected from the group consisting of hypertension, dyslipidemia, high triglyceride levels, diabetes, acid reflux, fatty liver disease, steatohepatitis, heart disease, heart failure, cardiovascular risk, depression, sleep apnea, Barrett's esophagus, asthma, arthritis, compression fractures, gallstones, lymphoedema, urinary incontinence, stroke, cognitive dysfunction, inflammatory diseases, autoimmune diseases, gout, polycystic ovarian syndrome, infertility, anxiety and/or panic disorders, cancer risk and mortality, wherein the cancer comprises adenocarcinoma of pancreas, esophagus, gallbladder, pancreas, colon, rectum, breast, prostate; cervical carcinoma, endometrial carcinoma, ovarian carcinoma, renal cell carcinoma, or non-Hodgkins lymphoma, weight regain, nutritional deficiency, constipation, diarrhea, marginal ulceration, dumping syndrome, reactive hypoglycemia, beta cell hyperfunction, gastrointestinal stenosis, liver disorders and nausea/vomiting.

12. A method of modulating a bile acid profile to treat obesity, type II diabetes mellitus and/or fatty liver disease in an obese subject, comprising:
delivering to the subject an amount of a composition comprising a bile acid cocktail that is effective to increase bile acid levels wherein the bile acid cocktail comprises at least four of a cholic acid, a taurine conjugated bile acid, a primary taurine conjugated bile acid, a secondary taurine conjugated bile acid, and/or a sulfated bile acid; and
obtaining an additional bile acid profile measurement in the subject after delivery of the composition, thereby modulating the bile acid profile of the subject to treat obesity, type II diabetes mellitus and/or fatty liver disease.

13. The method of claim 12 wherein the step of measuring the bile acid profile comprises measuring at least one of a glucose concentration, a leptin level, and an insulin level.

14. The method of claim 12 wherein the step of measuring the bile acid profile comprises measuring the bile acid profile of the subject at least during a fasting period, before a meal, or after a meal.

15. The method of claim 12 wherein the step of obtaining the additional bile acid profile measurement comprises obtaining the measurement at least during a fasting period, before a meal or after a meal.

16. The method of claim 1, wherein the bile acid cocktail comprises taurine taursodeoxycholic acid (TUDC), and at least one of taurine deoxycholic acid (TDC), glycine deoxycholic acid (GDC), taurine chenodeoxycholic acid (TCDC), glycine chenodeoxycholic acid (GCDC), taurine cholic acid (TCA), or glycocholic acid (GCA).

17. The method of claim 1, wherein the bile acid cocktail comprises TUDC, TDC, GDC, TCDC, GCDC, TCA, and GCA.

18. The method of claim 1, wherein the subject has undergone Roux en Y gastric bypass.

19. The method of claim 1, wherein the subject has not undergone Roux en Y gastric bypass.

* * * * *